(12) United States Patent
Santamaria et al.

(10) Patent No.: US 8,354,110 B2
(45) Date of Patent: *Jan. 15, 2013

(54) COMPOSITIONS AND METHODS FOR THE PREVENTION AND TREATMENT OF AUTOIMMUNE CONDITIONS

(75) Inventors: Pedro Santamaria, Calgary (CA); Anna Moore, Dracut, MA (US)

(73) Assignees: UTI Limited Partnership, Calgary, Alberta (CA); The General Hospital Corporation, Boston, MA (US)

(*) Notice: Subject to any disclaimer, the term of this patent is extended or adjusted under 35 U.S.C. 154(b) by 434 days.

This patent is subject to a terminal disclaimer.

(21) Appl. No.: 12/044,435

(22) Filed: Mar. 7, 2008

(65) Prior Publication Data

US 2009/0155292 A1    Jun. 18, 2009

Related U.S. Application Data

(60) Provisional application No. 60/893,530, filed on Mar. 7, 2007.

(51) Int. Cl.
*A61K 39/00* (2006.01)
*A61K 39/38* (2006.01)
*A01N 25/26* (2006.01)
*A01N 25/28* (2006.01)

(52) U.S. Cl. ............... 424/184.1; 424/421; 977/773

(58) Field of Classification Search .................. None
See application file for complete search history.

(56) References Cited

U.S. PATENT DOCUMENTS

| | | | |
|---|---|---|---|
| 4,414,148 A | 11/1983 | Jansen et al. | 530/391.9 |
| 4,569,789 A | 2/1986 | Blattler et al. | 530/391.9 |
| 4,589,431 A | 5/1986 | Yamamuro et al. | 701/55 |
| 4,589,330 A | 5/1986 | Teron | 454/185 |
| 4,659,839 A | 4/1987 | Nicolotti et al. | 548/546 |
| 4,671,958 A | 6/1987 | Rodwell et al. | 424/1.53 |
| 4,680,338 A | 7/1987 | Sundoro | 525/54.1 |
| 4,699,784 A | 10/1987 | Shih et al. | 424/181.1 |
| 4,818,542 A | 4/1989 | DeLuca et al. | 424/491 |
| 5,258,499 A * | 11/1993 | Konigsberg et al. | 530/351 |
| 5,543,391 A | 8/1996 | Yatvin et al. | 514/2 |
| 5,676,928 A * | 10/1997 | Klaveness et al. | 424/9.32 |
| 6,688,494 B2 | 2/2004 | Pozarnsky et al. | 222/4 |
| 6,712,997 B2 | 3/2004 | Won et al. | 252/503 |
| 6,797,514 B2 | 9/2004 | Berenson et al. | |
| 6,846,474 B2 | 1/2005 | Nayfeh et al. | 423/348 |
| 6,929,675 B1 | 8/2005 | Bunge et al. | 75/362 |
| 7,060,121 B2 | 6/2006 | Lin et al. | 75/362 |
| 7,285,289 B2 | 10/2007 | Nagy et al. | |
| 7,326,399 B2 | 2/2008 | Zhou et al. | 423/610 |
| 7,332,586 B2 | 2/2008 | Franzen et al. | 530/402 |
| 7,572,631 B2 | 8/2009 | Berenson et al. | |
| 2003/0068363 A1 | 4/2003 | Clark et al. | 424/450 |
| 2004/0137642 A1* | 7/2004 | Erfle et al. | 436/518 |
| 2005/0129617 A1* | 6/2005 | Tan et al. | 424/9.1 |
| 2005/0202032 A1 | 9/2005 | Kaufman et al. | 424/185.1 |
| 2007/0059775 A1 | 3/2007 | Hultman et al. | 435/7.2 |
| 2007/0129307 A1* | 6/2007 | Tan et al. | 514/14 |
| 2007/0154953 A1 | 7/2007 | Brunner et al. | 435/7.2 |
| 2010/0104503 A1 | 4/2010 | Mellman et al. | |

FOREIGN PATENT DOCUMENTS

| | | |
|---|---|---|
| EP | 0 188 256 | 7/1986 |
| WO | WO 01/24764 | 4/2001 |
| WO | WO 2004/078909 | 9/2004 |
| WO | WO2005/033267 * | 4/2005 |
| WO | WO 2006/080951 | 8/2006 |
| WO | WO 2008/118861 | 10/2008 |
| WO | WO 2009/111588 | 10/2008 |
| WO | WO 2009/040811 | 4/2009 |
| WO | WO 2009/094273 | 7/2009 |
| WO | WO 2010/080032 | 7/2010 |
| WO | WO 2011/073685 | 6/2011 |

OTHER PUBLICATIONS

Website article from kidshealth.org/PageManager.jsp?dn=KidsHealth&lic=1&ps=107&cat_id=139&article; downloaded Nov. 9, 2010: 2 pages total.*
Gill et al., Journal of Immunology, 1989; 143: 2176-2178.*
Tsai et al., Immunity, 2010; 32: 568-580.*
Bibliographic data page from EPO website at espacenet.com/publicationDetails/biblio?CC=WO&NR=2004078909A2&KC=..., downloaded Nov. 15, 2010, showing that WO2004078909 was also published as US2007154953: 1 page total.*
Weiss et al., Proc. Natl. Acad. Sci. USA, 1996; 93: 10945-10948.*
Warnock et al., Diabetologia, 1991; 34: 55-58.*
Karounos et al., JCI, 1997; 100: 1344-1348.*
Saragovi & Burgess, Exp Opin Ther Patents. 1999; 9: 737-751.*
Spada et al., 2000, J. Exp. Med. vol. 6: 937-948.*
Kukreja et al., 2002, Diabet. Tech. Ther. vol. 4: 323-333.*
Han et al., 2009, Immunology, vol. 129: 197-206.*
Van Belle, 2011, Physiol Rev. vol. 91: 79-118.*
Aichele et al., "Peptide-induced T-cell tolerance to prevent autoimmune diabetes in a transgenic mouse model," *Proc. Natl. Acad, Sci. USA*, 91: 444-448, 1994.
Amrani et al., "Expansion of the antigenic repertoire of a single T cell receptor upon T cell activation," *J. Immunol.*, 167: 655-666, 2001.
Amrani et al., "Progression of autoimmune diabetes driven by avidity maturation of a T-cell population," *Nature*, 406: 739-742, 2000.
Anderson et al., "Prevalent CD8(+) T cell response against one peptide/MHC complex in autoimmune diabetes," *Proc. Natl. Acad. Sci. USA*, 96: 9311-9316, 1999.
Anderton and Wraith, "Hierarchy in the ability of T cell epitopes to induce peripheral tolerance to antigens from myelin," *Eur. J. Immunol.*, 28: 1251-1261, 1998.

(Continued)

*Primary Examiner* — Amy Juedes
(74) *Attorney, Agent, or Firm* — Foley & Lardner LLP; Antoinette F. Konski; Laurie Stellman

(57) ABSTRACT

The methods include selectively reducing or expanding T cells according to the antigenic specificity of the T cells. Therefore, the present invention can be used to reduce or eliminate pathogenic T cells that recognize autoantigens, such as beta cell specific T cells. As such, the present invention can be used to prevent, treat or ameliorate autoimmune diseases such as IDDM. Furthermore, the present invention can be used to expand desirable T cells, such as anti-pathogenic T cells to prevent, treat and/or ameliorate autoimmune diseases.

21 Claims, 35 Drawing Sheets

OTHER PUBLICATIONS

Appay et al., "HIV-specific CD8+ T cells produce antiviral cytokines but are impaired in cytoltic function," *J. Exp. Med.*, 192: 63-72, 2000.

Bachmann et al., "Developmental regulation of Lck targeting to the CD8 coreceptor controls signaling in naïve and memory T cells," *J. Exp. Med.*, 189: 1521-1530, 1999.

Barber et al., "Restoring function in exhausted CD8 T cells during chronic viral infection," *Nature*, 439: 682-687, 2006.

Becker et al., "Interleukin 15 is required for proliferative renewal of virus-specific memory CD8 T cells," *J. Exp. Med.*, 195: 1541-1548, 2002.

Bielekova et al., "Encephalitogenic potential of the myelin basic protein peptide (amino acids 83-99) in multiple sclerosis: results of a phase II clinical trial with an altered peptide ligand," *Nat. Med.*, 6: 1167-1175, 2000.

Blancou et al., "Immunization of HLA class I transgenic mice identifies autoantigenic epitopes eliciting dominant responses in type 1 diabetes patients," *J. Immunol.*, 178: 7458-66, 2007.

Bottazzo et al., "In situ characterization of autoimmune phenomena and expression of HLA molecules in the pancreas in diabetic insulitis," *N. Engl. J. Med.*, 313: 353-360, 1985.

Bour-Jordan and Bluestone, "B cell depletion: a novel therapy for autoimmune diabetes?" *J. Clin. Invest.*, 117: 3642-3645, 2007.

Cao et al., "Analysis of the frequencies of HLA-A, B, and C alleles and haplotypes in the five major ethnic groups of the United States reveals high levels of diversity in these loci and contrasting distribution patterns in these populations," *Hum. Immunol.*, 62: 1009-30, 2001.

Diabetes Prevention Trial—Type 1 Diabetes Study Group, "Effects of insulin in relatives of patients with type 1 diabetes mellitus," N. Engl. J. Med., 346: 1685-1691, 2002.

DiLorenzo et al., "Major histocompatibility complex class I-restricted T cells are required for all but the end stages of diabetes development in nonobese diabetic mice and use a prevalent T cell receptor alpha chain gene rearrangement," *Proc. Natl. Acad. Sci. USA*, 95: 12538-12543, 1998.

Dressel et al., "Autoantigen recognition by human CD8 T cell clones: enhanced agonist response induced by altered peptide ligands," *J. Immunol.*, 159: 4943-51, 1997.

Fennessy et al., "A gene in the HLA class I region contributes to susceptibility to IDDM in the Finnish population. Childhood Diabetes in Finland (DiMe) Study Group," *Diabetologia*, 37: 937-945, 1994.

Guarda et al., "L-selectin-negative CCR7-effector and memory CD8+ T cells enter reactive lymph nodes and kill dendritic cells," *Nat. Immunol.*, 8: 743-752, 2007.

Hamilton-Williams et al., "Transgenic rescue implicates beta2-microglobulin as a diabetes susceptibility gene in nonobese diabetic (NOD) mice," *Proc. Natl. Acad. Sci. USA*, 98: 11533, 2001.

Han et al., "Developmental control of CD8 T cell-avidity maturation in autoimmune diabetes," *J. Clin. Invest.*, 115: 1879-87, 2005.

Han et al., "Prevention of diabetes by manipulation of anti-IGRP autoimmunity: high efficiency of a low-affinity peptide," *Nat. Med.*, 11: 645-652, 2005.

Hassainya et al., "Identification of naturally processed HLA-A2—restricted proinsulin epitopes by reverse immunology.," *Diabetes*, 54: 2053-2059, 2006.

Herold et al., "Anti-CD3 monoclonal antibody in new onset type I diabetes mellitus," *N. Eng. J. Med.*, 346: 1692-1698, 2002.

Honeyman et al., "Analysis of families at risk for insulin-dependent diabetes mellitus reveals that HLA antigens influence progression to clinical disease," *Mol. Med.*, 1: 576-582, 1995.

Itoh et al., "Mononuclear cell infiltration and its relation to the expression of major histocompatibility complex antigens and adhesion molecules in pancreas biopsy specimens from newly diagnosed insulin-dependent diabetes mellitus patients," *J. Clin. Invest.*, 92: 2313-2322, 1993.

Jarchum et al., "Identification of novel IGRP epitopes targeted in type I diabetes patients," *Clin. Immunol.*, 127: 359-365, 2008.

Jarchum et al., "In vivo cytotoxicity of insulin-specific CD8+ T-cells in HLA-A*0201 transgenic NOD mice," *Diabetes*, 56: 2551-60, 2007.

Judge et al., "Interleukin 15 controls both proliferation and survival of a subset of memory-phenotype CD8+ T cells," *J. Exp. Med.*, 196: 935-946, 2002.

Jurewicz et al., "MHC class I-restricted lysis of human oligodendrocytes by myelin basic protein peptide-specific CD8 T lymphocytes," *J. Immunol.*, 160: 3056-3059, 1998.

Kappos et al., "Induction of a non-encephalitogenic type 2 T helper-cell autoimmune response in multiple sclerosis after administration of an altered peptide ligand in a placebo-controlled, randomized phase II trial. The Altered Peptide Ligand in Relapsing MS Study Group," *Nat. Med.*, 6: 1176-1182, 2000.

Karin et al., "Reversal of experimental autoimmune encephalomyelitis by a soluble peptide variant of a myelin basic protein epitope: T cell receptor antagonism and reduction of interferon gamma and tumor necrosis factor alpha production," *J. Exp. Med.*, 180: 2227-2237, 1994.

Kent et al., "Expanded T cells from pancreatic lymph nodes of type 1 diabetic subjects recognize an insulin epitope," *Nature*, 435: 224-228, 2005.

Keymeulen et al., "Insulin needs after CD3-antibody therapy in new-onset type 1 diabetes," *N. Engl. J. Med.*, 352: 2598-2608, 2005.

Kim et al., "Induction and visualization of mucosal memory CD8 T cells following systemic virus infection," *J. Immunol.*, 163: 4125-4132, 1999.

Lechner et al., "Analysis of successful immune responses in persons infected with hepatitis C virus," *J. Exp. Med.*, 191: 1499-1510, 2000.

Liblau et al., "Autoreactive CD8 T cells in organ-specific autoimmunity: emerging targets for therapeutic intervention," *Immunity*, 17: 1-6, 2002.

Lieberman and DiLorenzo, "A comprehensive guide to antibody and T-cell responses in type 1 diabetes.," *Tissue Antigens*, 62: 359-377, 2003.

Lieberman et al., "Identification of the β cell antigen targeted by a prevalent population of pathogenic CD8+ T cells in autoimmune," *Proc. Natl. Acad. Sci. USA*, 100: 8384-8388, 2003.

Lieberman et al., "Individual nonobese diabetic mice exhibit unique patterns of CD8+ T cell reactivity to three islet antigens, including the newly identified widely expressed dystrophia myotonica kinase," *J. Immunol.*, 173: 6727-6734, 2004.

Mallone et al., "CD8+ T-cell responses identify beta-cell autoimmunity in human type 1 diabetes," *Diabetes*, 56: 613-621, 2007.

Marée et al., "Modeling competition among autoreactive CD8+ T cells in autoimmune diabetes: implications for antigen-specific therapy," *Int. Immunol.*, 18: 1067-1077, 2006.

Mars et al., "CD8 T cell responses to myelin oligodendrocyte glycoprotein-derived peptides in humanized HLA-A*0201-transgenic mice," *J. Immunol.*, 179: 5090-5098, 2007.

McKown et al., "Lack of efficacy of oral bovine type II collagen added to existing therapy in rheumatoid arthritis," *Arthritis Rheum.*, 42: 1204-1208, 1999.

Mescher et al., "Signals required for programming effector and memory development by CD8+ T cells," *Immunol. Rev.*, 211: 81-92, 2006.

Metzler and Wraith, "Inhibition of experimental autoimmune encephalomyelitis by inhalation but not oral administration of the encephalitogenic peptide: influence of MHC binding affinity," *Int. Immunol.*, 5: 1159-1165, 1993.

Miller et al., "The induction of cell-mediated immunity and tolerance with protein antigens coupled to syngeneic lymphoid cells," *J. Exp. Med.*, 149: 758-766, 1979.

Moore et al., "Tracking the recruitment of diabetogenic CD8+ T-cells to the pancreas in real time," *Diabetes*, 53: 1459-1466, 2004.

Nakayama et al., "Prime role for an insulin epitope in the development of type 1 diabetes in NOD mice," *Nature*, 435: 220-224, 2005.

Ouyang et al., "Recognition of HLA class I-restricted beta-cell epitopes in type 1 diabetes," *Diabetes*, 55: 3068-3074, 2006.

Palmer et al., "Insulin antibodies in insulin-dependent diabetics before insulin treatment," *Science*, 222: 1337-1339, 1983.

Pascolo et al., "HLA-A2.1-restricted education and cytolytic activity of CD8(+) T lymphocytes from beta2 microglobulin (beta2m) HLA-A2.1 monochain transgenic H-2Db beta2m double knockout mice," *J. Exp. Med.*, 185: 2043, 1997.

Pinkse et al., "Autoreactive CD8 T cells associated with beta cell destruction in type 1 diabetes," *Proc. Natl. Acad. Sci. USA*, 102: 18425-18430, 2005.

Oh et al., "IL-15/IL avidity maturation of memory CD8+ T cells," *Proc. Natl. Acad. Sci. USA*, 101: 15154-15159, 2004.

Santamaria et al., "Beta-cell-cytotoxic CD8+ T cells from nonobese diabetic mice use highly homologous T cell receptor alpha-chain CDR3 sequences," *J. Immunol.*, 154: 2494, 1995.

Santamaria et al., "Characterization of T lymphocytes infiltrating human pancreas allograft affected by isletitis and recurrent diabetes," *Diabetes*, 41: 53-61, 1992.

Santamaria et al., "Skewed TCR usage and junctional heterogeneity among isletitis ab and gd T cells in human type 1 diabetes," *Diabetes*, 43: 599-606, 1994.

Santamaria, "Effector lymphocytes in autoimmunity," *Curr. Opin. Immunol.*, 13: 663-669, 2001.

Schutgen et al., "A directional strategy for monitoring Cre-mediated recombination and the cellular level in the mouse," *Nat. Biotech.*, 21: 562-566, 2003.

Serreze et al., "Autoreactive diabetogenic T-cells in NOD mice can efficiently expand from a greatly reduced precursor pool," *Diabetes*, 50: 1992-2000, 2001.

Sibley et al., "Recurrent diabetes mellitus in the pancreas iso- and allograft. A light and electron microscopic and immunohistochemical analysis of four cases," *Lab. Invest.*, 53: 132-144, 1985.

Somoza et al., "Pancreas in recent onset insulin-dependent diabetes mellitus. Changes in HLA, adhesion molecules and autoantigens, restricted T cell receptor V beta usage, and cytokine profile," *J. Immunol.*, 153: 1360-1377, 1994.

Sprent and Surh, "T cell memory," *Annu. Rev. Immunol.*, 20: 551-579, 2002.

Sprent and Tough, "T cell death and memory," *Science*, 293: 245-248, 2001.

Standifer et al., "Identification of novel HLA-A*0201-restricted epitopes in recent-onset type 1 diabetic subjects and antibody-positive relatives," *Diabetes*, 55: 3061-3067, 2006.

Tait et al., "HLA antigens and age at diagnosis of insulin-dependent diabetes mellitus," *Hum. Immunol.*, 42: 116-124, 1995.

Takaki et al., "HLA-A*0201-restricted T cells from humanized NOD mice recognize autoantigens of potential clinical relevance to type 1 diabetes," *J. Immunol.*, 176: 3257-3265, 2006.

Tan et al., "Interleukin (IL)-15 and IL-7 jointly regulate homeostatic proliferation of memory phenotype CD8+ cells but are not required for memory phenotype CD4+ cells," *J. Exp. Med.*, 195: 1523-1532, 2002.

Toes et al., "Peptide vaccination can lead to enhanced tumor growth through specific T-cell tolerance induction," *Proc. Natl. Acad. Sci. USA*, 93: 7855-7860, 1996.

Toma et al., "Recognition of a subregion of human proinsulin by class I-restricted T cells in type 1 diabetic patients," *Proc. Natl. Acad. Sci. USA*, 102: 10581-10585, 2005.

Trentham et al., "Effects of oral administration of type II collagen on rheumatoid arthritis," *Science*, 261: 1727-1730, 1993.

Trudeau et al., "Prediction of spontaneous autoimmune diabetes in NOD mice by quantification of autoreactive T cells in peripheral blood," *J. Clin. Invest.*, 111: 217-223, 2003.

Tsuchida et al., "Autoreactive CD8+ T-cell responses to human myelin protein-derived peptides," *Proc. Natl. Acad. Sci. USA*, 91: 10859-63, 1994.

Unger et al., "Human clonal CD8 autoreactivity to an IGRP islet epitope shared between mice and men," *Ann. N.Y. Acad. Sci.*, 1103: 192-195, 2007.

Verdaguer et al., "Acceleration of spontaneous diabetes in TCR-transgenic nonobese diabetic mice by beta cell-cytotoxic CD8+ T-cells in autoimmunity," *Curr. Opin. Immunol.*, 17: 624-631, 2005.

Verdaguer et al., "Spontaneous autoimmune diabetes in monoclonal T cell nonobese diabetic mice," *J. Exp. Med.*, 186: 1663-1676, 1997.

Walter and Santamaria, "CD8+ T cells in autoimmunity," *Curr. Opin. Immunol.*, 17: 624-631, 2005.

Weiner, "Double-blind pilot trial of oral tolerization with myelin antigens in multiple sclerosis," *Science*, 259: 1321-1324, 1993.

Williams et al., "Developing and maintaining protective CD8+ memory T cells," *Immunol. Rev.*, 211: 146-153, 2006.

Winer et al., "Autoimmune islet destruction in spontaneous type 1 diabetes is not beta-cell exclusive," *Nat. Med.*, 9: 198-205, 2003.

Wong et al., "Identification of an MHC class I-restricted autoantigen in type 1 diabetes by screening an organ-specific cDNA library," *Nat. Med.*, 5: 1026-1031, 1999.

Wraith et al., "Antigen recognition in autoimmune encephalomyelitis and the potential for peptide-mediated immunotherapy," *Cell*, 59: 247-255, 1989.

Yamanouchi et al., "Interleukin-2 gene variation impairs regulatory T cell function and causes autoimmunity," *Nat. Genet.*, 39: 329-337, 2007.

Zajac et al., "Viral immune evasion due to persistence of activated T cells without effector function," *J. Exp. Med.*, 188: 2205-2213, 1998.

Kulmala, P. (2003)"Prediabetes in Children," Pediatr Drugs, 5(4):211-221.

U.S. Appl. No. 13/249,105, filed Sep. 29, 2011, Santamaria.

U.S. Appl. No. 13/294,109, filed Nov. 10, 2011, Santamaria.

Bottini, M. et al. "Luminescent Silica Nanobeads: Characterization and Evaluation as Efficient Cytoplasmatic Transporters for T-Lymphocytes," Journal of the American Chemical Society, vol. 129. No. 25, pp. 7814-7823, 2007.

Dominguez, A.L. et al. Targeting the tumor microenvironment with anti-neu/anti-CD40 conjugated nanoparticles for the induction of antitumor immune responses, Vaccine, vol. 28, No. 5, pp. 1383-1390, 2010.

Gong, W. et al "Immobilized MHC class I chain-related protein A syne g zes with IL-15 and soluble 4-1BB ligand to expand NK cells with high cytotoxicity ex vivo," Cellular & Molecular Immunology, Sep. 27, 2010, vol. 7, No. 6, pp. 477-484.

Jigna, D.P. et al. "Cationic Nanoparticles for Delivery of CpG Oligodexoynucleotide and Ovalbumin: In Vitro and In Vivo Assessment," Journal of Biomedical Nanotechnology, Apr. 2007, vol. 3, No. 1, pp. 97-106.

Komai-Koma, M. "TIR2 is expressed on activated T cells as a costimulatory receptor," Proceedings of the National Academy of Sciences, vol. 181. No. 9, pp. 3829-3834, 2004.

Kwong B. et al. "Synthesis and characterization of antibody-nanoparticle conjugates for locally sequestered tumor immunotherapy," Abstracts of Papers American Chemical Society, vol. 240, POLY 61, p. POLY, 2010.

Lee, Y. et al. "Biodegradable nanoparticles containing TLR3 or TLR9 agonists together with antigen enhance MHC-restricted presentation of the antigen," Archives of Pharmacal Research, vol. 1. 33, No. 11, pp. 1859-1866, 2010.

Requirement for Restriction/Election dated Jan. 10, 2012 for co-pending U.S. Appl. No. 12/044,435.

Office Action dated Apr. 4, 2012 for co-pending U.S. Appl. No. 12/044,435.

Petros, R. et al. "Antibody conjugation to Print nanoparticles as a cellular targeting strategy," Abstracts of Papers American Chemical Society, vol. 233. COLL 14, p. COLL14, 2007.

Purton, J.F. et al. "Antiviral CD4 memory T cells are IL-15 dependent," Journal of Experimental Medicine, Jan. 1, 2007, vol. 204, No. 4, pp. 951-961.

Schreiber, H.A. et al. "Using carbon 31-33 magnetic nanoparticles to target, track, and manipulate dendritic cells," Journal of Immunological Methods, vol. 356, No. 1-2, pp. 47-59, 2010.

Wang, X. et al. "Induction of Potent CD8 T-Cell Responses by Novel Biodegradable nanoparticles carrying Human Immunodeficiency Virus Type 1 gp 120," Journal of Virology, Sep. 15, 2007, vol. 81, No. 18, pp. 10009-10016.

Office Action for U.S. Appl. No. 12/848,055, mailed Aug. 23, 2012.

Office Action for U.S. Appl. No. 12/848,055, mailed Apr. 4, 2012.

Patel, J.D. et al. (2007) "Cationic Nanoparticles for Delivery of CpG Oligodeoxynucleotide and Ovalbumin: In Vitro and In Vivo Assessment," J. Biomed. Nanotechnol. 3(1):97-106.

Restriction Requirement for U.S. Appl. No. 12/848,055, mailed Feb. 1, 2012.

* cited by examiner

SEQUENCE LISTING

```
<160> NUMBER OF SEQ ID NOS: 58

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Leu Val Glu Ala Leu Tyr Leu Val
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Asn Ile Asp Leu Leu Trp Ser Val
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Leu Phe Gly Leu Gly Phe Ala Ile
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Tyr Leu Lys Thr Asn Val Phe Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 5

Val Tyr Leu Lys Thr Asn Leu Phe Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Tyr Asn Lys Ala Asn Ala Phe Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Tyr Asn Ile Ala Asn Val Phe Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Tyr Asn Lys Ala Asn Val Phe Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Gln Asp Glu Asn Tyr Leu Tyr Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Tyr Leu Val Cys Gly Glu Arg Gly
1               5

<210> SEQ ID NO 11
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 11

Leu Tyr Leu Val Cys Gly Glu Arg Ile
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Tyr Gln Ala Val Thr Thr Thr Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Tyr Cys Leu Ile Thr Ile Phe Leu
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Met Asn Ile Leu Leu Gln Tyr Val Val
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Met Met Glu Tyr Gly Thr Thr Met Val
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Leu Ala Gln Thr Asp Leu Ala Thr Val
1               5                   10
```

```
<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Leu Ala Arg Gln Gln Val His Val
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Leu Ser Pro Leu Gln Ala Glu Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Leu Ala Ala Gly Val Lys Leu Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Ile Val Met Leu Thr Pro Leu Val
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Leu Gln Val Phe Leu Ile Val Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

-continued

Phe Leu Ile Val Leu Ser Val Ala Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Leu Trp Ser Val Phe Met Leu Ile
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asn Leu Phe Leu Phe Leu Phe Ala Val
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Phe Leu Phe Ala Val Gly Phe Tyr Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Leu Leu Leu Arg Val Leu Asn Ile
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Leu Leu Cys Ala Leu Thr Ser Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Ala Leu Trp Met Arg Leu Leu Pro Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Trp Met Arg Leu Leu Pro Leu Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Leu Leu Pro Leu Leu Ala Leu Leu
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His Leu Cys Gly Ser His Leu Val Glu Ala
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Leu Tyr Leu Val Cys Gly Glu Arg
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Tyr Leu Val Cys Gly Glu Arg Gly Phe
1               5                   10

<210> SEQ ID NO 34
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Val Cys Gly Glu Arg Gly Phe Phe
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Cys Gly Glu Arg Gly Phe Phe Tyr Thr
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Glu Arg Gly Phe Phe Tyr Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Arg Gly Phe Phe Tyr Thr Pro Lys
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Tyr Thr Pro Lys Thr Arg Arg Glu
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Pro Lys Thr Arg Arg Glu Ala Glu Asp Leu
1               5                   10
```

```
<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Leu Gln Pro Leu Ala Leu Glu Gly
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Leu Glu Gly Ser Leu Gln Lys Arg
1               5

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Leu Gln Lys Arg Gly Ile Val Glu Gln
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Ile Val Glu Gln Cys Cys Thr Ser Ile
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Val Glu Gln Cys Cys Thr Ser Ile
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 45

Ser Leu Tyr Gln Leu Glu Asn Tyr Cys
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Leu Leu Leu Glu Leu Glu Glu Val
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Met Trp Ala Lys Ile Gly Pro Val
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Leu Phe Ser Ser Asp Phe Arg Ile
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Leu Ser Arg Phe Ser Trp Gly Ala
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Val Glu Asp Pro Phe Tyr Trp Val
1               5

<210> SEQ ID NO 51
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 51

Arg Thr Phe Asp Pro His Phe Leu Arg Val
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Leu Arg Val Pro Cys Trp Lys Ile
1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Ile Thr Leu Phe Val Ile Val Pro Val
1               5                   10

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Leu Gly Pro Leu Val Ala Leu Ile
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Leu Phe Val Ile Val Pro Val Leu
1               5

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Leu Ala Gly Gln Phe Leu Glu Glu Leu
1               5                   10
```

```
<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Leu Tyr Gly Ala Leu Leu Leu Ala
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Val Tyr Leu Ala Thr Asn Val Ala Leu
1               5
```

US 8,354,110 B2

COMPOSITIONS AND METHODS FOR THE PREVENTION AND TREATMENT OF AUTOIMMUNE CONDITIONS

This application claims priority to U.S. Provisional Patent application No. 60/893,530 filed on Mar. 7, 2007, which is hereby incorporated by reference in its entirety.

The United States Government owns rights in the present invention pursuant to grant 5R01 DK064850-03 from the NIH.

SEQUENCE LISTING

The instant application contains a Sequence Listing which has been submitted in ASCII format via EFS-Web and is hereby incorporated by reference in its entirety. Said ASCII copy, created on Nov. 9, 2010, is named 37871202.txt and is 13,578 bytes in size.

BACKGROUND OF THE INVENTION

I. Field of the Invention

This invention embodies compositions and methods related to immunology and medicine. In particular the invention is related to diagnostics and therapeutics for the diagnosis and treatment of autoimmune conditions, particularly diabetes.

II. Background

Antigen vaccination can be used for the induction of T-cell tolerance in autoimmunity. Administration of autoantigenic proteins or peptides in solution can blunt the initiation and/or progression of autoimmunity in experimental models of autoimmune disease (Wraith et al., 1989; Metzler and Wraith, 1993; Liu and Wraith, 1995; Anderton and Wraith, 1998; Karin et al., 1994). However, limited clinical trials in humans employing similar strategies have almost invariably met with failure (Weiner, 1993; Trentham et al., 1993; McKown et al., 1999; Pozzilli et al., 2000; Group, D.P.T.-T.D.S. 2002; Kappos et al., 2000; Bielekova et al., 2000). This suggests that the principles guiding the choice and conditions of treatment are poorly defined and, as a result, inadequate for human application.

Spontaneous organ-specific autoimmune disorders result from complex responses against numerous epitopes in multiple antigens that arise spontaneously in a stochastic and often unpredictable sequence. This complexity is compounded by the fact that lymphocyte clones recognizing identical epitopes engage antigen/major histocompatibility complex (MHC) molecules within a broad range of avidities, the strength of which correlates with pathogenic potential (Amrani et al., 2000; Santamaria, 2001; Liblau et al., 2002). Consequently, the outcome of any immunization strategy for the prevention of autoimmunity is likely to be influenced by the choice of autoantigen(s), dose, periodicity of treatment, and route and form of administration.

Type 1 Diabetes (T1D) in mice is associated with autoreactive CD8+ T-cells. Nonobese diabetic (NOD) mice develop a form of T1D, closely resembling human T1D, that results from selective destruction of pancreatic β cells by T-cells recognizing a growing list of autoantigens (Lieberman and DiLorenzo, 2003). Although initiation of T1D clearly requires the contribution of CD4+ cells, there is compelling evidence that T1D is CD8+ T-cell-dependent (Santamaria, 2001; Liblau et al., 2002). It has been discovered that a significant fraction of islet-associated CD8+ cells in NOD mice use CDR3-invariant Vα17-Jα42+ TCRs, referred to as '8.3-TCR-like' (Santamaria et al., 1995; Verdaguer et al., 1996; Verdaguer et al., 1997; DiLorenzo et al., 1998). These cells, which recognize the mimotope NRP-A7 (defined using combinatorial peptide libraries) in the context of the MHC molecule $K^d$ (Anderson et al., 1999), are already a significant component of the earliest NOD islet CD8+ infiltrates (DiLorenzo et al., 1998; Anderson et al., 1999; Amrani et al., 2001), are diabetogenic (Verdaguer et al., 1996; Verdaguer et al., 1997), and target a peptide from islet-specific glucose-6-phosphatase catalytic subunit-related protein (IGRP) (Lieberman et al., 2003), a protein of unknown function (Arden et al., 1999; Martin et al., 2001). The CD8+ cells that recognize this peptide (IGRP$_{206-214}$, similar to NRP-A7) are unusually frequent in the circulation (>1/200 CD8+ cells) (Lieberman et al., 2003; Trudeau et al., 2003). Notably, progression of insulitis to diabetes in NOD mice is invariably accompanied by cyclic expansion of the circulating IGRP$_{206-214}$-reactive CD8+ pool (Trudeau et al., 2003), and by avidity maturation of its islet-associated counterpart (Amrani et al., 2000). More recently, it has been shown that islet-associated CD8+ cells in NOD mice recognize multiple IGRP epitopes, indicating that IGRP is a dominant autoantigen for CD8+ cells, at least in murine T1D (Han et al., 2005). NOD islet-associated CD8+ cells, particularly those found early on in the disease process also recognize an insulin epitope (Ins B$_{15-23}$ (Wong et al., 1999)).

Association studies have suggested that certain HLA class I alleles (i.e., HLA-A*0201) afford susceptibility to human T1D (Fennessy et al., 1994; Honeyman et al., 1995; Tait et al., 1995; Nejentsev et al., 1997; Nakanishi et al., 1999; Robles et al., 2002). Pathology studies have shown that the insulitis lesions of newly diagnosed patients consist mostly of (HLA class I-restricted) CD8+ T-cells (Bottazzo et al., 1985; Atkinson and Maclaren, 1990; Castano and Eisenbarth, 1990; Hanninen et al., 1992; Itoh et al., 1993; Somoza et al., 1994; Atkinson and Maclaren, 1994; Moriwaki et al., 1999; Imagawa et al., 2001), which are also the predominant cell population in patients treated by transplantation with pancreas isografts (from identical twins) or allografts (from related donors) (Sibley et al., 1985; Santamaria et al., 1992).

Insulin is a key target of the antibody and CD4+ response in both human and murine T1D (Wong et al., 1999; Palmer et al., 1983; Chentoufi and Polychronakos, 2002; Toma et al., 2005; Nakayama et al., 2005; Kent et al., 2005). The human insulin B chain epitope hInsB$_{10-18}$ is presented by HLA-A*0201 to autoreactive CD8+ cells both in islet transplant recipients (Pinkse et al., 2005) and in the course of spontaneous disease (Toma et al., 2005). In addition, four additional peptides have been identified from mouse pre-proinsulin 1 or 2 that are recognized by islet-associated CD8+ T-cells from HLA-A*0201-transgenic mice in the context of HLA-A*0201.

IGRP, which is encoded by a gene (located on chromosome 2q28-32 (Martin et al., 2001)) that overlaps a T1D susceptibility locus, IDDM7 (2q31) (Pociot and McDermott, 2002; Owerbach, 2000), has also been recently identified as a beta-cell autoantigen of potential relevance in human T1D (Takaki et al., 2006). Two HLA-A*0201-binding epitopes of human IGRP (hIGRP$_{228-236}$ and hIGRP$_{265-273}$) are recognized by islet-associated CD8+ cells from murine MHC class I-deficient NOD mice expressing an HLA-A*0201 transgene (Takaki et al., 2006). Notably, the islet-associated CD8+ T-cells of these 'humanized' HLA-A*0201-transgenic mice were cytotoxic to HLA-A*0201-positive human islets (Takaki et al., 2006).

T1D in NOD mice can be prevented by expansion of low avidity autoreactive CD8+ T-cells. Administration of soluble peptides (without adjuvant) is an effective way of inducing antigen-specific T-cell tolerance (Aichele et al., 1994; Toes et al., 1996). Previously, it was shown that treatment of prediabetic NOD mice with soluble NRP-A7 blunted avidity maturation of the IGRP$_{206-214}$-reactive CD8+ subset by selectively deleting clonotypes expressing TCRs with the highest affinity for peptide/MHC (Amrani et al., 2000). These observations raised the possibility that NRP-A7's anti-T1D activity was mediated also by fostering occupation of the 'high avidity clonotype niche' (emptied by NRP-A7 treatment) by 'low avidity' (and potentially anti-diabetogenic) clones. To test this hypothesis, altered peptide ligands (APLs) were identified with partial, full or super agonistic activity for IGRP$_{206-214}$-reactive CD8+ T-cells and compared their anti-T1D activity over a wide dose-range.

Chronic treatment with moderate doses of an intermediate affinity APL (NRP-A7) or high doses of a low affinity APL (NRP-I4) afforded T1D protection. This was associated with local accumulation of low avidity IGRP$_{206-214}$-reactive CD8+ cells at the expense of their high avidity counterparts, which were deleted. Unexpectedly, chronic treatment with high doses of a high affinity APL (NRP-V7) or the natural ligand (IGRP$_{206-214}$) only afforded marginal protection. Strikingly, the islets of these mice contained almost no IGRP$_{206-214}$-reactive CD8+ cells, but increased populations of CD8+ cells recognizing other IGRP epitopes. This led us to conclude that peptide therapy in autoimmunity may be most effective when it fosters occupation of the target organ lymphocyte niche by non-pathogenic, low avidity clones (Han et al., 2005), a prediction supported by mathematical modeling (Maree et al., 2006). Unfortunately, this outcome occurred only within a narrow range of APL dose and avidity (for target TCRs), suggesting that peptide therapy is ill-suited to prevent or cure T1D.

Thus, there remains a need for additional compositions and related methods for the treatment of diabetes, as well as other autoimmune disorders.

SUMMARY OF THE INVENTION

It would be difficult to treat a patient with peptides because, as is the case of IGRP, this would require several milligrams of peptides per dose. Delivery of antigen/MHC complexes, e.g., peptide/MHC/particle complexes (without costimulatory molecules), on particles were contemplated. These complexes, it turns out, are more tolerogenic than peptides alone.

Aspects and embodiments of this application include the discovery of a new paradigm in the treatment of autoimmunity. Traditionally, vaccines have been used to expand T-cells capable of affording protection against pathogens or cancer, or to delete T-cells capable of causing autoimmunity. Aspects of the present invention relate to a novel type of 'vaccine' that selectively induces the expansion of autoreactive CD8+ cells with anti-autoimmune properties and, at the same time, the deletion of autoreactive CD8+ cells with pathogenic (autoimmune) properties, both according to the antigenic specificity of the T cells. The anti-autoimmune autoreactive CD8+ T-cells (anti-pathogenic CD8+ cells) suppress autoreactive T-cell responses in a tissue-specific (upon spontaneous recruitment to the target tissue) but antigen-non-specific manner (e.g., locally suppressing other autoreactive T-cell responses). As a result, treatment with this type of vaccine can both prevent and/or ameliorate T1D, as well as restore normoglycemia or reduce glucose levels in hyperglycemic NOD mice without causing generalized immunosuppression. This strategy can be applicable to the treatment of other T-cell mediated autoimmune diseases and may be able to prevent T1D recurrence upon islet transplantation.

Certain embodiments of the present invention relate to methods of selectively reducing or expanding T cells according to the antigenic specificity of the T cells. Therefore, the present invention can be used to reduce or eliminate T cells that recognize autoantigens, such as P cell specific T cells. As such, the present invention can be used to prevent, treat, or ameliorate autoimmune diseases such as IDDM. Furthermore, the present invention can be used to expand desirable T cells, such as T cells that recognize tumor antigens, to prevent, treat and/or ameliorate diseases battled by these T cells.

Embodiments of the invention are directed to methods of diagnosing, preventing, or treating an autoimmune disorder comprising administering an antigen/MHC/particle complex to a subject in an amount sufficient to expand non-pathogenic or anti-pathogenic autoreactive T cells. An antigen includes, but is not limited to all or part of a peptide, nucleic acid, carbohydrate, lipid or other molecule or compound that can modulate the activity of T cells or T cell populations, when in the context of a MHC or MHC like molecule coupled to a substrate.

Embodiments of the invention include tolerogenic particles comprising a microparticle or nanoparticle coupled to an antigen-MHC complex. The antigen-MHC complex may be coupled directly to a particle or via a linker. A microparticle or nanoparticle can comprise various layers which in turn may comprise multiple components (e.g., a metal core with a covering or shell of other molecules that can be more easily coupled to the antigen-MHC complex (e.g, streptavidin or avidin or other know molecules used to attach moieties to nanoparticles). In certain aspects, a microparticle or nanoparticle comprises a material selected from the group consisting of cadmium selenide, titanium, titanium dioxide, tin, tin oxide, silicon, silicon dioxide iron, iron III oxide, silver, nickel, gold, copper, aluminum, steel, cobalt-chrome alloy, titanium alloy, brushite, tricalcium phosphate, alumina, silica, zirconia, diamond, polystyrene, silicone rubber, polycarbonate, polyurethanes, polypropylenes, polymethylmethaacrylate, polyvinyl chloride, polyesters, polyethers, and polyethylene. In further aspects, a microparticle or nanoparticle is a metal or magentizable or superparamagnetic particle. Metal nanoparticles can be formed from Au, Pt, Pd, Cu, Ag, Co, Fe, Ni, Mn, Sm, Nd, Pr, Gd, Ti, Zr, Si, and In precursors, their binary alloys, their ternary alloys and their intermetallic compounds. See U.S. Pat. Nos. 7,332,586, 7,326,399, 7,326,399, 7,060,121, 6,929,675, 6,846,474, 6,712,997, 6,688,494, which are incorporated herein by reference in their entirety, for a discussion of compositions and methods related to the production of microparticles or nanoparticles.

Certain aspects of the invention include methods and compositions concerning antigenic compositions including segments, fragments, or epitopes of polypeptides, peptides, nucleic acids, carbohydrates, lipids and other molecules that provoke or induce an antigenic or immune response, generally referred to as antigens. In particular aspects, the antigen is derived from, is a mimic of, or is an autoreactive antigen and/or complexes thereof.

Peptide antigens include, but are not limited to hInsB$_{10-18}$ (HLVEALYLV (SEQ ID NO:1)), hIGRP$_{228-236}$ (LNIDLL-WSV (SEQ ID NO:2)), hIGRP$_{265-273}$ (VLFGLGFAI (SEQ ID NO:3)), IGRP$_{206-214}$ (VYLKTNVFL (SEQ ID NO:4)), NRP-A7 (KYNKANAFL (SEQ ID NO:6)), NRP-14 (KYNIANVFL (SEQ ID NO:7)), NRP-V7 (KYNKANVFL (SEQ ID NO:8)), YAI/D$^b$ (FQDENYLYL (SEQ ID NO:9)) and/or INS B$_{15-23}$ (LYLVCGERG (SEQ ID NO:10)), as well as peptides and proteins disclosed in U.S. Publication 20050202032, which is incorporated herein by reference in its entirety.

In certain aspects, a peptide antigen for treatment of T1D is GAD65$_{114\text{-}123}$, VMNILLQYVV (SEQ ID NO:14); GAD65$_{536\text{-}545}$, RMMEYGTTMV (SEQ ID NO:15); GFAP$_{143\text{-}151}$, NLAQTDLATV (SEQ ID NO:16); GFAP$_{214\text{-}222}$, QLARQQVHV (SEQ ID NO:17); IA-2$_{172\text{-}180}$, SLSPLQAEL (SEQ ID NO:18); IA-2$_{482\text{-}490}$, SLAAGVKLL (SEQ ID NO:19); IA-2$_{805\text{-}813}$, VIVMLTPLV (SEQ ID NO:20); ppIAPPs5i$_3$, KLQVFLIVL (SEQ ID NO:21); ppI-APP$_{9\text{-}17}$, FLIVLSVAL (SEQ ID NO:22); IGRP$_{152\text{-}160}$, FLWSVFMLI (SEQ ID NO:23); IGRP$_{211\text{-}219}$, NLFLFLFAV (SEQ ID NO:24); IGRP$_{215\text{-}223}$, FLFAVGFYL (SEQ ID NO:25); IGRP$_{222\text{-}230}$, YLLLRVLNI (SEQ ID NO:26); IGRP$_{228\text{-}236}$, LNIDLLWSV (SEQ ID NO:2); IGRP$_{265\text{-}273}$, VLFGLGFAI (SEQ ID NO:3); IGRP$_{293\text{-}301}$, RLLCALTSL (SEQ ID NO:27); Pro-insulin$_{L2\text{-}10}$, ALWMRLLPL (SEQ ID NO:28); Pro-insulin$_{L3\text{-}11}$, LWMRLLPLL (SEQ ID NO:29); Pro-insulin$_{L6\text{-}14}$, RLLPLLALL (SEQ ID NO:30); Pro-insulin$_{B5\text{-}14}$, HLCGSHLVEA (SEQ ID NO:31); Pro-insulin$_{B10\text{-}18}$, HLVEALYLV (SEQ ID NO:1); Pro-insulin$_{B14\text{-}22}$, ALYLVCGER (SEQ ID NO:32); Pro-insulin$_{B15\text{-}24}$, LYLVCGERGF (SEQ ID NO:33); Pro-insulin$_{B17\text{-}25}$, LVCGERGFF (SEQ ID NO:34); Pro-insulin$_{B18\text{-}27}$, VCGERGFFYT (SEQ ID NO:35); Pro-insulin$_{B20\text{-}27}$, GERGFFYT (SEQ ID NO:36); Pro-insulin$_{B21\text{-}29}$, ERGFFYTPK (SEQ ID NO:37); Pro-insulin$_{B25\text{-}C1}$, FYTPK-TRRE (SEQ ID NO:38); Pro-insulin$_{B27\text{-}C5}$, TPKTRRE-AEDL (SEQ ID NO:39); Pro-insulin$_{C20\text{-}28}$, SLQPLALEG (SEQ ID NO:40); Pro-insulin$_{C25\text{-}33}$, ALEGSLQKR (SEQ ID NO:41); Pro-insulin$_{C29\text{-}A5}$, SLQKRGIVEQ (SEQ ID NO:42); Pro-insulin$_{A1\text{-}10}$, GIVEQCCTSI (SEQ ID NO:43); Pro-insulin$_{A2\text{-}10}$, IVEQCCTSI (SEQ ID NO:44); Pro-insulin$_{A12\text{-}20}$, SLYQLENYC (SEQ ID NO:45) or combinations thereof.

In still further aspects peptide antigens associated with multiple sclerosis (MS) can be used and include: MAG$_{287\text{-}295}$, SLLLELEEV (SEQ ID NO:46); MAG$_{509\text{-}517}$, LMWAKIGPV (SEQ ID NO:47); MAG$_{556\text{-}564}$, VLFSSDFR1 (SEQ ID NO:48); MBPI$_{110\text{-}118}$, SLSRFSWGA (SEQ ID NO:49); MOG$_{114\text{-}122}$, KVEDPFYWV (SEQ ID NO:50); MOG$_{166\text{-}175}$, RTFDPHFLRV (SEQ ID NO:51); MOG$_{172\text{-}180}$, FLRVPCWKI (SEQ ID NO:52); MOG$_{179\text{-}188}$, KITLFVIVPV (SEQ ID NO:53); MOG$_{188\text{-}196}$, VLGPLVALI (SEQ ID NO:54); MOG$_{181\text{-}189}$, TLFVIVPVL (SEQ ID NO:55); MOG$_{205\text{-}214}$, RLAGQFLEEL (SEQ ID NO:56); PLP$_{80\text{-}88}$, FLYGALLLA (SEQ ID NO:57) or combinations thereof.

In certain aspects the antigen-MHC complex can be crosslinked to the microparticle or nanoparticle. One non-limiting method of conjugating a microparticle or nanoparticle to an antigen-MHC complex includes (a) reacting an antigen-MHC complex a crosslinking agent, thereby forming an antigen-MHC-crosslinking agent complex; and (b) reacting a microparticle or nanoparticle to the complex of step (a). In one embodiment, the method comprises concentrating the complex of step (a) before performing step (b). In another embodiment, the crosslinking agent comprises a heterobifunctional crosslinking agent. In yet another embodiment, the crosslinking agent comprises DOTA-maleimide (4-maleimidobutyramidobenzyl-DOTA), SMPT (4-succinimidyloxycarbonyl-α-methyl-α-(2-pyridylditio)toluene-), sulfo-LC-SMPT (sulfosuccinimidyl-6-(α-methyl-α-(2-pyridylthio)toluamido) hexanoate, Traut's reagent (2-Iminothiolane-HCl), or any combination thereof. See U.S. Patent Publication 20070059775; U.S. Pat. Nos. 4,671,958, 4,659,839, 4,414,148, 4,699,784; 4,680,338; 4,569,789; 4,589,071; 7,186,814 and 5,543,391 European Patent Application No. 188,256 for a discussion of conjugating complexes to microparticles or nanoparticles.

An autoimmune disorder may include, but is not limited to, diabetes melitus, transplantation rejection, multiple sclerosis, premature ovarian failure, scleroderm, Sjogren's disease, lupus, vilelego, alopecia (baldness), polyglandular failure, Grave's disease, hypothyroidism, polymyositis, pemphigus, Crohn's disease, colititis, autoimmune hepatitis, hypopituitarism, myocardititis, Addison's disease, autoimmune skin diseases, uveititis, pernicious anemia, hypoparathyroidism, and/or rheumatoid arthritis. In certain aspects, a peptide component of an antigen/MHC/particle complex is derived or designed from an autoantigen or an autoantigen epitope, or a mimic thereof, involved in the autoimmune response to be probed, modulated, or blunted by the treatment. In particular aspects, the autoantigen is a peptide, carbohydrate, or lipid. In certain aspects, an autoantigen is an fragment, epitope, or peptide of a protein, carbohydrate, or lipid expressed by certain cells of a subject, such as pancreatic beta cells, and include, but is not limited to a fragment of IGRP, Insulin, GAD or IA-2 protein. Various such proteins or epitopes have been identified for a variety of autoimmune conditions. The autoantigen may be a peptide, carbohydrate, lipid or the like derived from a second endocrine or neurocrine component, such as peri-islet Schwann cell or the like.

In still further aspects of this invention, the MHC component of the antigen/MHC/particle complex is a classical or non-classical MHC class I or MHC class II polypeptide component. The MHC class I component can comprise all or part of a HLA-A, HLA-B, HLA-C, HLA-E, HLA-F, HLA-G molecule, particularly all or part of a HLA-A molecule, such as a HLA-A*0201 MHC class I molecule. The non-classical MHC class I component can comprise CD1-like molecules. An MHC class II component may comprise all or part of a HLA-DR, HLA-DQ, or HLA-DP. In certain aspects, the antigen/MHC complex is covalently or non-covalently coupled or attached to a substrate (antigen/MHC/particle complex). The substrate is typically a microparticle or nanoparticle. In particular, the particle comprises a metal, such as iron or iron oxide. Peptides of the invention can be chemically coupled to a substrate and in particular coupled via a chemical or a peptide linker. CD1 molecules are an example of a non-classical MHC molecules. Non-classical MHC molecules are characterized as non-polymorphic, conserved among species and possessing narrow, deep, hydrophobic ligand binding pockets. These binding pockets are capable of presenting glycolipids and phospholipids to Natural Killer T (NKT) cells. NKT cells represent a unique lymphocyte population that co-express NK cell markers and a semi-invariant T cell receptor (TCR). They are implicated in the regulation of immune responses associated with a broad range of diseases.

In certain embodiments, the T cells expanded by the treatment have been pre-activated by the disease process and have a memory phenotype. In one aspect, T cells arise from autoreactive precursors recognizing the target epitope with low avidity. Avidity can be determined by a tetramer binding assay or the like. In a further aspect, the antigen/MHC/particle complex is administered prior, after or both prior to and after the onset of clinical symptoms of the autoimmune disease of interest. In still a further aspect, the method may include a step that comprises assessing a biological parameter of an autoimmune condition, such as the subjects blood sugar levels before and/or after treatment. The methods of the invention may also include assessing a subject's autoimmune status, including the assessment of any autoreactive immune responses. In certain aspects, a T cell is a CD4+ or CD8+ T cell or a NK T (NKT) cell.

Further embodiments of the invention include methods of expanding non-pathogenic or anti-pathogenic autoreactive T cells comprising administering an antigen/MHC/particle complex in an amount sufficient to stimulate expansion of a non-pathogenic or anti-pathogenic autoreactive T cell. In certain aspects the T cell is a CD8+ or a CD4+ T cell or a NKT cell.

In still further embodiments, the invention includes methods for protecting cells of a subject, such as a pancreatic islet cells, from an autoimmune response, particularly a pathogenic autoimmune response, comprising administering to a subject an antigen/MHC/particle complex in an amount sufficient to inhibit the destruction of the cells or tissues comprising the cells, wherein the antigen or antigenic molecule from which it is derived is from an autoantigen associated with cells.

In yet a further embodiment, the invention includes methods for diagnosing autoimmunity comprising assessing treatment-induced expansion of non-pathogenic or anti-pathogenic CD8+ or CD4+ T cell responses as an indication of active autoimmunity.

Embodiments of the invention may include methods for preventing, ameliorating, or treating rejection of transplanted tissues by allogeneic or autoimmune responses by administering an antigen/MHC complex operatively coupled to a substrate (i.e., an antigen/MHC/particle complex) to a subject in an amount sufficient to expand non-pathogenic or anti-pathogenic autoreactive T cells, or inducing expansion of non-pathogenic or anti-pathogenic cells recognizing alloantigens or autoantigens expressed by transplanted tissues or organs.

Embodiments of the invention provide methods of increasing or maintaining the number of functional cells, e.g., islet cells, of a predetermined type in a mammal by preventing cell death or killing. In certain embodiments, this method is used to treat an autoimmune disease where endogenous cell and/or tissue regeneration is desired. Such autoimmune diseases include, without limitation, diabetes melitus, multiple sclerosis, premature ovarian failure, scleroderm, Sjogren's disease, lupus, vitelego, alopecia (baldness), polyglandular failure, Grave's disease, hypothyroidism, polymyositits, pemphigus, Crohn's disease, colititis, autoimmune hepatitis, hypopituitarism, myocarditits, Addison's disease, autoimmune skin diseases, uveititis, pernicious anemia, hypoparathyroidism, rheumatoid arthritis and the like. One aspect of the invention provides a novel two-part therapeutic approach to ablate existing autoimmunity while re-educating the immune system.

An antigen/MHC/particle complex refers to presentation of a peptide, carbohydrate, lipid, or other antigenic segment, fragment, or epitope of an antigenic molecule or protein (i.e., self peptide or autoantigen) on a surface, such as a microparticle or nanoparticle. "Antigen" as used herein refers to all, part, fragment, or segment of a molecule that can induce an immune response in a subject or an expansion of non-pathogenic cells.

In certain aspects, the antigen/MHC/particle complex need not be administered with an adjuvant in order to induce an immune response, e.g., an antibody response. In particular embodiments, the antigen/MHC/particle composition can be used in conjunction with well known polyclonal and monoclonal antibody techniques to produce an antibody using reduced or no adjuvant(s).

By "killing" or "kills" it is meant to cause cell death by apoptosis or necrosis. Apoptosis or necrosis can be mediated by any cell death pathway.

"Autoimmune cells" include, for example, adult splenocytes, T lymphocytes, B lymphocytes, and cells of bone marrow origin, such as defective antigen presenting cells of a mammal, that have activity towards the organism from which the autoimmune cell is derived.

A "mimic" is an analog of a given ligand or peptide, wherein the analog is substantially similar to the ligand. "Substantially similar" means that the analog has a binding profile similar to the ligand except the mimic has one or more functional groups or modifications that collectively accounts for less than about 50%, less than about 40%, less than about 30%, or less than about 20%, of the molecular weight of the ligand.

An "effective amount" is an amount sufficient to achieve the intended purpose, e.g., modulation of T cell activity or T cell populations. As described herein in detail, the effective amount, or dosage, depends on the purpose and the antigen and can be determined according to the present disclosure.

An "auto-reactive T cell" is a T cell that recognizes an "auto-antigen", which is a molecule produced and contained by the same individual that contains the T cell.

A "pathogenic T cell" is a T cell that is harmful to a subject containing the T cell. Whereas, a non-pathogenic T cell is not substantially harmful to a subject, and an anti-pathogenic T cells reduces, ameliorates, inhibits, or negates the harm of a pathogenic T cell.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A, NRP-V7/$K^d$-np treatment expanded NRP-V7/$K^d$ tetramer+ cells within the CD8+ T cell population in the peripheral blood (n=4) and the islet-infiltrates. (n=11), compared to control-np treated animals (n=4 and 21 for blood and islet, respectively). FIG. 5B, The expanded tetramer+ T cells in the pancreatic islets bind peptide/MHC with low avidity. $K_d$=10.21±1.65 nM in the NRP-V7/$K^d$-np-treated animals, compared to $K_d$=4.42±0.87 nM in the control animals (n=5 and 12, respectively). FIG. 5C and FIG. 5D, The protective effect of NRP-V7/$K^d$ np is dose-dependent (FIG. 5C) and corresponds to the degree of expansion of NRP-V7/$K^d$ tetramer+ cells in the peripheral blood (FIG. 5D). Animals were injected with either full (7.5 μg per injection), ⅕ (1.5 μg per injection), or 1/20 (0.375 μg per injection) doses of np following identical injection schedules (as described above) (n=21, 12, and 13, respectively). FIG. 5E, The expansion of NRP-V7/$K^d$ tetramer+ CD8+ T cells is dependent on the number of injections (n=10). Ten-week-old NOD females were injected with 10 full doses of NRP-V7/$K^d$-np at two injections per week. The animals were bled after 4 and 10 injections, and the percentages of NRP-V7/$K^d$ tetramer+ cells in the blood were determined.

FIG. 6A and FIG. 6B, 17.4α/8.3β-NOD (FIG. 6A) or 17.6α/8.3β-NOD (FIG. 6B) mice were untreated or treated with a single injection of 10 full dose-equivalent of NRP-V7/$K^d$-np and sacrificed 20 hours later. Splenic CD8+, CD4+, CD11c+ and CD11b+ and B220+ cells were assessed for np binding based on MFI of the np-associated FITC fluorophore (n=1 for each strain). FIG. 6C, NOD mice were untreated or treated with two full doses of NRP-V7/$K^d$-np every week for the duration of 5 weeks, starting at 10 weeks of age, and sacrificed 20 hours after the last np injection. Splenic CD8+, CD4+, CD11c+ and CD11b+ cells were assessed for np binding based on MFI of the np-associated FITC fluorophore (n=2). Note that a small peak of fluorescently labeled cells appears exclusively in the CD8+ T-cell subset.

FIG. 7A, NOD mice treated with $DMK_{138-146}$/$D^b$-np following the same schedule as in FIG. 5 exhibit expansion of $DMK_{138-146}$/$D^b$ tetramer+ CD8+ T cells in the peripheral blood (n=11) and the islet infiltrates (n=13), compared to control animals (n=3). FIG. 7B, 72% of the $DMK_{138-146}$/$D^b$-np treated animals remained diabetes-free at 32 weeks of age (n=18). FIG. 7C and FIG. 7D, The expansion of tetramer+ CD8+ cells is antigen-specific. $DMK_{138-146}$/$D^b$-np treatment does not expand NRP-V7/$K^d$ tetramer+ cells (blood: n=4 and 11; islet: n=21 and 11) (FIG. 7C) and NRP-V7/$K^d$-np treatment does not expand $DMK^{138-146}$/$D^b$ tetramer+ cells (blood: n=3 and 4; islets: n=3 and 2) (FIG. 7D). FIG. 7E, Representative FACS profiles of peripheral blood CD8+ T-cells in nanoparticle-treated mice. Mice received one intravenous injection of nanoparticles once every 2-3 weeks, starting at 4 weeks of age. These samples are from mice at the end of treatment (~32 wk of age).

FIG. 9A, Survival of acutely diabetic NOD mice undergoing np treatments. Animals reaching or exceeding 10.5 mM of blood glucose are treated intravenously with TUM/$K^d$-np (n=9), NRP-V7/$K^d$-np (n=11), or $DMK_{138-146}$/$D^b$-np (n=11) twice weekly until the animals are considered consistently normoglycemic (with blood glucose level keeping under the 10.5 mM threshold for four consecutive weeks). FIG. 9B-FIG. 9D, Blood glucose curves of individual animals treated with NRP-V7/$K^d$-np (FIG. 9B), $DMK_{138-146}$/$D^b$-np (FIG. 9C) and TUM/$K^d$-np (FIG. 9D). FIG. 9E, Average blood glucose levels of each treatment group computed over the duration of the treatment regime. FIG. 9F, Blood glucose curves of individual animals treated with 20 μg/day of anti-CD3 MAb (clone 2C11) for 5 consecutive days.

FIG. 10A, The accumulation and decline of tetramer+ cells in peripheral blood at different time points after the withdrawal of np treatment. Both NRP-V7/$K^d$-np and $DMK_{138-146}$/$D^b$-np-treated animals displayed progressive loss of their respective tetramer+ CD8+ T cell population in the periphery after treatment withdrawal. FIG. 10B, Diabetes recurrence in cured NOD mice after treatment withdrawal. Animals withdrawn from treatments were monitored for diabetes until at least 50 weeks of age. FIG. 10C, Blood glucose curves of individual NRP-V7/$K^d$-np-treated and cured animals after withdrawal of treatment. FIG. 10D, Blood glucose curves of individual $DMK_{138-146}$/$D^b$-np-treated and cured animals after withdrawal of treatment.

FIG. 11A, IPGTT of acutely diabetic, cured animals compared to untreated controls at 50 weeks of age (top: IPGTT glucose curves; bottom: area under curve analysis; diabetic untreated n=7; non-diabetic untreated n=5; NRP-V7/$K^d$-np-treated n=4; DMK$_{138-146}$/D$^b$-np-treated n=5). FIG. 11B, Postprandial serum insulin levels of NRP-V7/K$^d$-np-treated mice versus diabetic and non-diabetic untreated controls (n=7, 9, and 7, respectively). FIG. 11C, IPGTT serum insulin levels of NRP-V7/K$^d$-np- and DMK$_{138-146}$/D$^b$-np-treated mice vs. diabetic and non-diabetic untreated controls (n 4, 7, and 5). FIG. 11D, Body weights of NRP-V7/K$^d$-np-treated (n=5) and untreated (n=6) animals at 50 weeks of age.

FIG. 13A, Frequency of diabetes in 17.6α/8.3β-NOD (n=95) versus 17.4α/8.3β-NOD mice (n=598). FIG. 13B, Insulitis score in Tg mice (n=6 for 17.6α/8.3β-NOD, n=3 for 17.4α/8.3β-NOD). FIG. 13C, Frequency of diabetes in NOD (n=56) versus LCMV-NOD (n=10).

FIG. 14A, Developmental biology of 17.6α/8.3β versus 17.4α/8.3β TCR in Tg mice. Upper panels are representative CD4 versus CD8 dot plots of splenocytes. Lower panel is the comparison of CD8+ T cell staining with NRP-V7/K$^d$ tetramer. FIG. 14B, Developmental biology of the 17.6α/8.30β versus 17.4α/8.3β TCRs in RAG-2-/- Tg mice. Upper panels are representative CD4 versus CD8 dot plots of splenocytes. Lower panel is the comparison of CD8+ T cell staining with NRP-V7/K$^d$ tetramer.

FIG. 16A, Upper panels are representative CD4 versus CD8 dot plots of splenocytes. Lower panel is the comparison of CD8+ T cell staining with NRP-V7/K$^d$ tetramer. FIG. 16B, Frequency of diabetes in 17.6α/8.3β-NOD.TCRα-/- (n=14) versus 17.4α/8.3β-NOD.TCRα-/- mice (n=28). Values in the dot plot FACS panels correspond to the percentages of the cells within each quadrant and values in the histogram panels correspond the percentages of the cells that stained positive (mean±SE).

FIG. 17A, Representative FACS profiles of splenic CD8+ T cells from 17.6α/8.3β-NOD.TCRα-/- versus 17.4α/8.3β-NOD.TCRα-/- mice. FIG. 17B, Percentage of CD44$^{hi}$ CD122$^+$ CD8+ T cells within spleen (n=12 for 17.6α/8.3β-NOD.TCRα-/- and n=9 for 17.4α/8.30β-NOD.TCRα-/-), PLN (n=9 for 17.6α/8.3β-NOD.TCRα-/- and n=6 for 17.4α/8.3β-NOD.TCRα-/-) and BM (n=4 for 17.6α/8.3β-NOD.TCRα-/- and n=3 for 17.4α/8.3β-NOD.TCRα-/-) of TCRα-/- Tg mice (mean±SE). Mice were 9-18 weeks old. FIG. 17C, Representative FACS profile of splenic CD8+ T cells from 17.6α/8.30β-NOD.TCRα-/- mice stained with NRP-V7/K$^d$ tetramer versus anti-CD 122 Ab. Values are mean±SE of five different experiments. FIG. 17D, Phenotypic analysis of naïve versus memory splenic CD8+ T cells from 17.6α/8.3β-NOD.TCRα-/- mice. Data are representative of at least two experiments for each marker. FIG. 17E, Comparison of CD122 staining in CD8+CD4− thymocytes versus CD8+ splenocytes from TCRα-/- Tg mice. Data are representative of four experiments. FIG. 17F, BrdU uptake by splenic CD8+ T cell from TCRα-/- Tg mice. FIG. 17G, Upper panel: representative FACS profile of the proliferation of splenic CD8+ T cell from Tg mice in response to cytokines IL-2 and IL-15 (both at 100 ng/ml). Lower panel: Fold expansion of naïve versus memory CD8+ T cells from 17.6α/8.30β-NOD.TCRα-/- mice in response to different concentration of IL-2 and IL-15. Data are representative of at least three experiments. FIG. 17H, Production of IFN-γ by splenic naïve CD8+ T cells from 17.4α/8.3β-NOD.TCRα-/- mice versus naïve and memory CD8+ T cells from 17.6α/8.3β-NOD.TCRα-/- mice in response to DCs pulsed with 1 μg/ml NRP-A7 after 24 and 48 hours. FIG. 17I, Intra-cellular IFN-γ staining from splenic naïve CD8+ T cells from 17.4α/8.3β-NOD.TCRα-/- mice versus naïve and memory CD8+ T cells from 17.6α/8.3β-NOD.TCRα-/- mice in response to DCs pulsed with 1 μg/ml NRP-A7 after 6 hours. FIG. 17J, Production of IL-2 and proliferation in response to DCs pulsed with 1 μg/ml NRP-A7 at different time-points. Data in FIG. 17H and FIG. 17J are representative of four experiments and data in FIG. 17I are representative of three experiments.

FIG. 19A, In vitro cytotoxicity of freshly isolated naive CD8+ T cells from 17.4α/8.30β-NOD.TCRα-/- mice versus naïve and memory CD8+ T cells from 17.6α/8.30β-NOD.TCRα-/- mice against NRP-A7 and TUM-pulsed BM DCs. Data are representative of three experiments. Purified BM DCs were pulsed with 1 μg/ml NRP-A7 or TUM and labeled with [$^{51}$Cr]-sodium chromate. Effector:target ratio=8:1 (40000 effectors:5000 target cells). Supernatant was harvested after 8 hours. FIG. 19B, In vivo cytotoxicity assay: NRP-A7-pulsed (CFSE$^{lo}$) or TUM-pulsed (CFSE$^{hi}$) B-cell (upper panels) or freshly isolated splenic and LN DCs (lower panels) were injected into Tg hosts at 1:1 ratio. B cells or fresh DCs (from spleen and LNs) were isolated using anti-B220 or anti-CD11c MACS beads, pulsed with 10 μg/ml of peptides for 2 hours, washed, labeled with CFSE (TUM: 3 μM CFSE, NRP-A7: 0.3 μM CFSE) for 3 mins at 37° C., washed 3 times and 4-5×10$^6$ cells from each population were injected into the hosts. After 18 hours mice were sacrificed and splenocytes were FACS analyzed.

FIG. 20A, The expanded NRP-V7/K$^d$ tetramer+ CD8+ cells express high levels of CD44; a subset of these also express CD122 (n=7 and 4 for control vs. NRP-V7/K$^d$-np). FIG. 20B, The expanded tetramer+ cells secrete IFNγ but not IL-2 in response to antigenic stimulation. NRP-V7/K$^d$ tetramer-positive and negative CD8+ splenocytes were sorted, and 20,000 sorted cells were cultured with 10000 of BM-derived dendritic cells in the presence of 1 μg/mL NRP-V7 peptide. Culture supernatants were collected at 24 hours, and [$^3$H]-thymidine incorporation from 24 to 48 hours was measured. FIG. 20C, In vitro suppression of 17.4α/8.3β-CD8+ T cell proliferation by np-expanded NRP-V7/K$^d$ or DMK$_{138-146}$/D$^b$ tetramer+ CD8+ T cells. NRP-V7/K$^d$ or DMK$_{138-146}$/D$^b$ tetramer+ or −CD8+ T cells were sorted by FACS and either pre-activated with plate-bound anti-CD3 MAb or cultured directly with NRP-V7 or NRP-V7/DMK$_{138-146}$ peptide-pulsed BMDCs overnight. CFSE-labeled 17.4α/8.3β-CD8+ reporter T cells were added to the co-culture at a ratio of one suppressor to one reporter, and the CFSE-dilution was assessed 48 hours later. Shown are representative profiles of 3 experiments. FIG. 20D, Summary of the in vitro suppression experiments shown in FIG. 20C.

FIG. 21A, TUM/$K^d$-np does not expand TUM/$K^d$ tetramer+ cells (n=7 and 9, in spleen). FIG. 21B, NRP-V7/$K^d$-np does not expand NRP-V7/$K^d$ tetramer+ cells in the spleen, pancreatic lymph nodes, bone marrow, and peripheral blood of diabetes-resistant B10.H-$2^{g7}$ mice. 10 week-old H-$2^{g7}$ mice were injected twice per week with full doses of NRP-V7/$K^d$-np for 5 consecutive weeks, and the frequency of tetramer+ cells were determined (NRP-V7/$K^d$-np-treated n 4, control n=5). FIG. 21C, The expansion of NRP-V7/$K^d$ tetramer+ cells by np treatment is most efficient at diabetes onset. Here, the percentages of tetramer+ cells in the peripheral blood of animals that received 10 full doses of NRP-V7/$K^d$-np starting at 4 weeks of age (n=9), 10 weeks of age (n=10), or at diabetes onset (n=3) are compared.

FIG. 22A, Schematic diagram of the NOD.IGRP$_{K209A/F213A}^{K1/K1}$ construct. FIG. 22A discloses SEQ ID NOS 58 and 4, respectively, in order of appearance. FIG. 22B, IFNγ responses by islet-associated CD8+ T-cells to each IGRP epitope in two different NOD.IGRP$_{K209A/F213A}^{K1/K1}$ mice. FIG. 22C, Lack of expansion of NRP-V7/$K^d$ tetramer+ CD8+ cells in NRP-V7/$K^d$-np-treated NOD.IGRP$_{K209A/F213A}^{K1/K1}$ mice (n=8) in the spleen, bone marrow, pancreatic lymph nodes, and peripheral blood.

DETAILED DESCRIPTION OF THE INVENTION

Figures 1A, 1B, 1C:
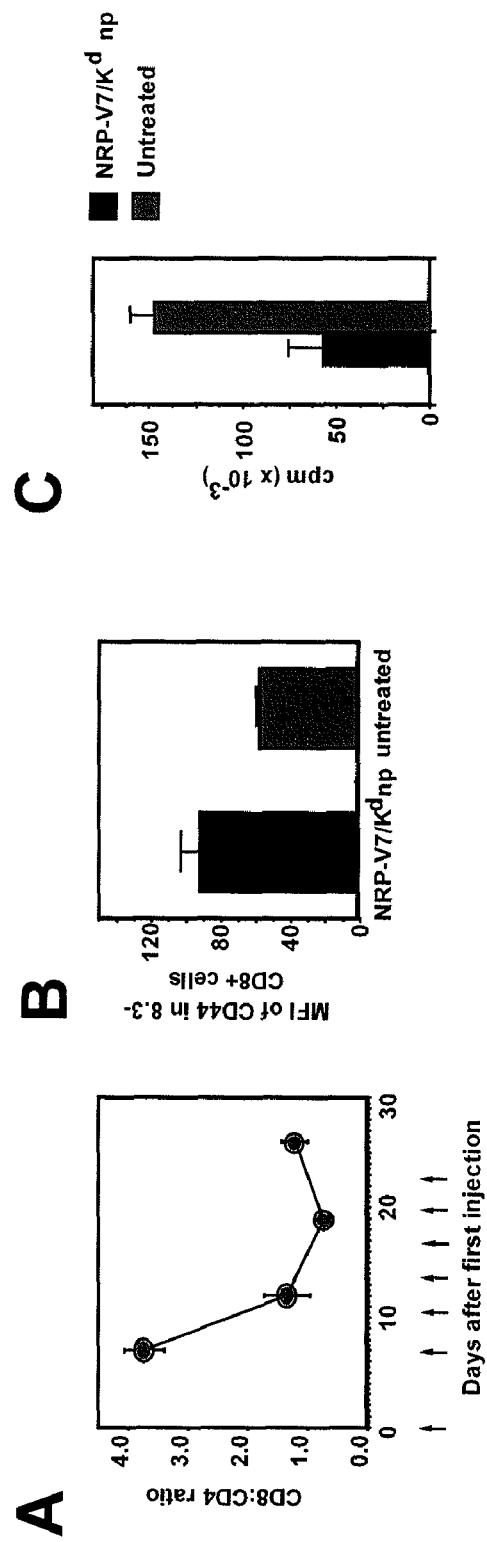
FIGS. 1A-C. Tolerogenic properties of solid-bound peptide/MHC complexes. Intravenous injections of solid-bound peptide/MHC complexes into 8.3-NOD mice induces T-cell deletion (FIG. 1A), and renders non-deleted antigen-activated (FIG. 1B) CD8+ T-cells hyporesponsive to antigen stimulation ex-vivo (FIG. 1C).

Observations to date (Han et al., 2005) suggested that, to be effective in autoimmunity, peptide therapy would have to target multiple epitope specificities. The inventors reasoned that it would be highly impractical to accomplish this with peptides because, in the case of IGRP alone, this would require several milligrams of peptides per dose. Because peptides are much more tolerogenic (i.e., at lower amounts) when bound to MHC molecules on fixed APCs (Miller et al., 1979), it was contemplated that systemic delivery of antigen/MHC complexes, e.g., peptide/MHC complexes (without costimulatory molecules) on particles might be more tolerogenic than peptides alone. This thought evolved from the availability of a reagent initially conceived to image islet inflammation. The inventors sought to specifically deliver a probe amenable to magnetic resonance (MR) imaging to circulating 8.3-like CD8+ T-cells (iron oxide nanoparticles coated with NRP-V7/$K^d$ complexes) (Moore et al., 2004). In particular, the inventors contemplated coating these particles with several different antigen/MHC complexes as a way to induce the simultaneous deletion of multiple T-cell specificities below the threshold required for T1D development. One feature of using these nanoparticles for tolerance induction was that their prototype was approved for use in humans for MRI studies.

Surprisingly, the inventors found that nanoparticles coated with antigen/MHC complexes (antigen/MHC/particle complex) expanded, efficiently, consistently, and at very low doses (corresponding to ~0.6 μg of peptide), the type of low-avidity autoreactive CD8+ cells that afforded T1D protection in APL-treated mice (Han et al., 2005; Maree et al., 2006). Another striking observation was that these nanoparticles appear to expand pre-existing pools of memory autoreactive CD8+ T-cells (i.e., they do not induce memory T cells de novo). These pre-existing pools are predominantly (if not exclusively) comprised of low avidity (non-pathogenic/anti-pathogenic) autoreactive CD8+ clonotypes. The high-avidity counterparts of these T-cells (with pathogenic activity) do not survive in vivo as memory cells, possibly, but not limiting the invention to any particular theory, because they undergo activation-induced cell death upon chronic exposure to their endogenous target beta cell autoantigen. Another unexpected observation was that these particles need not have to target a prevalent population of autoreactive CD8+ T-cells to be effective: similar results were obtained with nanoparticles coated with a subdominant peptide/MHC complex. In addition, this technology does not require the design of APLs of defined avidity (unlike the case with peptides), and thus has the potential to accommodate any target antigen or peptide/MHC target. One of the various attributes of this technology is that it can restore normoglycemia in NOD mice with newly diagnosed T1D, at rates that are at least comparable, if not better, than those obtained with anti-CD3 mAb treatment, a non-antigen-specific approach that has shown some promise in clinical trials (Herold et al., 2002; Keymeulen et al., 2005).

The inventors have produced autoantigen/MHC complexes that, when delivered bound to iron oxide particles, expand, efficiently, consistently, and at very low doses (corresponding to ~0.6 μg of peptide), a type of CD8+ cells that afforded protection against an autoimmune condition. The compositions of the invention can be used to expand pre-existing pools of memory autoreactive CD8+ T-cells (i.e., they do not appear to be able to induce memory T cells de novo). These pre-existing pools are predominantly (if not exclusively) comprised of low avidity (non-pathogenic/anti-pathogenic) autoreactive CD8+ clonotypes. The high-avidity counterparts of these T-cells (with pathogenic activity) do not survive in vivo as memory cells and predominantly exist as naïve T cells. Naïve T cells undergo cell death upon engaging autoantigen/MHC/particle complexes in the absence of costimulation and so the invention both deletes naïve pathogenic T cells and expands anti-diabetogenic memory T cells. The compositions described need not target a prevalent population of autoreactive CD8+ T-cells to be effective. In certain embodiments, the compositions and methods can be used to induce autoreactive T cell tolerance.

I. Pharmaceutical Compositions and Administration

The present invention includes methods for preventing or ameliorating an autoreactive condition. As such, the invention contemplates "vaccines" or immune system modifiers for use in various embodiments. Compositions proposed to be suitable for use as a vaccine may be prepared from autoreactive molecules including autoreactive proteins and their fragments. The invention includes compositions that can be used to induce or modify an immune response against an autoreactive antigen, e.g., a polypeptide, a peptide, a carbohydrate, a lipid or other molecule or molecular fragment and against developing a condition or disease caused by such an autoimmune response.

Compositions of the invention may be conventionally administered parenterally, by injection, for example, intravenously, subcutaneously, or intramuscularly. Additional formulations which are suitable for other modes of administration include oral formulations. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

Typically, compositions of the invention are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner. However, suitable dosage ranges are of the order of ten to several hundred nanograms or micrograms antigen/MHC/particle complex per administration. Suitable regimes for initial administration and boosters are also variable, but are typified by an initial administration followed by subsequent administrations.

The manner of application may be varied widely. Any of the conventional methods for administration of a vaccine are applicable. These are believed to include oral application on a solid physiologically acceptable base or in a physiologically acceptable dispersion, parenterally, by injection and the like. The dosage of the antigen/MHC/particle complex will depend on the route of administration and will vary according to the size and health of the subject.

In many instances, it will be desirable to have multiple administrations of a peptide/HC/particle complex, about, at most about or at least about 3, 4, 5, 6, 7, 8, 9, 10 or more. The administrations will normally range from 2 day to twelve week intervals, more usually from one to two week intervals. Periodic boosters at intervals of 0.5-5 years, usually two years, will be desirable to maintain the condition of the immune system. The course of the administrations may be followed by assays for autoreactive immune responses and T cell activity.

A. Combination Therapy

The compositions and related methods of the present invention, particularly administration of a antigen/MHC/particle complex, may also be used in combination with the administration of traditional therapies. These include, but are not limited to, the administration of immunosuppressive or modulating therapies or treatments.

In one aspect, it is contemplated that a antigen/MHC/particle complex is used in conjunction with a cytokine treatment. Alternatively, antigen/MHC/particle complex administration may precede or follow the other treatment by intervals ranging from minutes to weeks. In embodiments where the other agents and/or antigen/MHC/particle complexes are administered separately, one would generally ensure that a significant period of time did not expire between the time of each delivery, such that the agent and antigen/MHC/particle complex would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations may be employed, for example antigen/MHC/particle complex administration is "A" and the additional agent is "B":

```
A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  B/A/B/A  B/A/A/B  A/A/A/B  B/A/A/A  A/B/A/A

A/A/B/A
```

Administration of the peptide-MHC complex compositions of the present invention to a patient/subject will follow general protocols for the administration of such compounds, taking into account the toxicity, if any. It is expected that the treatment cycles would be repeated as necessary. It also is contemplated that various standard therapies, such as hydration, may be applied in combination with the described therapy.

B. Pharmaceutical Compositions

In some embodiments, pharmaceutical compositions are administered to a subject. Different aspects of the present invention involve administering an effective amount of a antigen/MHC/particle complex composition to a subject. Additionally, such compositions can be administered in combination with modifiers of the immune system. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The active compounds of the present invention can be formulated for parenteral administration, e.g., formulated for injection via the intravenous, intramuscular, sub-cutaneous, or even intraperitoneal routes. The preparation of an aqueous composition that contains a antigen/MHC/particle complex that modifies the subject's immune condition will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference).

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

C. In Vitro or Ex Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects of the present invention, the compositions may be administered either in vitro, ex vivo, or in vivo. In certain in vitro embodiments, autologous T cells are incubated with compositions of this invention. The cells can then be used for in vitro analysis, or alternatively for ex vivo administration.

II. MHC COMPLEXES

Antigens, including segments, fragments and other molecules derived from an antigenic species, including but not limited to peptides, carbohydrates, lipids or other molecules presented by classical and non-classical MHC molecules of the invention are typically complexed or operatively coupled to a MHC molecule or derivative thereof. Antigen recognition by T lymphocytes is major histocompatibility complex (MHC)-restricted. A given T lymphocyte will recognize an antigen only when it is bound to a particular MHC molecule. In general, T lymphocytes are stimulated only in the presence of self MHC molecules, and antigen is recognized as fragments of the antigen bound to self MHC molecules. MHC restriction defines T lymphocyte specificity in terms of the antigen recognized and in terms of the MHC molecule that binds its antigenic fragment(s). In particular aspects certain antigen will be paired with certain MHC molecules or polypeptides derived there from.

The term "operatively coupled" or "coated" as used herein, refers to a situation where individual polypeptide (e.g., MHC) and antigenic (e.g., peptide) components are combined to form the active complex prior to binding at the target site, for example, an immune cell. This includes the situation where the individual polypeptide complex components are synthesized or recombinantly expressed and subsequently isolated and combined to form a complex, in vitro, prior to administration to a subject; the situation where a chimeric or fusion polypeptide (i.e., each discrete protein component of the complex is contained in a single polypeptide chain) is synthesized or recombinantly expressed as an intact complex. Typically, polypeptide complexes are added to the microparticles to yield microparticles with adsorbed or coupled polypeptide complexes having a ratio of number of molecules:number of particle ratios from about, at least about or at most about 0.1, 0.5, 1, 10, 100, 500, 1000 or more to :1, more typically 0.1:1 to 50:1. A The polypeptide content of the microparticles can be determined using standard techniques.

A. MHC Molecules

Intracellular and extracellular antigens present quite different challenges to the immune system, both in terms of recognition and of appropriate response. Presentation of antigens to T cells is mediated by two distinct classes of molecules MHC class I (MHC-I) and MHC class II (MHC-II), which utilize distinct antigen processing pathways. Peptides derived from intracellular antigens are presented to $CD8^+$ T cells by MHC class I molecules, which are expressed on virtually all cells, while extracellular antigen-derived peptides are presented to $CD4^+$ T cells by MHC-II molecules. However, there are certain exceptions to this dichotomy. Several studies have shown that peptides generated from endocytosed particulate or soluble proteins are presented on MHC-I molecules in macrophages as well as in dendritic cells. In certain embodiments of the invention, a particular peptide derived from an autoantigen is identified and presented in the peptide/MHC/particle complex in the context of an appropriate MHC class I or II polypeptide. In certain aspects, the genetic make up of a subject may be assessed to determine which MHC polypeptide is to be used for a particular patient and a particular set of peptides.

Non-classical MHC molecules are also contemplated for use in MHC complexes of the invention. Non-classical MHC molecules are non-polymorphic, conserved among species, and possess narrow, deep, hydrophobic ligand binding pockets. These binding pockets are capable of presenting glycolipids and phospholipids to Natural Killer T (NKT) cells. NKT cells represent a unique lymphocyte population that co-express NK cell markers and a semi-invariant T cell receptor (TCR). They are implicated in the regulation of immune responses associated with a broad range of diseases.

B. Antigenic Components

Certain aspects of the invention include methods and compositions concerning antigenic compositions including segments, fragments, or epitopes of polypeptides, peptides, nucleic acids, carbohydrates, lipids and other molecules that provoke or induce an antigenic response, generally referred to as antigens. In particular, autoantigens, or antigenic segments or fragments of such autoantigens, which lead to the destruction of a cell via an autoimmune response, can be identified and used in making a MHC/particle complex described herein. Such autoantigens can be presented on pancreatic islets or cell supporting pancreatic islet cells. Embodiments of the invention include compositions and methods for the modulation of an immune response against a particular cell or set of cells that carry out a particular physiologic function.

1. Peptide Components and Proteinaceous Compositions

Polypeptides and peptides of the invention may be modified by various amino acid deletions, insertions, and/or substitutions. In particular embodiments, modified polypeptides and/or peptides are capable of modulating an immune response in a subject. As used herein, a "protein" or "polypeptide" or "peptide" refers to a molecule comprising at least five amino acid residues. In some embodiments, a wild-type version of a protein or peptide are employed, however, in many embodiments of the invention, a modified protein or polypeptide is employed to generate a peptide/MHC/particle complex. A peptide/MHC/particle complex can be used to generate an immune response and/or to modify the T cell population of the immune system (i.e., re-educate the immune system). The terms described above may be used interchangeably herein.

A "modified protein" or "modified polypeptide" or "modified peptide" refers to a protein or polypeptide whose chemical structure, particularly its amino acid sequence, is altered with respect to the wild-type protein or polypeptide. In some embodiments, a modified protein or polypeptide or peptide has at least one modified activity or function (recognizing that proteins or polypeptides or peptides may have multiple activities or functions). It is specifically contemplated that a modified protein or polypeptide or peptide may be altered with respect to one activity or function yet retain a wild-type activity or function in other respects, such as immunogenicity or ability to interact with other cells of the immune system when in the context of an MHC/particle complex.

Peptides of the invention include any autoreactive peptide. Autoreactive peptides include, but are not limited to $hInsB_{10\text{-}18}$ (HLVEALYLV (SEQ ID NO:1)), $hIGRP_{228\text{-}236}$ (LNIDLLWSV (SEQ ID NO:2)), $hIGRP_{265\text{-}273}$ (VLFGLGFAI (SEQ ID NO:3)), $IGRP_{206\text{-}214}$ (VYLKTNVFL (SEQ ID NO:4)), $hIGRP_{206\text{-}214}$ (VYLKTNLFL (SEQ ID NO:5)), NRP-A7 (KYNKANAFL (SEQ ID NO:6)), NRP-I4 (KYNIANVFL (SEQ ID NO:7)), NRP-V7 (KYNKANVFL (SEQ ID NO:8)), $YAI/D^b$ (FQDENYLYL (SEQ ID NO:9)) and/or $INS\ B_{15\text{-}23}$ (LYLVCGERG (SEQ ID NO: 10)), as well as peptides and proteins disclosed in U.S. Publication 20050202032, which is incorporated herein by reference in its entirety. Other peptides that may be used in conjunction with invention as autoreactive peptides or as control peptides include, but are not limited to INS-I9 (LYLVCGERI (SEQ ID NO:11)), TUM (KYQAVTTTL (SEQ ID NO:12)), and G6Pase (KYCLITIFL (SEQ ID NO:13)). In certain aspects, 1, 2, 3, 4, 5, 6 or more peptides can be used. Examples of peptides that can be used in conjunction with the present invention also include those provided in Table 1. These peptides may be associated with specific particles/MHC molecules or multiple peptides may be associated with a common particle and one or more MHC molecule. Administration of combinations of these peptides includes administering a population of particle having multiple peptides attached and/or administering multiple particle populations each having a specific peptide attached or a combination of such particles that includes particle with 1, 2, 3, 4, 5, 6, or more peptides attached to 1, 2, 3, 4, 5, 6, or more particles.

TABLE 1A

HLA class I-restricted epitopes for T1D

| Antigen | Epitope | HLA | Amino Acid Sequence | Comments | References |
|---|---|---|---|---|---|
| GAD65 | 114-123 | A2 | VMNILLQYVV (SEQ ID NO: 14) | Reactivity detected in immunized HHD mice and T1D patients | Blancou et. al. 2007, Panina-Bordignon et al. 1995, Mallone et al. 2007 |
|  | 563-545 | A2 | RMMEYGTTMV (SEQ ID NO: 15) | Reactivity detected in plasmid-immunized HHD mice and T1D patients | Blancou et. al. 2007 |
| GFAP | 143-151 | A2 | NLAQTDLATV (SEQ ID NO: 16) | Reactivity detected in T1D patients | Ouyang et. al. 2006 |
|  | 214-222 | A2 | QLARQQVHV (SEQ ID NO: 17) | Reactivity detected in T1D patients | Ouyang et al. 2006 |
| IA-2 | 172-180 | A2 | SLSPLQAEL (SEQ ID NO: 18) | Reactivity detected in T1D patients | Ouyang et al. 2006 |
|  | 482-490 | A2 | SLAAGVKLL (SEQ ID NO: 19) | Reactivity detected in T1D patients | Ouyang et al. 2006 |
|  | 805-813 | A2 | VIVMLTPLV (SEQ ID NO: 20) | Reactivity detected in plasmid-immunized HHD mice and T1D patients | Blancou et al. 2007 |

TABLE 1A-continued

HLA class I-restricted epitopes for T1D

| Antigen | Epitope | HLA | Amino Acid Sequence | Comments | References |
|---|---|---|---|---|---|
| ppIAPP | 5-13 | A2 | KLQVFLIVL (SEQ ID NO: 21) | Reactivity detected in T1D patients | Panagiotopoulos et al. 2003, Jarchum et al. 2008 |
|  | 9-17 | A2 | FLIVLSVAL (SEQ ID NO: 22) | Reactivity detected in T1D patients | Ouyang et al. 2006 |
| IGRP | 152-160 | A2 | FLWSVFMLI (SEQ ID NO: 23) | Reactivity detected in T1D patients | Ouyang et al. 2006 |
|  | 211-219 | A2 | NLFLFLFAV (SEQ ID NO: 24) | Reactivity detected in T1D patients | Jarchum et al. 2008 |
|  | 215-223 | A2 | FLFAVGFYL (SEQ ID NO: 25) | Reactivity detected in T1D patients | Ouyang et al. 2006, Jarchum et al. 2008 |
|  | 222-230 | A2 | YLLLRVLNI (SEQ ID NO: 26) | Reactivity detected in T1D patients | Jarchum et al. 2008 |
|  | 228-236 | A2 | LNIDLLWSV (SEQ ID NO: 2) | Reactivity to the corresponding epitope from murine IGRP (differing at 2 amino acids) detected in immunized HHD mice | Takaki et al. 2006 |
|  | 265-273 | A2 | VLFGLGFAI (SEQ ID NO: 3) | Reactivity detected in immunized HHD mice and recent-onset T1D patients | Takaki et al. 2006, Unger et al. 2007, Jarchum et al. 2008 |
|  | 293-301 | A2 | RLLCALTSL (SEQ ID NO: 27) | Reactivity detected in T1D patients | Ouyang et al. 2006 |
| Pro-insulin | L2-10 | A2 | ALWMRLLPL (SEQ ID NO: 28) | Reactivity detected in HHD mice and T1D patients | Mallone et al. 2007, Jarchum et al. 2007 |
|  | L3-11 | A2 | LWMRLLPLL (SEQ ID NO: 29) | Reactivity to the corresponding epitope from murine proinsulin 1 (differing at 5 amino acids) detected in HHD mice | Jarchum et al. 2007 |
|  | L6-14 | A2 | RLLPLLALL (SEQ ID NO: 30) | Reactivity detected in T1D patients | Mallone et al. 2007 |
|  | B5-14 | A2 | HLCGSHLVEA (SEQ ID NO: 31) | Reactivity to the corresponding mouse proinsulin 1 epitope (differing at one amino acid) detected in HHD mice | Jarchum et al. 2007 |
|  | B10-18 | A2 | HLVEALYLV (SEQ ID NO: 1) | Reactivity detected in immunized HHD mice and T1D patients | Toma et al. 2005, Hassainya et al. 2005, Pinkse et al. 2005 |
|  | B14-22 | A3, A11 | ALYLVCGER (SEQ ID NO: 32) | Reactivity detected in T1D patients | Toma et al. 2005 |
|  | B15-24 | A24 | LYLVCGERGF (SEQ ID NO: 33) | Reactivity detected in T1D patients | Toma et al. 2005 |
|  | B17-25 | A1, A3 | LVCGERGFF (SEQ ID NO: 34) | Reactivity detected in T1D patients | Toma et al. 2005 |
|  | B18-27 | A1, A2, B8, B18 | VCGERGFFYT (SEQ ID NO: 35) | Reactivity detected in T1D patients | Toma et al. 2005, Hassainya et al. 2005, |
|  | B20-27 | A1, B8 | GERGFFYT (SEQ ID NO: 36) | Reactivity detected in T1D patients | Toma et al. 2005 |
|  | B21-29 | A3 | ERGFFYTPK (SEQ ID NO: 37) | Reactivity detected in T1D patients | Toma et al. 2005 |

TABLE 1A-continued

HLA class I-restricted epitopes for T1D

| Antigen | Epitope | HLA | Amino Acid Sequence | Comments | References |
|---|---|---|---|---|---|
| | B25-C1 | B8 | FYTPKTRRE (SEQ ID NO: 38) | Reactivity detected in T1D patients | Toma et al. 2005 |
| | B27-C5 | B8 | TPKTRREAEDL (SEQ ID NO: 39) | Reactivity detected in T1D patients | Toma et al. 2005 |
| | C20-28 | A2 | SLQPLALEG (SEQ ID NO: 40) | Reactivity detected in peptide-immunized HHD mice | Hassainya et al. 2005 |
| | C25-33 | A2 | ALEGSLQKR (SEQ ID NO: 41) | Reactivity detected in peptide-immunized HHD mice | Hassainya et al. 2005 |
| | C29-A5 | A2 | SLQKRGIVEQ (SEQ ID NO: 42) | Reactivity detected in peptide-immunized HHD mice | Hassainya et al. 2005 |
| | A1-10 | A2 | GIVEQCCTSI (SEQ ID NO: 43) | Reactivity detected in peptide-immunized HHD mice | Hassainya et al. 2005 |
| | A2-10 | A2 | IVEQCCTSI (SEQ ID NO: 44) | Reactivity to the corresponding mouse proinsulin 1 epitope (differing at one amino acid) detected in HHD mice | Jarchum et al. 2007 |
| | A12-20 | A2 | SLYQLENYC (SEQ ID NO: 45) | Reactivity detected in peptide-immunized HHD mice | Hassainya et al. 2005 |

GAD65: 65 kDa Glutamic acid decarboxylase, GFAP: glial fibrillary acidic protein, IA-2: insulinoma-associated antigen 2, ppIAPP: Islet amyloid polypeptide precursor protein, IGRP: Islet-specific glucose 6-phosphatase catalytic subunit-related protein

TABLE 1B of HLA class I-restricted epitopes for MS

| Antigen | Epitope | HLA | Amino Acid Sequence | Comments | References |
|---|---|---|---|---|---|
| MAG | 287-295 | A2 | SLLLELEEV (SEQ ID NO: 46) | Recognized by CD8+ T cell lines generated from MS patients and healthy individuals | Tsuchida et al. 1994 |
| MAG | 509-517 | A2 | LMWAKIGPV (SEQ ID NO: 47) | Recognized by CD8+ T cell lines generated from MS patients and healthy individuals | Tsuchida et al. 1994 |
| MAG | 556-564 | A2 | VLFSSDFRI (SEQ ID NO: 48) | Recognized by CD8+ T cell lines generated from MS patients and healthy individuals | Tsuchida et al. 1994 |
| MBP | 110-118 | A2 | SLSRFSWGA (SEQ ID NO: 49) | Recognized by CD8+ T cell lines generated from MS patients and healthy individuals | Tsuchida et al. 1994, Jurewicz et al. 1998 |
| MOG | 114-122 | A2 | KVEDPFYWV (SEQ ID NO: 50) | Reactivity detected in peptide-immunized HHD mice | Mars et al. 2007 |
| MOG | 166-175 | A2 | RTFDPHFLRV (SEQ ID NO: 51) | Reactivity detected in peptide-immunized HHD mice | Mars et al. 2007 |
| MOG | 172-180 | A2 | FLRVPCWKI (SEQ ID NO: 52) | Reactivity detected in peptide-immunized HHD mice | Mars et al. 2007 |
| MOG | 179-188 | A2 | KITLFVIVPV (SEQ ID NO: 53) | Reactivity detected in peptide-immunized HHD mice | Mars et al. 2007 |
| MOG | 188-196 | A2 | VLGPLVALI (SEQ ID NO: 54) | Reactivity detected in peptide-immunized HHD mice | Mars et al. 2007 |
| MOG | 181-189 | A2 | TLFVIVPVL (SEQ ID NO: 55) | Reactivity detected in peptide-immunized HHD mice | Mars et al. 2007 |

TABLE 1B-continued of HLA class I-restricted epitopes for MS

| Antigen | Epitope | HLA | Amino Acid Sequence | Comments | References |
|---------|---------|-----|---------------------|----------|------------|
| MOG | 205-214 | A2 | RLAGQFLEEL (SEQ ID NO: 56) | Reactivity detected in peptide-immunized HHD mice | Mars et al. 2007 |
| PLP | 80-88 | A2 | FLYGALLLA (SEQ ID NO: 57) | Recognized by CD8+ T cell lines generated from MS patients and healthy individuals | Tsuchida et al. 1994, Dressel et al. 1997 |

MBP: myelin basic protein, MAG: myelin-associated glycoprotein, MOG: myelin oligodendrocyte glycoprotein, PLP: proteolipid protein In certain embodiments, the size of a protein or polypeptide (wild-type or modified), including any complex of a protein or peptide of interest and in particular a MHC/peptide fusion, may comprise, but is not limited to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, including any range or value derivable therein, or derivative thereof. In certain aspects, 5, 6, 7, 8, 9, 10 or more contiguous amino acids, including derivatives thereof, and fragments of an autoantigen, such as those amino acid sequences disclosed and referenced herein, can be used as antigens It is contemplated that polypeptides may be mutated by truncation, rendering them shorter than their corresponding wild-type form, but also they might be altered by fusing or conjugating a heterologous protein sequence with a particular function (e.g., for presentation as a protein complex, for enhanced immunogenicity, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's GenBank and GenPept databases (on the World Wide Web at ncbi.nlm.nih.gov/). The all or part of the coding regions for these genes may be amplified and/or expressed using the techniques disclosed herein or as would be know to those of ordinary skill in the art.

Amino acid sequence variants of autoantigenic epitopes and other polypeptides of these compositions can be substitutional, insertional, or deletion variants. A modification in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more non-contiguous or contiguous amino acids of a peptide or polypeptide, as compared to wild-type. A peptide or polypeptide that results in an autoimmune response and in particular a pathologic autoimmune response are contemplated for use in methods of the invention.

Deletion variants typically lack one or more residues of the native or wild-type amino acid sequence. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of a polypeptide or peptide is affected, such as avidity or affinity for a cellular receptor(s). Non-conservative changes typically involve substituting a residue with one that is chemically dissimilar, such as a polar or charged amino acid for a non-polar or uncharged amino acid, and vice versa.

Proteins of the invention may be recombinant, or synthesized in vitro. Alternatively, a recombinant protein may be isolated from bacteria or other host cell.

The term "functionally equivalent codon" is used herein to refer to codons that encode the same amino acid, such as the six codons for arginine or serine, and also refers to codons that encode biologically equivalent amino acids (see Table 2, below).

TABLE 2

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' nucleic acid sequences, respectively, and yet still be essentially as set forth in one of the sequences disclosed herein, so long as the sequence meets the criteria set forth above, including the maintenance of biological protein activity (e.g., immunogenicity). The addition of terminal sequences particularly applies to nucleic acid sequences that may, for example, include various non-coding sequences flanking either of the 5' or 3' portions of the coding region.

It is contemplated that in compositions of the invention, there is between about 0.001 mg and about 10 mg of total protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 50, 100 µg/ml or mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be peptide/MHC/particle complex.

The present invention contemplates the administration of a peptide/MHC/particle complex to effect a diagnosis, treatment or preventative therapy against the development of a disease or condition associated with autoimmune responses.

In addition, U.S. Pat. No. 4,554,101 (Hopp), which is incorporated herein by reference, teaches the identification and preparation of epitopes from primary amino acid sequences on the basis of hydrophilicity. Through the methods disclosed in Hopp, one of skill in the art would be able to identify potential epitopes from within an amino acid sequence and confirm their immunogenicity. Numerous scientific publications have also been devoted to the prediction of secondary structure and to the identification of epitopes, from analyses of amino acid sequences (Chou & Fasman, 1974a,b; 1978a,b; 1979). Any of these may be used, if desired, to supplement the teachings of Hopp in U.S. Pat. No. 4,554,101.

2. Other Antigenic Components

Molecules other than peptides can be used as antigens or antigenic fragments in complex with MHC molecules, such molecules include, but are not limited to carbohydrates, lipids, small molecules, and the like. Carbohydrates are major components of the outer surface of a variety of cells. Certain carbohydrates are characteristic of different stages of differentiation and very often these carbohydrates are recognized by specific antibodies. Expression of distinct carbohydrates can be restricted to specific cell types. Autoantibody responses to endometrial and serum antigens have been shown to be a common feature of endometriosis. There has been described a serum autoantibody response in endometriosis to a number of previously identified antigens, including 2-Heremans Schmidt glycoprotein and carbonic anhydrase, that is specific for a carbohydrate epitope (Yeaman et al., 2002).

C. Substrates/Particles

In certain aspect, antigen/MHC complexes are operatively coupled to a substrate. A substrate can be in the form of a particle. Particles can have a structure of variable dimension and known variously as a microsphere, microparticle, nanoparticle, nanosphere, or liposome. Such particulate formulations containing an antigen/MHC complex can be formed by covalent or non-covalent coupling of the complex to the particle.

By "particle," "microparticle," "bead," "microsphere," and grammatical equivalents herein is meant small discrete particles that are administrable to a subject. In certain embodiments, the particles are substantially spherical in shape. The term "substantially spherical," as used herein, means that the shape of the particles does not deviate from a sphere by more than about 10%. Various known antigen or peptide complexes of the invention may be applied to the particles.

The particles typically consist of a substantially spherical core and optionally one or more layers. The core may vary in size and composition. In addition to the core, the particle may have one or more layers to provide functionalities appropriate for the applications of interest. The thicknesses of layers, if present, may vary depending on the needs of the specific applications. For example, layers may impart useful optical properties.

Layers may also impart chemical or biological functionalities, referred to herein as chemically active or biologically active layers, and for these functionalities the layer or layers may typically range in thickness from about 0.001 micrometers (1 nanometer) to about 10 micrometers or more (depending on the desired particle diameter), these layers typically being applied on the outer surface of the particle.

The compositions of the core and layers may vary. Suitable materials for the particles or the core include, but are not limited to polymers, ceramics, glasses, minerals, and the like. Examples include, but are not limited to, standard and specialty glasses, silica, polystyrene, polyester, polycarbonate, acrylic polymers, polyacrylamide, polyacrylonitrile, polyamide, fluoropolymers, silicone, celluloses, silicon, metals (e.g., iron, gold, silver), minerals (e.g., ruby), nanoparticles (e.g., gold nanoparticles, colloidal particles, metal oxides, metal sulfides, metal selenides, and magnetic materials such as iron oxide), and composites thereof. The core could be of homogeneous composition, or a composite of two or more classes of material depending on the properties desired. In certain aspects, metal nanoparticles will be used. These metal particles or nanoparticles can be formed from Au, Pt, Pd, Cu, Ag, Co, Fe, Ni, Mn, Sm, Nd, Pr, Gd, Ti, Zr, Si, and In, precursors, their binary alloys, their ternary alloys and their intermetallic compounds. See U.S. Pat. No. 6,712,997, which is incorporated herein by reference in its entirety As previously stated, the particle may, in addition to the core, include one or more layers. The purposes for including layers in the microparticle may vary. Alternatively, the surface of the particle may be functionalized directly. A layer may provide suitable surfaces for attaching chemical functionalities for chemical binding or coupling sites.

Layers can be produced on the microparticles in a variety of ways known to those skilled in the art. Examples include sol-gel chemistry techniques such as described in Iler (1979); Brinker and Scherer (1990). Additional approaches to producing layers on particles include surface chemistry and encapsulation techniques such as described in Partch and Brown (1998); Pekarek et al. (1994); Hanprasopwattana (1996); Davies (1998); and references therein. Vapor deposition techniques may also be used; see for example Golman and Shinohara (2000); and U.S. Pat. No. 6,387,498. Still other approaches include layer-by-layer self-assembly techniques such as described in Sukhorukov et al. (1998); Caruso et al. (1998); Caruso et al. (1999); U.S. Pat. No. 6,103,379 and references cited therein.

Particles may be formed by contacting an aqueous phase containing the antigen/MHC complex and a polymer and a nonaqueous phase followed by evaporation of the nonaqueous phase to cause the coalescence of particles from the aqueous phase as taught in U.S. Pat. Nos. 4,589,330 or 4,818, 542. Preferred polymers for such preparations are natural or synthetic copolymers or polymers selected from the group consisting of gleatin agar, starch, arabinogalactan, albumin, collagen, polyglycolic acid, polylactic acid, glycolide-L(−) lactide poly(episilon-caprolactone, poly(epsilon-caprolactone-CO-lactic acid), poly(epsilon-caprolactone-CO-glycolic acid), poly($\beta$-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic acid, glycolide-L(−)lactide poly(episilon-caprolactone, poly(epsilon-caprolactone-CO-lactic acid), and poly(epsilon-caprolactone-CO-glycolic acid. Solvents useful for dissolving the polymer include: water, hexafluoroisopropanol, methylenechloride, tetrahydrofuran, hexane, benzene, or hexafluoroacetone sesquihydrate.

The term "microparticle" as used herein, refers to a particle of about 10 nm to about 150 µm in diameter, more preferably about 200 nm to about 30 µm in diameter, and most preferably about 500 nm to about 10 µm in diameter. Preferably, the microparticle will be of a diameter that permits parenteral or mucosal administration without occluding needles and capillaries. Microparticle size is readily determined by techniques well known in the art, such as photon correlation spectroscopy, laser diffractometry and/or scanning electron microscopy. The term "particle" may also be used to denote a microparticle as defined herein. For a broad overview of protein delivery systems, see Banga, Therapeutic Peptides and Proteins: Formulation, Processing, and Delivery Systems, Technomic Publishing Company, Inc., Lancaster, Pa., 1995. Particulate systems include microspheres, microparticles, microcapsules, nanocapsules, nanospheres, and nanoparticles. Particles, microspheres, and microcapsules smaller than about 1 µm are generally referred to as nanoparticles, nanospheres, and nanocapsules, respectively. Microparticles are typically around 100 µm in diameter and are administered subcutaneously or intramuscularly (see, Kreuter, 1994; Tice & Tabibi, 1992).

D. Coupling Antigen-MHC Comples with Microparticle or Nanoparticle

In order to couple the substrate or particles to the antigen-MHC comoples the following techniques can be applied.

The binding can be generated by chemically modifying the substrate or particle which typically involves the generation of "functional groups" on the surface, said functional groups being capable of binding to an antigen-MHC complex, and/or linking the optionally chemically modified surface of the surface or particle with covalently or non-covalently bonded so-called "linking molecules," followed by reacting the antigen-MHC complex with the particles obtained.

The term "linking molecule" means a substance capable of linking with the substrate or particle and also capable of linking to an antigen-MHC complex.

The term "functional groups" as used hereinbefore is not restricted to reactive chemical groups forming covalent bonds, but also includes chemical groups leading to an ionic interaction or hydrogen bonds with the antigen-MHC complex. Moreover, it should be noted that a strict distinction between "functional groups" generated at the surface and linking molecules bearing "functional groups" is not possible, since sometimes the modification of the surface requires the reaction of smaller linking molecules such as ethylene glycol with the particle surface.

The functional groups or the linking molecules bearing them may be selected from amino groups, carbonic acid groups, thiols, thioethers, disulfides, guanidino, hydroxyl groups, amine groups, vicinal dioles, aldehydes, alpha-halo-acetyl groups, mercury organyles, ester groups, acid halide, acid thioester, acid anhydride, isocyanates, isothiocyanates, sulfonic acid halides, imidoesters, diazoacetates, diazonium salts, 1,2-diketones, phosphonic acids, phosphoric acid esters, sulfonic acids, azolides, imidazoles, indoles, N-maleimides, alpha-beta-unsaturated carbonyl compounds, arylhalogenides or their derivatives.

Non-limiting examples for other linking molecules with higher molecular weights are nucleic acid molecules, polymers, copolymers, polymerizable coupling agents, silica, proteins, and chain-like molecules having a surface with the opposed polarity with respect to the substrate or particle. Nucleic acids can provide a link to affinity molecules containing themselves nucleic acid molecules, though with a complementary sequence with respect to the linking molecule.

As examples for polymerizable coupling agents, diacetylene, styrene butadiene, vinylacetate, acrylate, acrylamide, vinyl compounds, styrene, silicone oxide, boron oxide, phosphorous oxide, borates, pyrrole, polypyrrole and phosphates can be cited.

The surface of the substrate or particle can be chemically modified, for instance by the binding of phosphonic acid derivatives having functional reactive groups. One example of these phosphonic acid or phosphonic acid ester derivates is imino-bis(methylenphosphono) carbonic acid which can be synthesized according to the "Mannich-Moedritzer" reaction. This binding reaction can be performed with substrate or particle as directly obtained from the preparation process or after a pre-treatment (for instance with trimethylsilyl bromide). In the first case the phosphonic acid (ester) derivative may for instance displace components of the reaction medium which are still bound to the surface. This displacement can be enhanced at higher temperatures. Trimethylsilyl bromide, on the other hand, is believed to dealkylate alkyl group-containing phosphorous-based complexing agents, thereby creating new binding sites for the phosphonic acid (ester) derivative. The phosphonic acid (ester) derivative, or linking molecules bound thereto, may display the same functional groups as given above. A further example of the surface treatment of the substrate or particle involves heating in a diole such as ethylene glycol. It should be noted that this treatment may be redundant if the synthesis already proceeded in a diole. Under these circumstances the synthesis product directly obtained is likely to show the necessary functional groups. This treatment is however applicable to substrate or particle that were produced in N- or P-containing complexing agents. If such substrate or particle are subjected to an after-treatment with ethylene glycol, ingredients of the reaction medium (e.g. complexing agent) still binding to the surface can be replaced by the diole and/or can be dealkylated.

It is also possible to replace N-containing complexing agents still bound to the particle surface by primary amine derivatives having a second functional group. The surface of the substrate or particle can also be coated with silica. Silica allows a relatively simple chemical conjugation of organic molecules since silica easily reacts with organic linkers, such as triethoxysilane or chlorosilane. The particle surface may also be coated by homo- or copolymers. Examples for polymerizable coupling agents are. N-(3-aminopropyl)-3-mercaptobenzamidine, 3-(trimethoxysilyl)propylhydrazide and 3-trimethoxysilyl)propylmaleimide. Other non-limiting examples of polymerizable coupling agents are mentioned herein. These coupling agents can be used singly or in combination depending on the type of copolymer to be generated as a coating.

Another surface modification technique that can be used with substrates or particles containing oxidic transition metal compounds is conversion of the oxidic transition metal compounds by chlorine gas or organic chlorination agents to the corresponding oxychlorides. These oxychlorides are capable of reacting with nucleophiles, such as hydroxy or amino groups as often found in biomolecules. This technique allows generating a direct conjugation with proteins, for instance via the amino group of lysine side chains. The conjugation with proteins after surface modification with oxychlorides can also be effected by using a bi-functional linker, such as maleimidopropionic acid hydrazide.

For non-covalent linking techniques, chain-type molecules having a polarity or charge opposite to that of the substrate or particle surface are particularly suitable. Examples for linking molecules which can be non-covalently linked to core/shell nanoparticles involve anionic, cationic or zwitter-ionic surfactants, acid or basic proteins, polyamines, polyamides, polysulfone or polycarboxylic acid. The hydrophobic interaction between substrate or particle and amphiphilic reagent having a functional reactive group can generate the necessary link. In particular, chain-type molecules with amphiphilic character, such as phospholipids or derivatised polysaccharides, which can be crosslinked with each other, are useful. The absorption of these molecules on the surface can be achieved by coincubation. The binding between affinity molecule and substrate or particle can also be based on non-covalent, self-organising bonds. One example thereof involves simple detection probes with biotin as linking molecule and avidin- or strepdavidin-coupled molecules.

Protocols for coupling reactions of functional groups to biological molecules can be found in the literature, for instance in "Bioconjugate Techniques" (Greg T. Hermanson, Academic Press 1996). The biological molecule (e.g., MHC molecule or derivative thereof) can be coupled to the linking molecule, covalently or non-covalently, in line with standard procedures of organic chemistry such as oxidation, halogenation, alkylation, acylation, addition, substitution or amidation. These methods for coupling the covalently or non-covalently bound linking molecule can be applied prior to the coupling of the linking molecule to the substrate or particle or thereafter. Further, it is possible, by means of incubation, to effect a direct binding of molecules to correspondingly pre-treated substrate or particles (for instance by trimethylsilyl bromide), which display a modified surface due to this pre-treatment (for instance a higher charge or polar surface).

E. Protein Production

The present invention describes polypeptides, peptides, and proteins for use in various embodiments of the present invention. For example, specific peptides and their complexes are assayed for their abilities to elicit or modulate an immune response. In specific embodiments, all or part of the peptides or proteins of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are known to one skilled in the art and are briefly discussed herein. Examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk-, hgprt- or aprt-cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

F. Nucleic Acids

The present invention may include recombinant polynucleotides encoding the proteins, polypeptides, peptides of the invention. The nucleic acid sequences for autoantigens and MHC molecules for presenting the autoantigens, are included and can be used to prepare a peptide/MHC complex.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs. It also is contemplated that a particular polypeptide from a given species may be encoded by nucleic acids containing natural variations that having slightly different nucleic acid sequences but, nonetheless, encode the same or substantially similar protein, polypeptide, or peptide.

In particular embodiments, the invention concerns isolated nucleic acid segments and recombinant vectors incorporating nucleic acid sequences that encode an autoantigen and/or a MHC molecule. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. A tag or other heterologous polypeptide may be added to the modified polypeptide-encoding sequence, wherein "heterologous" refers to a polypeptide that is not the same as the modified polypeptide.

III. DIAGNOSTIC AND THERAPEUTIC METHODS

A. Immune Response and Assays

As discussed above, the invention concerns evoking or modifying an immune response in a subject against an autoantigen. In one embodiment, the resulting immune response or condition can protect against or treat a subject having, suspected of having, or at risk of developing a disease or symptoms related an autoimmune response.

1. Immunoassays

The present invention includes the implementation of serological assays to evaluate whether and to what extent an immune response is present, induced, evoked, or modified by a peptide/MHC/particle complex. There are many types of immunoassays that can be implemented. Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

One method for quantifying the number of circulating antigen-specific $CD8^+$ T cells is the tetramer assay. In this assay, a specific epitope is bound to synthetic tetrameric forms of fluorescently labeled MHC Class I molecules. Since $CD8^+$ T cells recognize antigen in the form of short peptides bound to Class I molecules, cells with the appropriate T cell receptor will bind to the labeled tetramers and can be quantified by flow cytometry. Although this method is less time-consuming than an ELISPOT assay, the tetramer assay measures only binding, not function. Not all cells that bind a particular antigen necessarily become activated. However, correlation between ELISPOT, tetramer, and cytotoxicity assays has been demonstrated (Goulder et al., 2000).

Immunoassays generally are binding assays. Certain preferred immunoassays are the various types of enzyme linked immunosorbent assays (ELISAs), radioimmunoassays (RIA) or bead based assays, such as Luminex® technology, are known in the art. Immunohistochemical detection using tissue sections is also particularly useful.

In one example of ELISA, the antibodies or antigens are immobilized on a selected surface, such as a well in a polystyrene microtiter plate, dipstick, or column support. Then, a test composition suspected of containing the desired antigen or antibody, such as a clinical sample, is added to the wells. After binding and washing to remove non specifically bound immune complexes, the bound antigen or antibody may be detected. Detection is generally achieved by the addition of another antibody, specific for the desired antigen or antibody, that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label. Variations on ELISA techniques are known to those of skill in the art.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non specifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of the antigen or antibody to the well, coating with a non reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

B. Assessing an Autoimmune Response or Condition

In addition to the use of proteins, polypeptides, and/or peptides to treat or prevent an autoimmune condition, the present invention contemplates the use of these polypeptides, proteins, and/or peptides in a variety of ways, including the detection of the presence of autoantigens or an autoimmune condition to diagnose the presence of certain autoreactive cell populations or conditions. In accordance with the invention, a method of detecting the presence of autoreactivity involves the steps of obtaining a sample from an individual, for example, from one's blood, saliva, tissues, bone, muscle, cartilage, or skin. Following isolation of the sample, diagnostic assays utilizing the polypeptides, proteins, and/or peptides of the present invention may be carried out to detect the presence of autoreactivity, and such assay techniques for determining such in a sample are well known to those skilled in the art and include methods such as tetramer assays, immunoassays, western blot analysis, and/or ELISA assays.

As used herein the phrase "immune response" or its equivalent "immunological response" refers to the development of a cellular (mediated by antigen-specific T cells or their secretion products) directed against an autoantigen or an related epitope of an autoantigen. A cellular immune response is elicited by the presentation of polypeptide epitopes in association with Class I or Class II MHC molecules, to activate antigen-specific CD4+ T helper cells and/or CD8+ cytotoxic T cells. The response may also involve activation of other components.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion. The presence of a cell-mediated immunological response can be determined by proliferation assays (CD4+ T cells) or CTL (cytotoxic T lymphocyte) assays.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Optionally, an autoantigen or preferably an epitope of an autoantigen, can be chemically conjugated to, or expressed as, a fusion protein with other proteins, such as MHC and MHC related proteins.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

C. Treatment Methods

A method of the present invention includes treatment for a disease or condition caused by one or more autoantigens. An immunogenic polypeptide of the invention can be given to induce or modify an immune response in a person having, suspected of having, or at risk of developing an autoimmune condition or disease. Methods may be employed with respect to individuals who have tested positive for autoreactivity or who are deemed to be at risk for developing such a condition or related condition.

IV. DIAGNOSTIC AND THERAPEUTIC TARGETS

Embodiments of the invention can be used to treat or ameliorate a number of immune-mediated or autoimmune disease, e.g., diabetes, graft rejection, etc. "Autoimmune disease" includes diseases or disorders arising from and directed against an individual's own tissues or organs or manifestation thereof or a condition resulting there from. In one embodiment, it refers to a condition that results from, or is aggravated by, the production by T cells that are reactive with normal body tissues and antigens. Examples of autoimmune diseases or disorders include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, nonspecific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes). Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

EXAMPLE 1

T1D Protection by Treatment with Peptide/MHC-Coated Nanoparticles

Diabetes protection by treatment with super-paramagnetic nanoparticles coated with NRP-V7/$K^d$ monomers. To study whether NRP-V7/$K^d$-coated nanoparticles are tolerogenic in vivo, 8.3-TCR-transgenic NOD mice were treated (also referred to as 8.3-NOD or V$\alpha$17.4+TCR-TG mice further below) with several i.v. injections of a small volume of particles (5 µl, carrying 0.6 µg of NRP-V7, once every 3 days). The transgenic high-avidity IGRP$_{206-214}$-reactive splenic CD8+ T-cell pools of these mice were significantly depleted in three doses (the splenic CD8:CD4 ratios dropped from ~4 to ~1) (FIG. 1A). The few non-deleted CD8+ T-cells showed signs of prior activation as determined by assessing CD44 expression (FIG. 1B) and were hyporesponsive to antigenic stimulation in vitro, suggesting that they had been anergized by the treatment (FIG. 1C).

Figure 2:
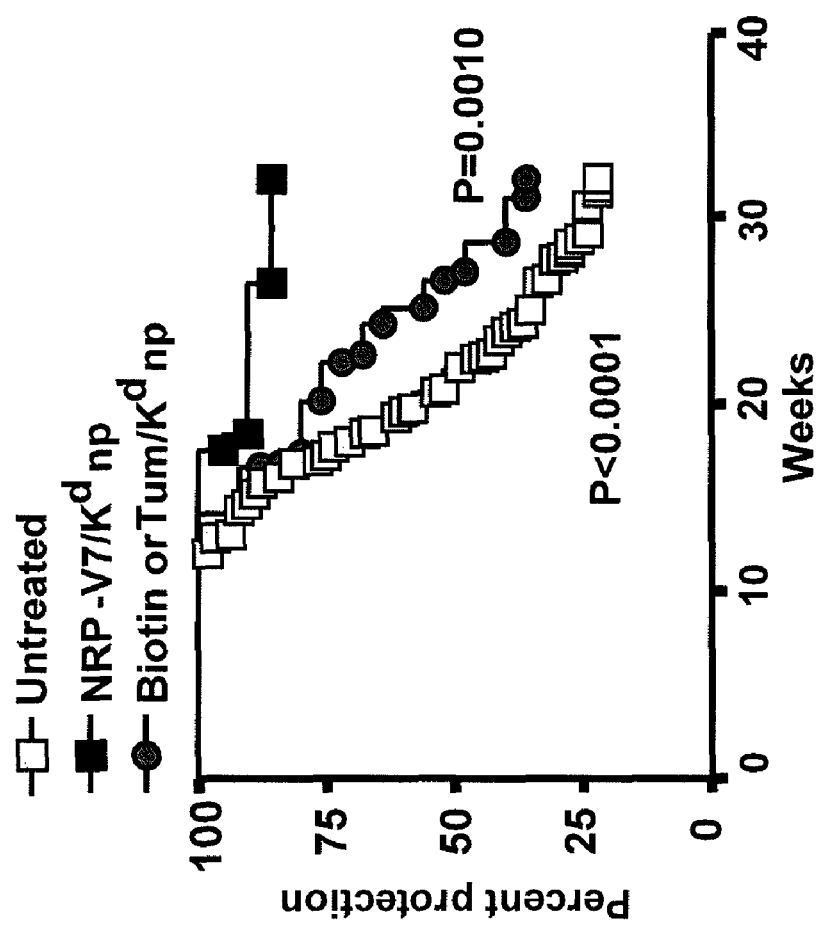
FIG. 2. Systemic administration of NRP-V7/$K^d$-np in young NOD mice resulted in diabetes protection. NOD mice were injected intravenously with 7.5 mg of NRP-V7/$K^d$ np at 4, 6 and 8 weeks of age, and every three weeks thereafter until 32 weeks of age. 85% of the NRP-V7/$K^d$ np-treated animals (n=21) remained diabetes-free at 32 weeks of age, compared to 36% and 23% in the control-np-treated (n=25) and untreated group (n=65), respectively.

To study the effectiveness of 'multiplexing', paramagnetic beads (referred herein to as "beads," "nanoparticles," or "np" were coated with 6 different peptide/MHC monomers. Cohorts of wild-type NOD mice were treated with a pool of these beads, with beads coated with a control peptide (TUM)/$K^d$, or with beads coated with NRP-V7/$K^d$ (it was expected that, like NRP-V7, NRP-V7/$K^d$-coated beads would delete the entire IGRP$_{206-214}$-reactive pool, without affording diabetes protection (Han et al., 2005)). Surprisingly, unlike mice treated with uncoated beads, avidin-biotin-coated beads (also referred herein to "biotin-np"), TUM/$K^d$-coated beads or NRP-V7 peptide alone (Han et al. 2005), NOD mice treated with NRP-V7/$K^d$-coated beads (once every 2-3 wk) were highly protected from T1D (FIG. 2).

Figure 3:
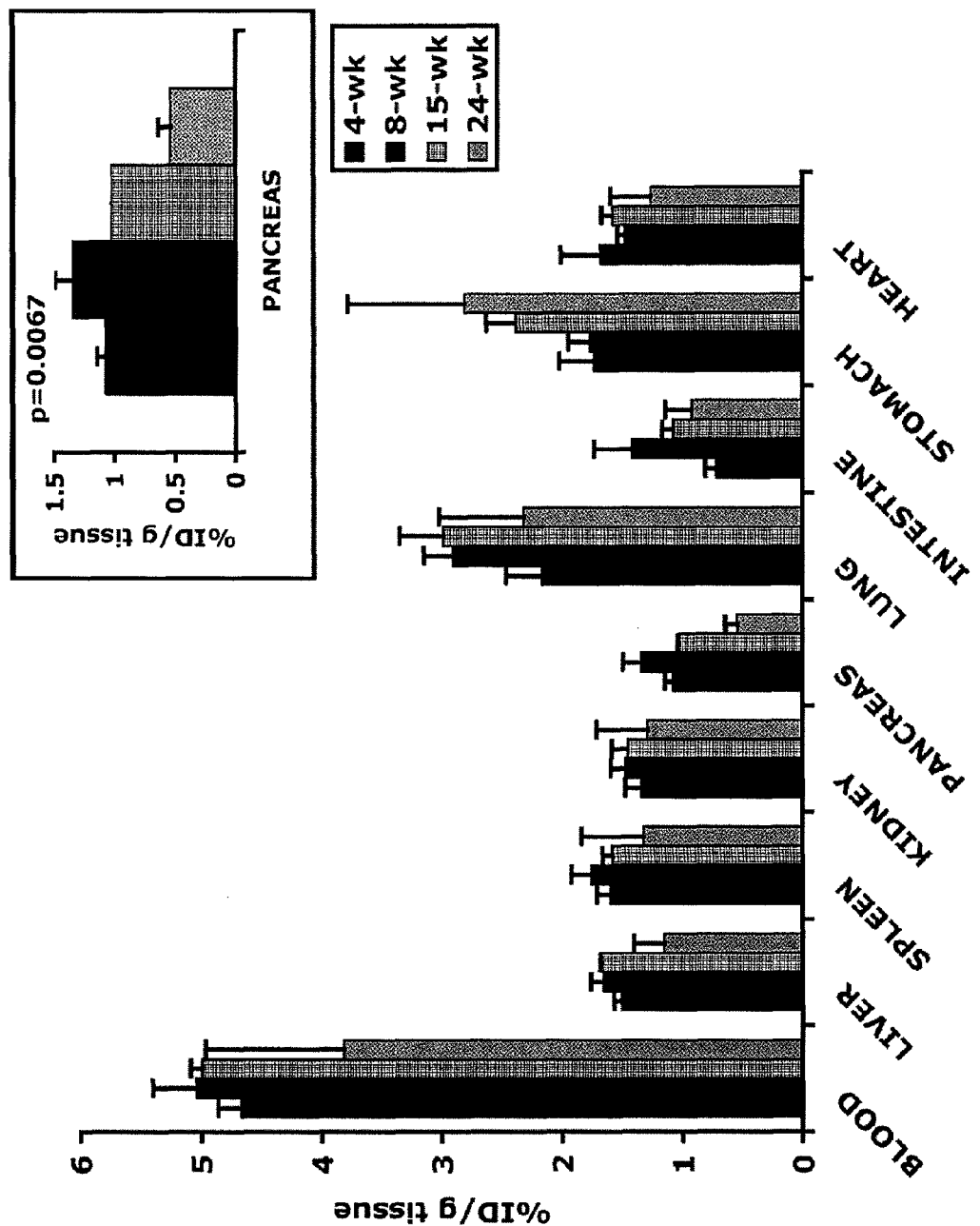
FIG. 3. Biodistribution of radiolabeled peptide/MHC-coated nanoparticles within 24 hours of a systemic dose.
Figure 4:
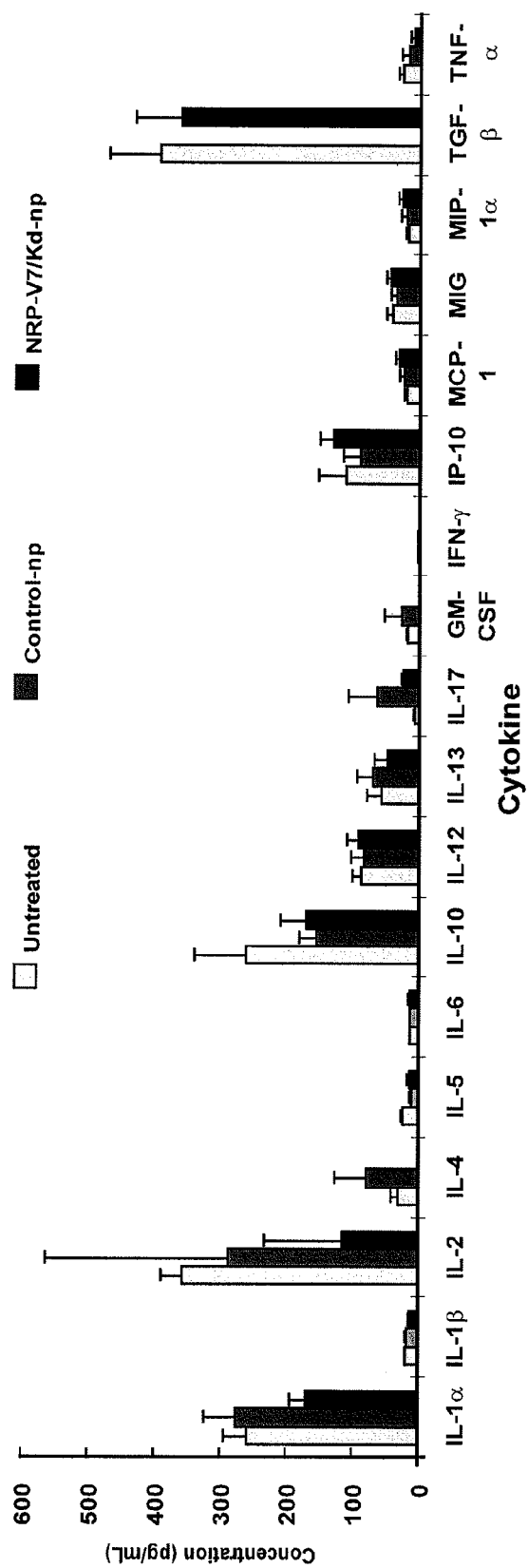
FIG. 4. Serum cytokine levels in NRP-V7/$K^d$-np- and biotinylated np-treated NOD mice vs. untreated NOD mice (n=5, 5, and 10, respectively). Ten week-old NOD females were injected with two doses of the respective np per week for the duration of 5 weeks. Sera were collected 6 hours after the last injection and subjected to 20-plex cytokine analysis using Luminex beads array technology.

Systemic expansion of low-avidity clonotypes by treatment with super-paramagnetic nanoparticles coated with NRP-V7/$K^d$ monomers. Studies employing radioactively-labeled beads indicated that their tissue distribution within 24 hours of a single injection was systemic, at all ages examined, as expected given their small size (FIG. 3). Measurements of the levels of several cytokines and chemokines in the serum of treated mice further indicated that np treatment did not induce a "cytokine storm" (i.e., increased serum levels of cytokines resulting from stimulation of diverse immune cell types, including NRP-V7-reactive CD8+ T-cells) (FIG. 4).

Figures 5A, 5B, 5C, 5D, 5E:
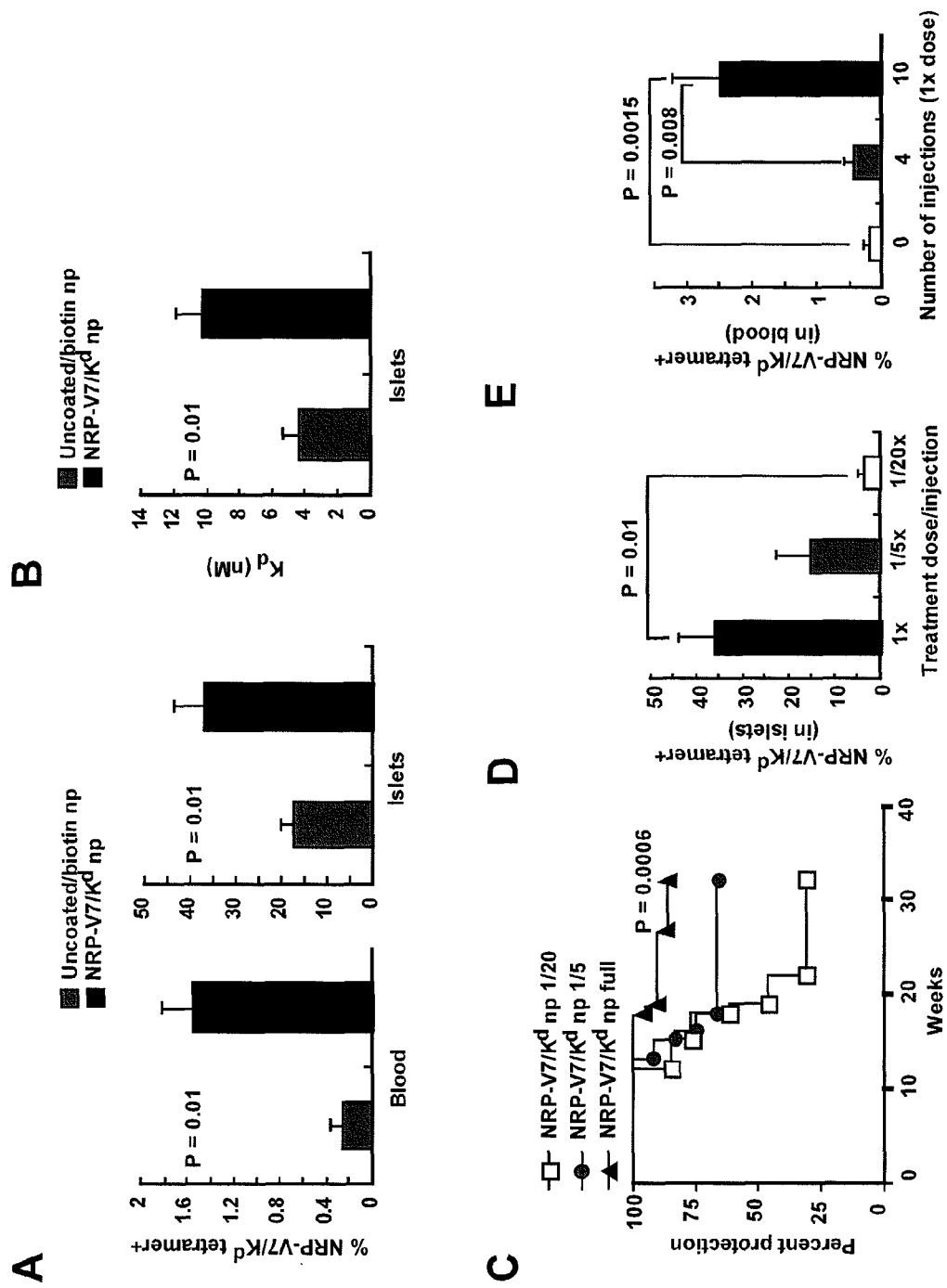
FIGS. 5A-5E. Systemic administration of NRP-V7/$K^d$-np in young NOD mice resulted in the expansion of tetramer-positive CD8+ T cells.

Most interestingly, however, mice treated with NRP-V7/$K^d$-coated beads had significantly increased pools of circulating and intra-islet NRP-V7/$K^d$ tetramer+ CD8$^+$ cells at the end of the follow-up period (32 wk), as compared to those of age-matched non-diabetic animals treated with control nanoparticles (FIG. 5A). Notably, the intra-islet CD8+ T-cells of the NRP-V7/$K^d$-nanoparticle-treated mice bound NRP-V7/$K^d$ tetramers with significantly lower avidity (higher $K_d$) than those found in the islets of control mice, suggesting that the nanoparticle treatment had fostered the expansion of non-pathogenic low-avidity clonotypes at the expense of their pathogenic high-avidity counterparts (FIG. 5B). These effects were dose-dependent, because mice treated with lower doses were much less protected from diabetes (FIG. 5C) and had smaller percentages of tetramer+ CD8+ T-cells in islets and spleen (FIG. 5D, and data not shown). Furthermore, the effects of each dose appeared to be cumulative, because mice receiving 10 consecutive doses of nanoparticles (two/week starting at 10 weeks of age) had significantly higher percentages of circulating tetramer+ CD8+ T-cells than those receiving only 4 doses (also starting at 10 weeks of age; FIG. 5E).

Figure 6A:
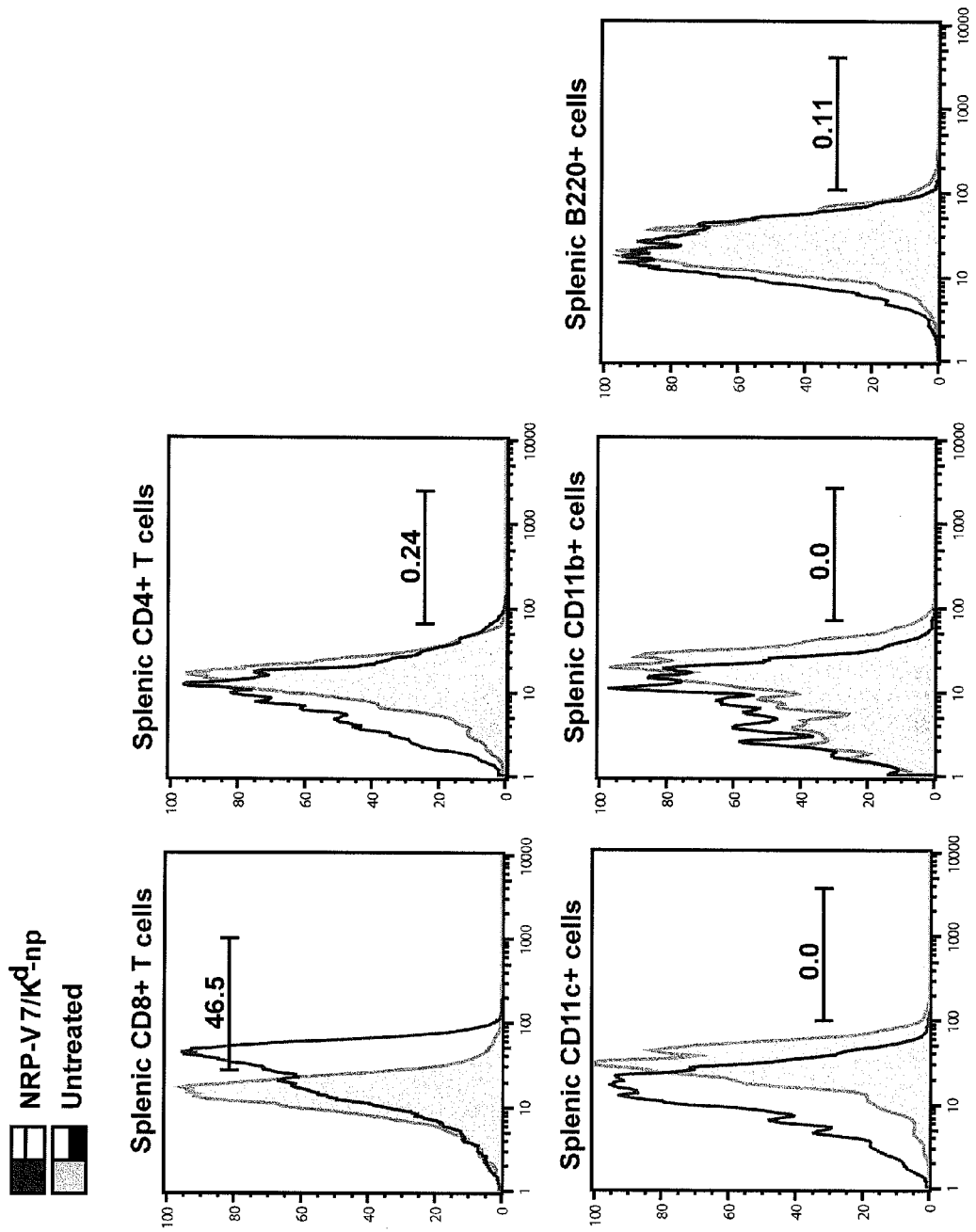
FIGS. 6A-6C. Specific uptake of peptide/MHC-coated np by cognate CD8+ T-cells.
Figure 6B:
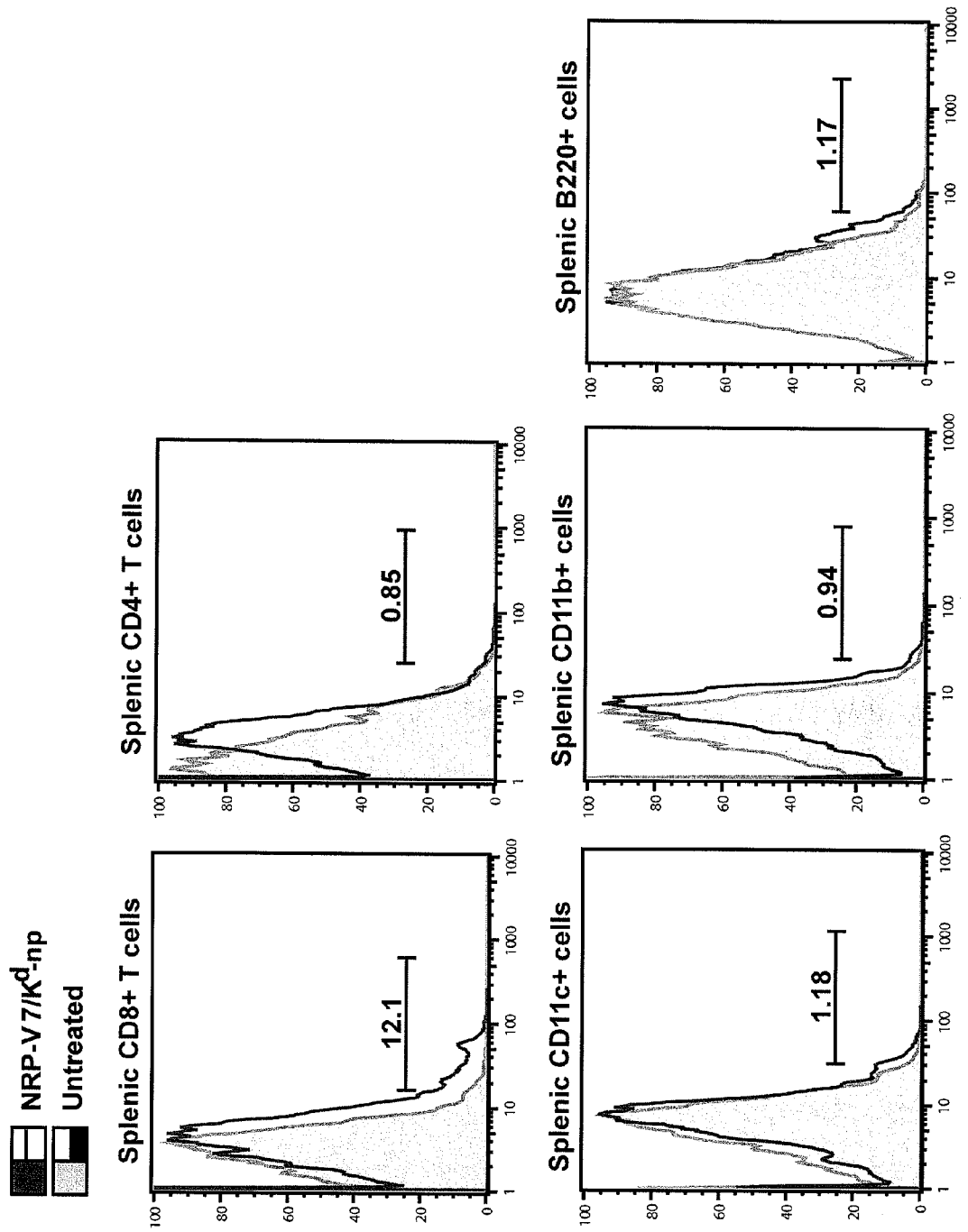
Figure 6C:
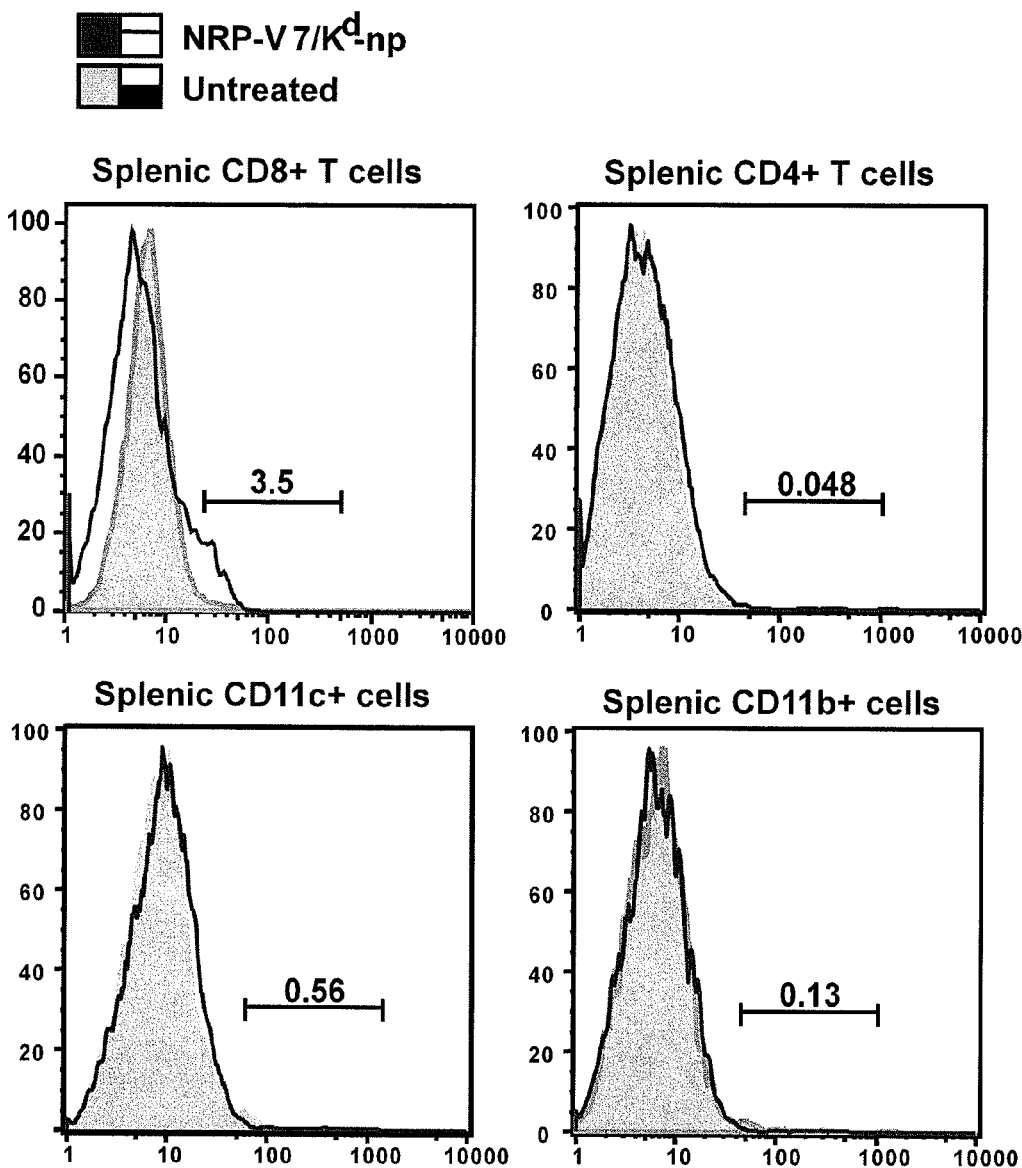

The above results suggested that the NRP-V7/K/$K^d$-coated np were specifically recognized and uptaken by NRP-V7-reactive CD8+ T-cells (via their TCR). To investigate this, the inventors assessed the presence of green fluorescence (bound to the avidin molecule of the peptide-MHC np complex) in different splenocyte subpopulations of NOD mice expressing a transgenic NRP-V7-reactive TCR as well as in wild-type, non-transgenic NOD mice. Within 24-40 hours of NRP-V7/$K^d$ np injection, green fluorescence could only be detected in the CD8+ T-cell subset of TCR-transgenic mice (FIG. 6A) and, to a much lesser extent, in the CD8+ T-cell subset of non-transgenic mice (FIG. 6B). No detectable accumulation of green fluorescence could be detected in the splenic CD4+ T, B, CD11b+, or CD11c+ cell subsets of either type of mice (FIGS. 6A and 6B).

Figures 7A, 7B, 7C, 7D:
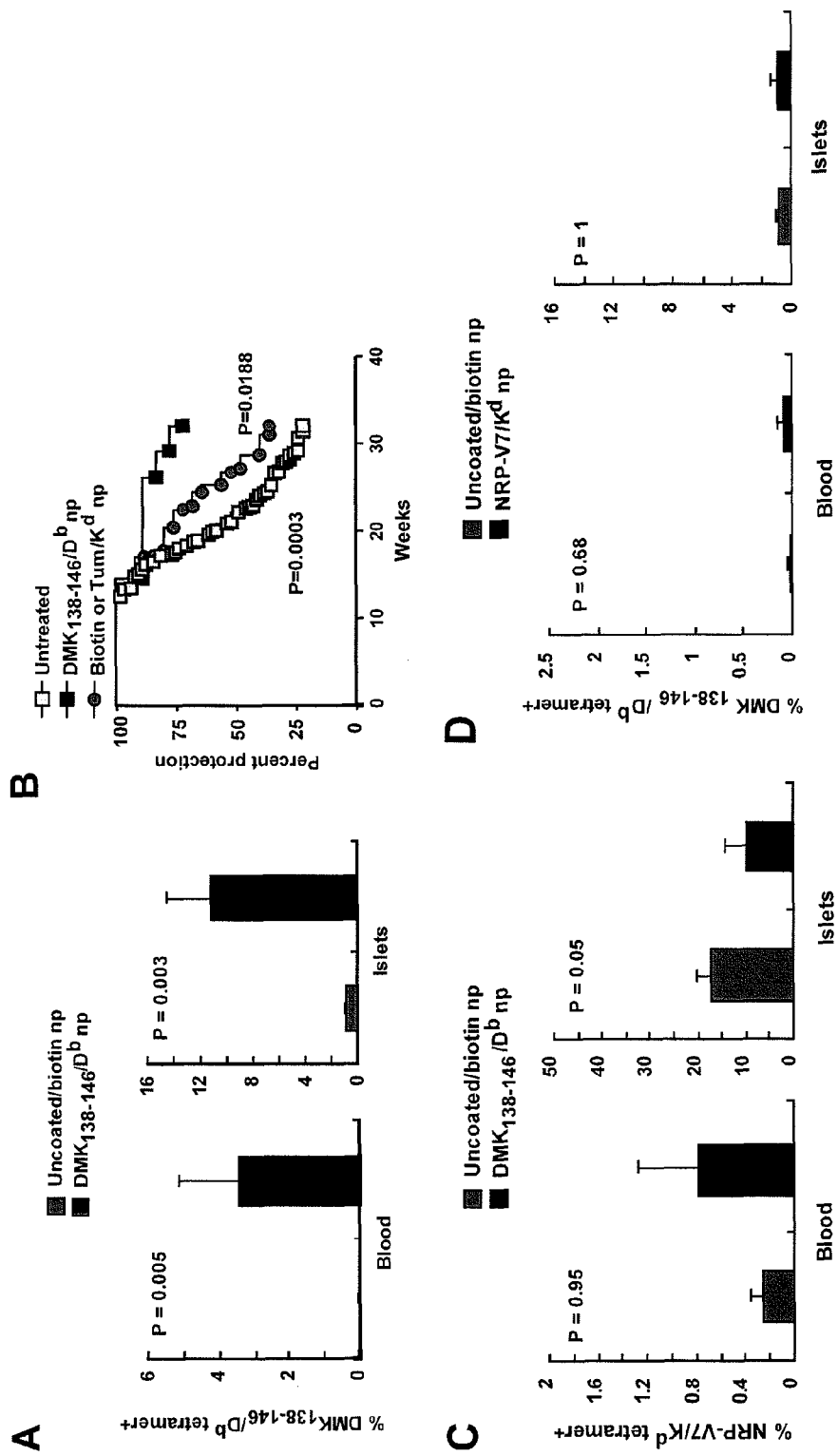
FIGS. 7A-7E. Systemic administration of $DMK_{138-146}$/$D^b$-np in young NOD mice resulted in the selective expansion of $DMK_{138-146}$-reactive CD8+ T cells and afforded diabetes protection.
Figure 7E:
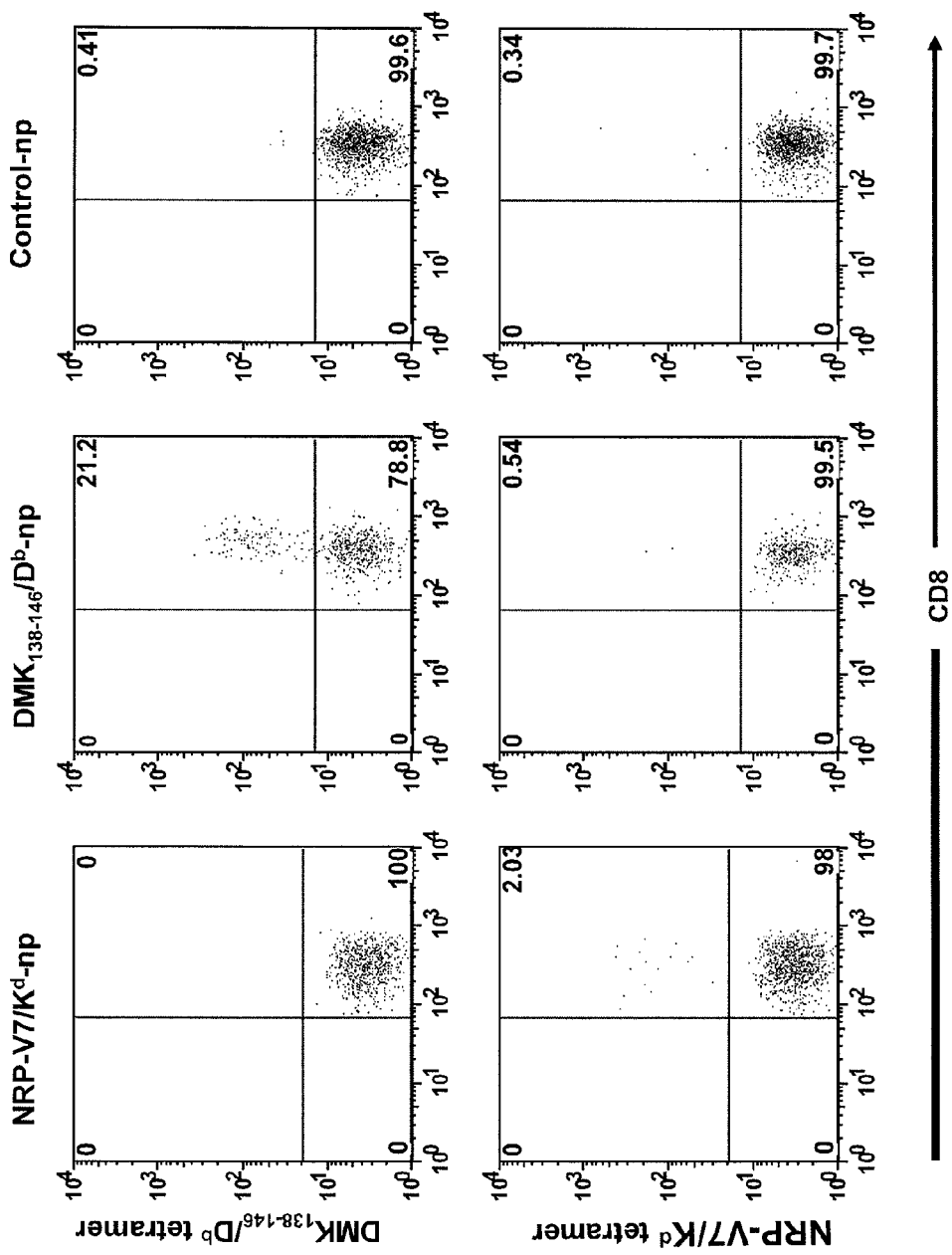

Anti-diabetogenic properties of super-paramagnetic nanoparticles coated with a subdominant autoantigenic peptide/MHC (DMK$_{138-146}$/$D^b$) complex. The inventors investigated whether the protective effects of the above therapeutic avenue were a peculiarity of NRP-V7-reactive CD8+ T-cells (a prevalent autoreactive T-cell subset in NOD mice), or a phenomenon applicable to other, less dominant autoantigenic specificities. To this end, mice were treated with beads coated with a peptide that is derived from another autoantigen that is presented by $D^b$ and is targeted by a much smaller pool of diabetogenic autoreactive CD8+ T-cells (residues 138-146 of Dystrophia Myotonica Kinase; DMK; herein referred to as "DMK$_{138-146}$/$D^b$") (Lieberman et al., 2004). As was the case with nanoparticles coated with NRP-V7/$K^d$ complexes, treatment of NOD mice with $DMK_{138-146}/D^b$-coated nanoparticles caused significant expansions of circulating, splenic and intra-islet $DMK_{138-146}/D^b$-reactive CD8+ T cells (FIG. 7A) and afforded significant diabetes protection (FIG. 7B). T cell expansion in vivo was antigen-specific because $DMK_{138-146}/D^b$-coated nanoparticles did not expand NRP-V7-reactive CD8+ T cells (FIG. 7C) and NRP-V7/$K^d$-coated nanoparticles did not expand $DMK_{138-146}/D^b$-reactive T cells (FIG. 7D). FIG. 7E shows representative FACS staining profiles.

Figure 8:
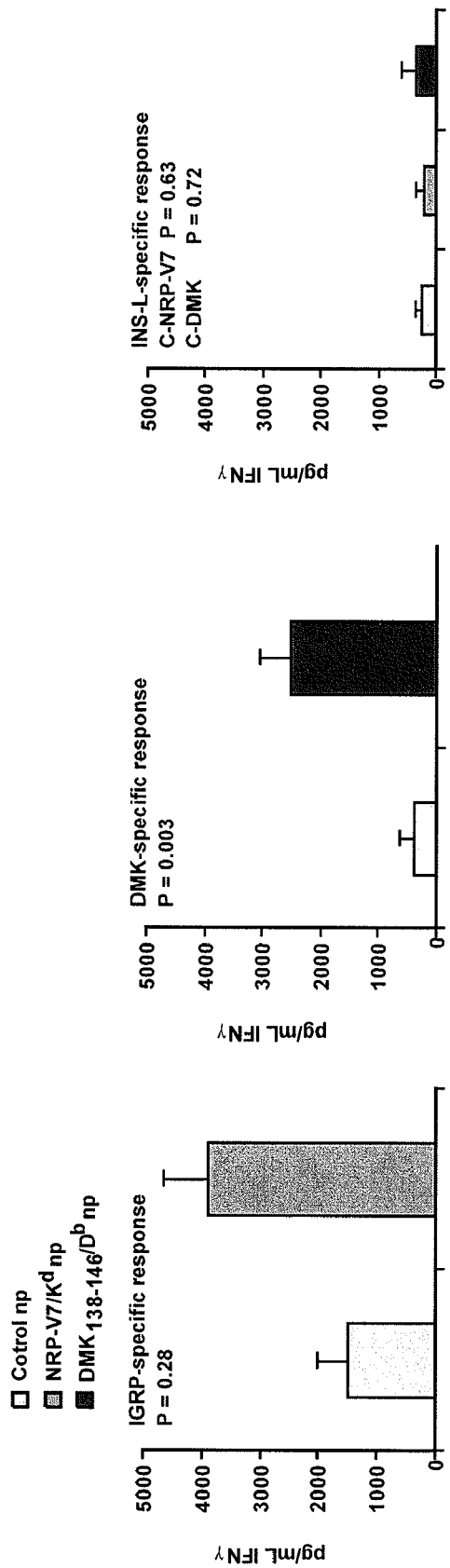
FIG. 8. Enhanced recruitment of $IGRP_{206-214}$- or $DMK_{138-146}$-reactive CD8+ T-cells to pancreatic islets upon treatment with NRP-V7/$K^d$- or $DMK_{138-146}$/$D^b$-coated nanoparticles, respectively. Mice received one intravenous injection of nanoparticles once every 2-3 weeks, starting at 4 weeks of age. These samples are from mice at the end of treatment (~32 wk of age). Islet-associated CD8+ T-cells were assayed for IFN-γ production in response to $IGRP_{206-214}$-, $DMK_{138-146}$-, or Insulin-L (INS-L)-pulsed antigen-presenting cells. INS-L was used as a control (NRP-V7/$K^d$-np-treated n=8, $DMK_{138-146}$/$D^b$-np-treated n=5, Control-np treated n=8 for IGRP- and INS-L-specific responses, n=3 for DMK-specific responses).

Impaired recruitment of other IGRP-autoreactive CD8+ T-cell specificities to islets in mice treated with NRP-V7/$K^d$- or $DMK_{138-146}/D^b$-coated nanoparticles. Next the inventors investigated whether recruitment of nanoparticle-expanded low-avidity NRP-V7- and/or $DMK_{138-146}/D^b$-reactive CD8+ T cells impaired the recruitment of other beta cell autoreactive T cell specificities to islets, as was the case in APL-treated animals (Han et al. 2005). This was done by comparing responsiveness of islet-associated CD8+ T cells of mice treated with control, NRP-V7/$K^d$- or $DMK_{138-146}/D^b$-coated nanoparticles to a panel of 76 different IGRP epitopes as well as $DMK_{138-146}$. As expected, given that they contained increased frequencies of NRP-V7- or $DMK_{138-146}/D^b$-reactive clonotypes, the islet-associated CD8+ T cells of mice treated with NRP-V7/$K^d$-coated and $DMK_{138-146}/D^b$-coated nanoparticles produced significantly more IFN-γ in response to NRP-V7 and $DMK_{138-146}$, respectively, than those isolated from control mice (FIG. 8). Notably, there were significant reductions in the number of epitopes capable of eliciting significant IFN-γ responses by the islet-associated CD8+ T cells of mice treated with NRP-V7/$K^d$ or $DMK_{138-146}/D^b$-coated nanoparticles, as compared to those from mice treated with control nanoparticles, suggesting impaired recruitment and/or accumulation (Table 3).

TABLE 3

Reactivity of islet-associated CD8+ T-cells to a panel of IGRP epitopes in mice treated with control nanoparticles or nanoparticles coated with NRP-V7/$K^d$ or $DMK_{138-146}/D^b$ monomers. Mice received one intravenous injection of nanoparticles once every 2-3 weeks, starting at 4 weeks of age. These samples are from mice at the end of treatment (~32 wk of age). Islet-associated CD8+ T-cells were assayed for IFN-g production in response to peptide-pulsed antigen-presenting cells and the number of positive (>50 pg/ml) and negative responses (<50 pg/ml) counted.

| Treatment | % Positive | % Negative | # Positive | # Negative | n |
|---|---|---|---|---|---|
| Control | 20 | 80 | 138 | 546 | 9 |
| V7 | 7 | 93 | 28 | 352 | 5 |
| YAI | 5 | 95 | 15 | 289 | 4 |

Figures 9A, 9B, 9C, 9D:
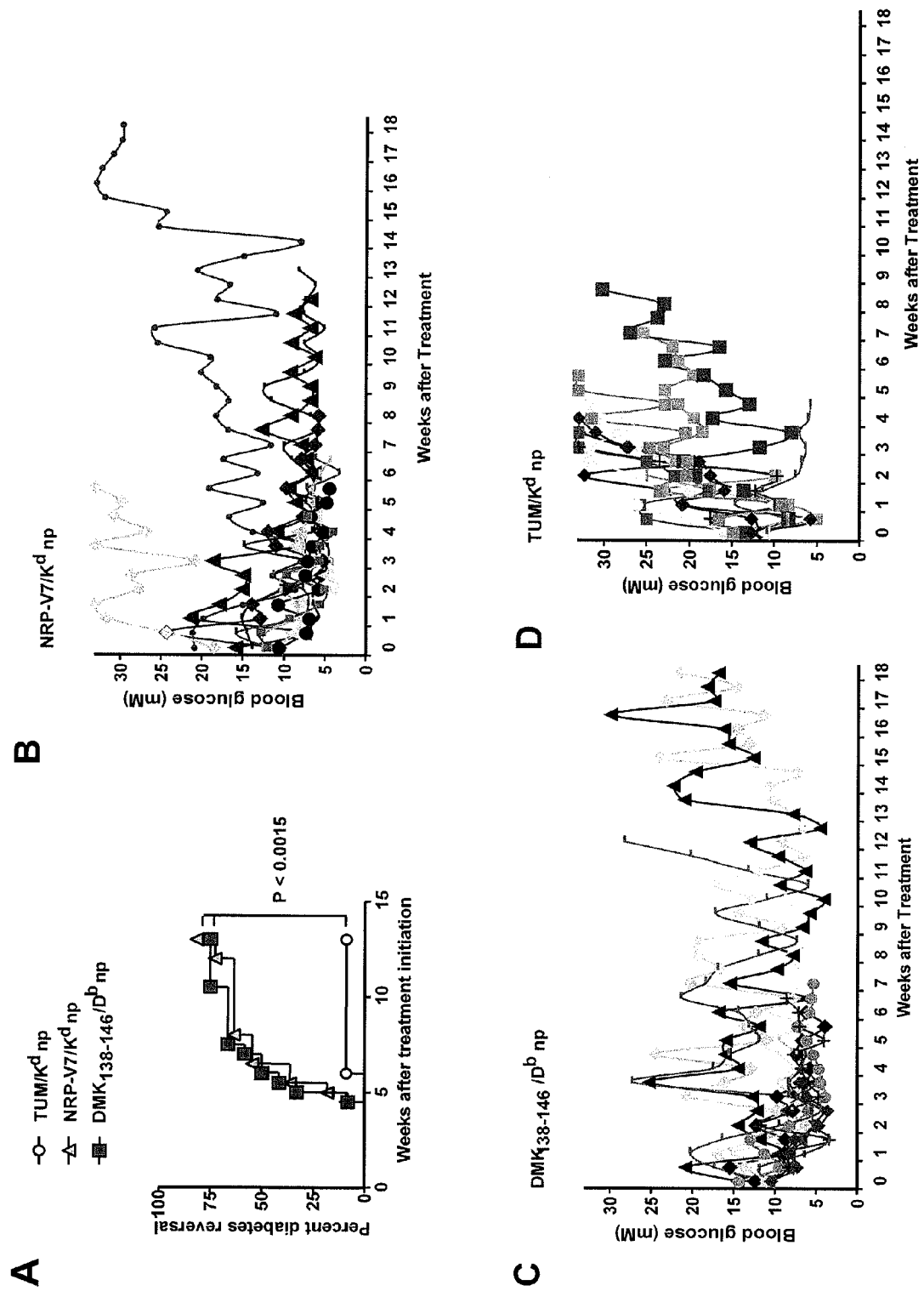
FIGS. 9A-9F. NRP-V7/$K^d$-np and $DMK_{138-146}$/$D^b$-np treatment reverses hyperglycemia when given at diabetes onset.
Figures 9E, 9F:
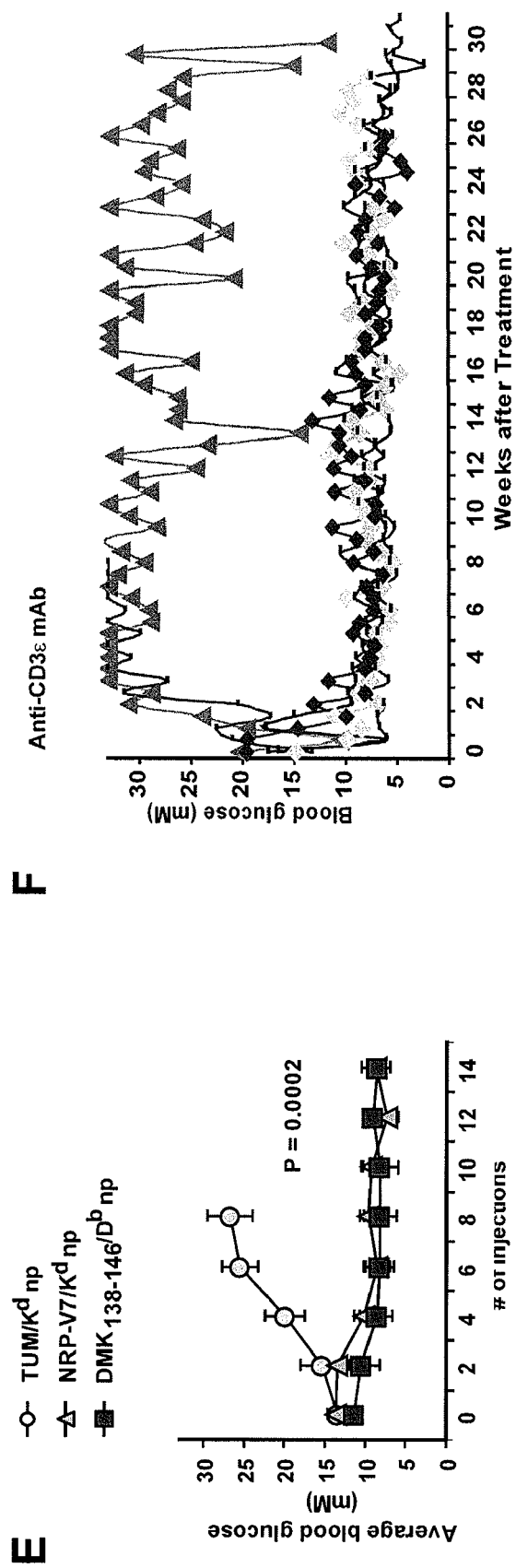

NRP-V7/$K^d$- and $DMK_{138-146}/D^b$-coated nanoparticles induce high rates of diabetes remission in newly diabetic NOD mice. The effectiveness of treatment during the pre-diabetic stage prompted investigation into the ability of nanoparticle therapy to restore normoglycemia in newly diagnosed diabetic mice. Cohorts of mice were monitored twice a week for blood glucose levels and considered hyperglycemic at ≧10.5 mM blood glucose. Mice were randomized into mice receiving TUM/$K^d$-coated nanoparticles or NRP-V7/$K^d$-coated nanoparticles (two weekly injections). Half a unit of subcutaneous insulin was also given once daily to mice displaying glycosuria, to reduce beta cell stress and foster beta cell regeneration. Additional cohorts of mice received $DMK_{138-146}/D^b$-coated nanoparticles. Treatment with monoclonal anti-CD3 antibody (20 μg/d for 5 days), which has been shown to induce stable remission in a variable percentage of animals in different studies, was used as positive control. As shown in FIGS. 9A and 9B, 9 of 11 mice treated with NRP-V7/$K^d$-coated particles became normoglycemic within 5-12 weeks of treatment. The two mice that did not cure were the only two which received the first dose of treatment when their blood glucose levels were >18 mM/l, suggesting that effectiveness may require the presence of a critical mass of residual beta cells. Likewise, 8 of 11 mice treated with $DMK_{138-146}/D^b$-coated nanoparticles became normoglycemic (FIGS. 9A and 9C), with the other three displaying oscillating levels of blood glucose that did not reach 20 mM for an extended period of time (FIG. 9C). In contrast, only 1 of 9 mice receiving control TUM/$K^d$-coated nanoparticles did not progress to overt hyperglycemia (FIGS. 9A and 9D). FIG. 9E compares the average levels of blood glucose in each group of mice after each injection of nanoparticles. FIG. 9F shows the results of treatment with anti-CD3 mAb, a non-antigen-specific immunotherapeutic strategy that has been previously shown to also be able to restore normoglycemia in acutely diabetic mice (positive control group); 4 of 6 mice became normoglycemic. When taken together, these results suggest that effectiveness of antigen-specific nanoparticle therapy approach is comparable to that of a non-antigen-specific approach that has proven successful in mice and, more recently, human diabetic patients (Keymeulen et al., 2005; Herold et al., 2002).

Figures 10A, 10B, 10C, 10D:
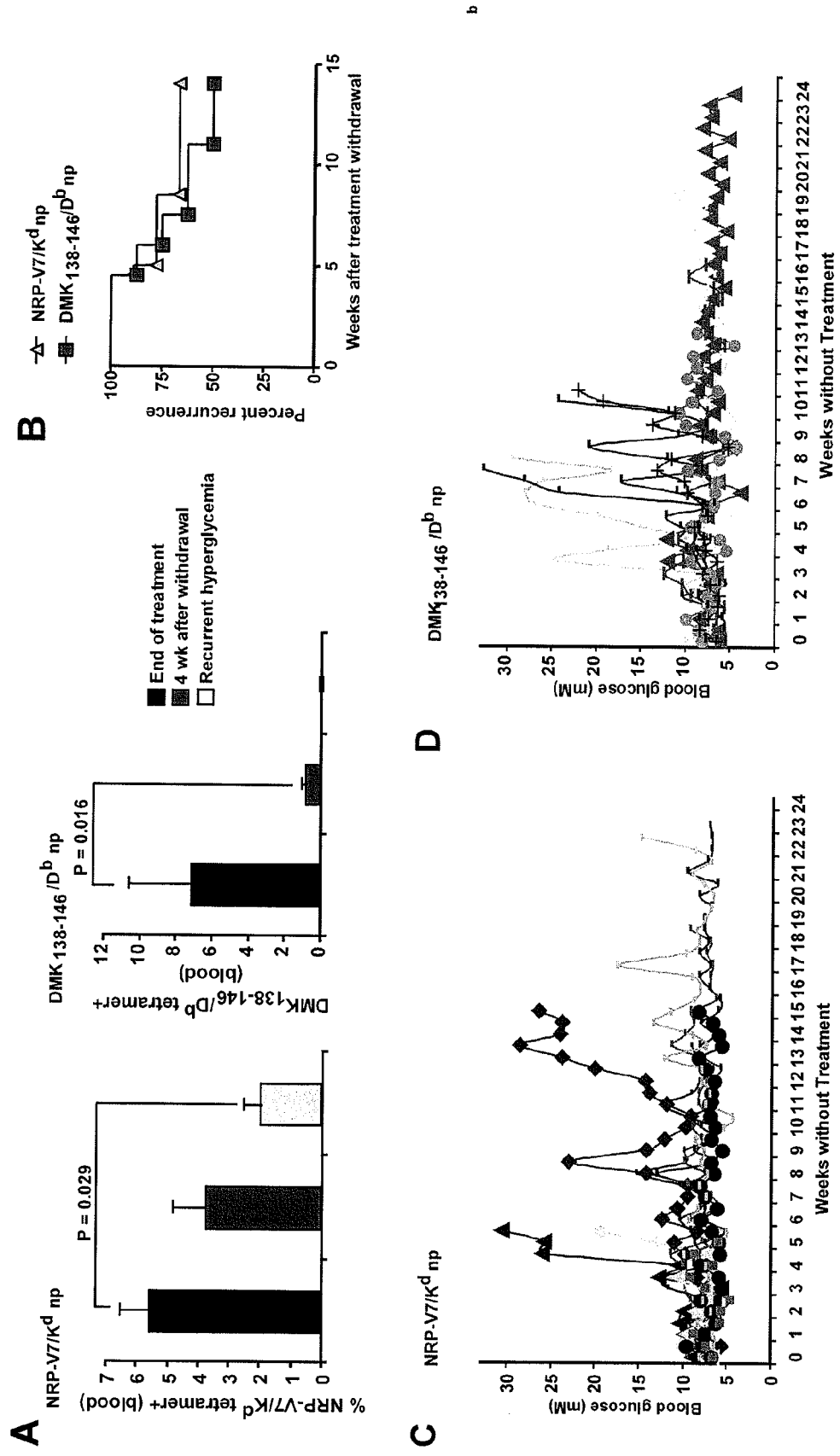
FIGS. 10A-10D. Outcome of treatment withdrawal.

To investigate whether the effects of treatment in diabetic mice were long-lasting, as seen in pre-diabetic animals, treatment was withdrawn after 4 consecutive weeks of normoglycemia and followed the mice for diabetes recurrence. The effects of treatment on the size of the circulating tetramer-positive pool were assessed at treatment withdrawal, 4 weeks later and at the time of recurrent hyperglycemia. There was a decline in the size of the circulating tetramer-reactive T cell pool 4 weeks after cessation of treatment, as expected (FIG. 10A), and, presumably as a result, ~30-45% of the diabetic mice that had been cured developed recurrent hyperglycemia between 4 and 14 weeks later (FIGS. 10B and 10C). This suggested that re-activation of the expanded low-avidity autoreactive T-cell pool, either by endogenous autoantigen (i.e., in pre-diabetic animals) or by booster injections of nanoparticles (i.e., in diabetic animals with a severely reduced beta cell mass) may be required for long-term protection. Similar results were obtained in mice that had been treated with $DMK_{138-146}/D^b$-coated nanoparticles (FIGS. 10A, 10B, and 10D).

Figures 11A, 11B, 11C, 11D:
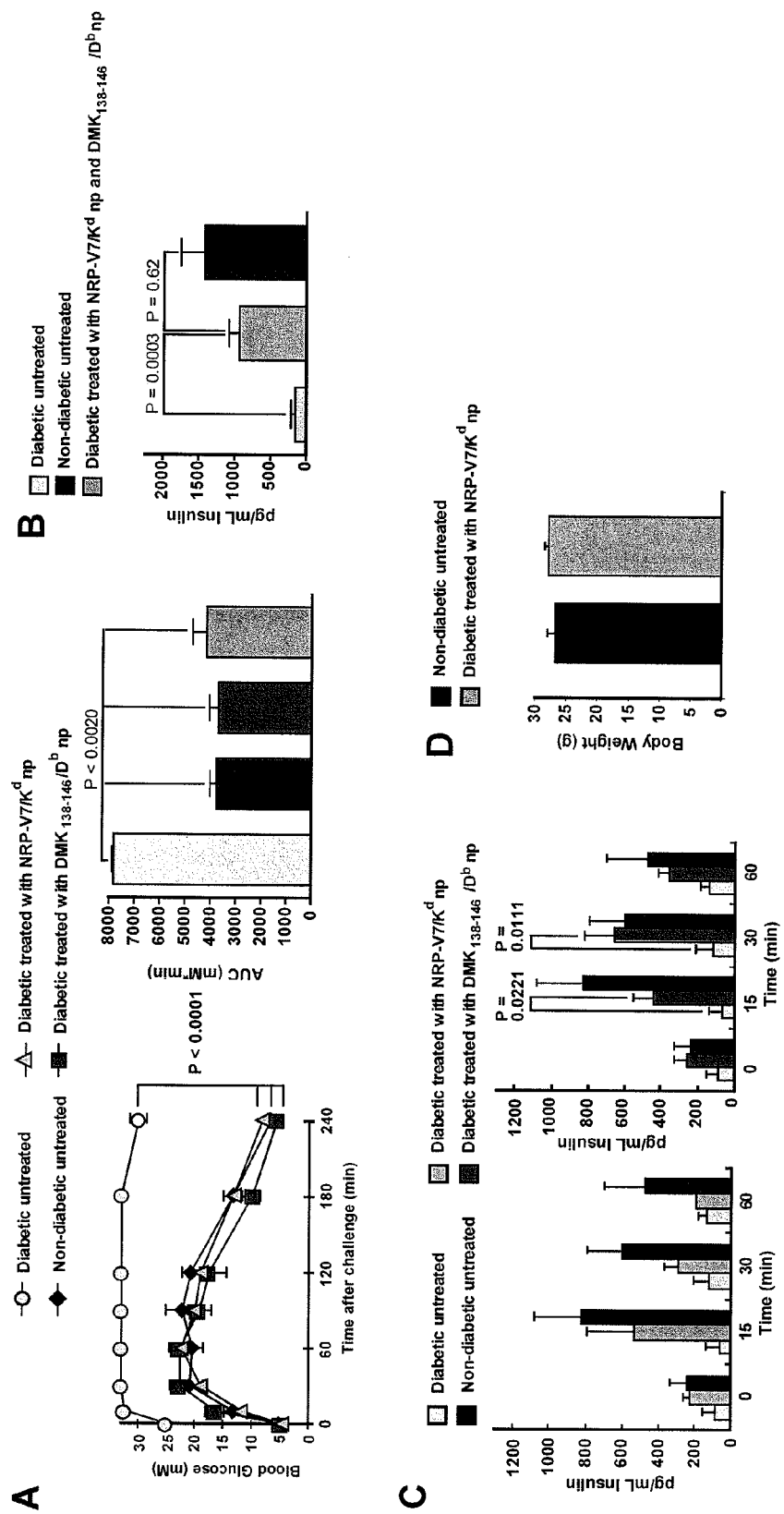
FIGS. 11A-11D. Glucose tolerance in cured mice.

Intraperitoneal glucose tolerance tests (IPGTTs) in cured versus diabetic and non-diabetic untreated mice confirmed that the former had glucose tolerance curves nearly identical to those displayed by non-diabetic untreated animals and significantly better than those corresponding to diabetic mice (FIG. 1A). Furthermore, the cured animals had postprandial serum insulin levels that were statistically comparable to those seen in non-diabetic untreated mice and significantly higher than those corresponding to diabetic untreated animals (FIG. 11B). In agreement with these data, the IPGTT serum insulin levels of NRP-V7/$K^d$-np and $DMK_{138-146}/D^b$-np-treated mice were similar to those of non-diabetic mice and significantly better than those of diabetic untreated animals (FIG. 11C). The cured animals had normal body weights at 50 weeks of age (>25 weeks after reversal of hyperglycemia), as compared to those of age-matched non-diabetic untreated mice (FIG. 11D).

Figure 12:
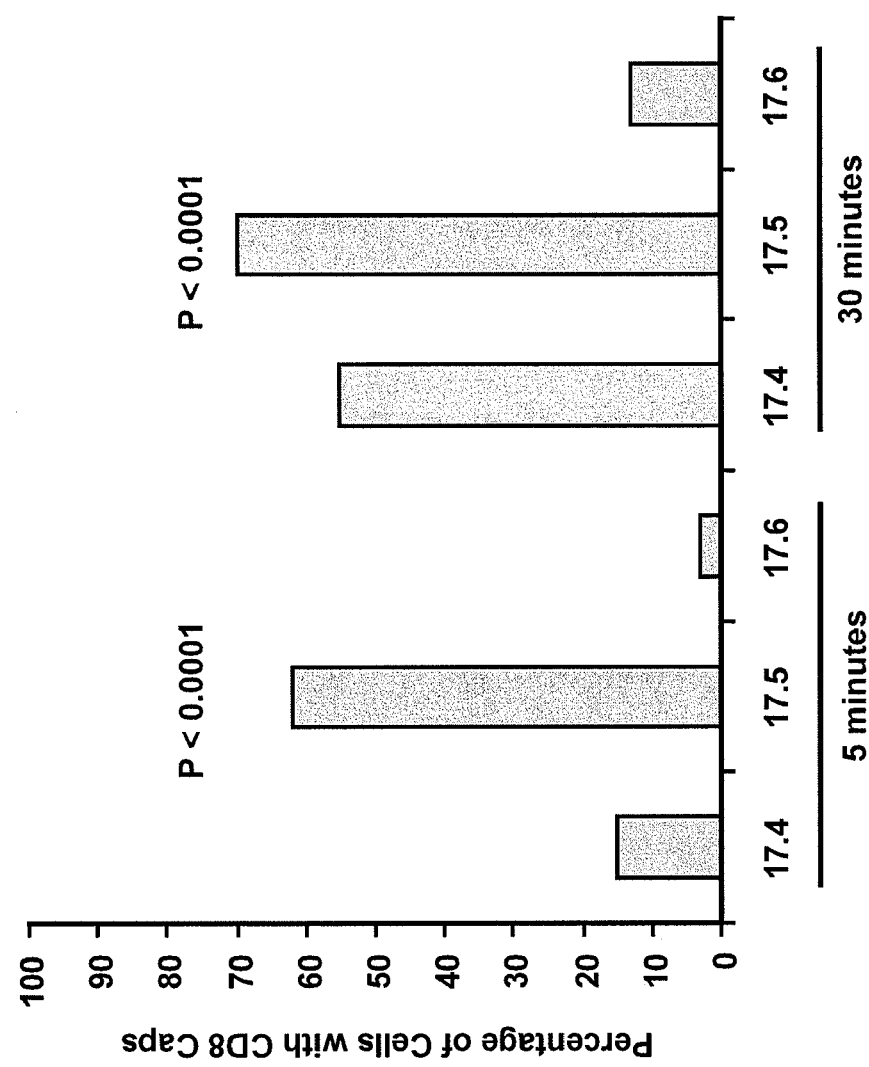
FIG. 12. Peptide/MHC-coated nanoparticles can effectively 'discriminate' between high- and low-avidity autoreactive CD8+ T-cells. The different TCR transfectants were incubated with NRP-V7/K$^d$-coated beads for 5 or 30 minutes and stained with anti-CD8 mAbs. Histograms represent the percentage of cells that had formed CD8 caps at the indicated times after incubation with beads.

Peptide/MHC-coated nanoparticles can effectively 'discriminate' between high- and low-avidity autoreactive CD8+ T-cells. Most $IGRP_{206-214}$-reactive CD8+ cells employ CDR3-invariant Vα17-Jα42 chains but heterogeneous VDJβ chains. 'Avidity maturation' of this T cell subset during diabetogenesis is associated with changes in usage of 3 different Vα17 elements. That these 3 different Vα elements afford differences in ligand-binding avidity (Vα17.5>Vα17.4>Vα7.6) was confirmed in studies of TCRαβ-transfectants expressing the 3 different CDR3-invariant Vα17-Jα42 chains in the context of a single TCRβ chain (Han et al., 2005). To investigate whether peptide/MHC-coated nanoparticles could in fact differentially target T cells recognizing ligand with different avidity, the ability of NRP-V7/$K^d$-coated nanoparticles to induce 'capping' of CD8 molecules on these transfectants was assessed. More than 60% of Vα17.5$^+$ cells, but less than 20% Vα17.4$^+$ or Vα17.6$^+$ cells, had formed caps by 5 min of incubation with NRP-V7/$K^d$-coated beads. By 30 min, the percentage of Vα17.4$^+$ cells with caps approached that seen for Vα17.5$^+$ cells, but this number remained lower than 20% for Vα17.6$^+$ cells (FIG. 12). These results demonstrate that NRP-V7/$K^d$-coated beads can in fact discriminate between high and low-avidity T cell and provide an explanation as to why these nanoparticles preferentially delete naïve high avidity clonotypes. However, they do not explain why these particles expand low avidity clonotypes, particularly if it is assumed that TCR ligation in the absence of costimulation (by peptide/MHC on nanoparticles) would also be expected to delete, rather than expand, low-avidity clonotypes.

Figures 13A, 13B, 13C:
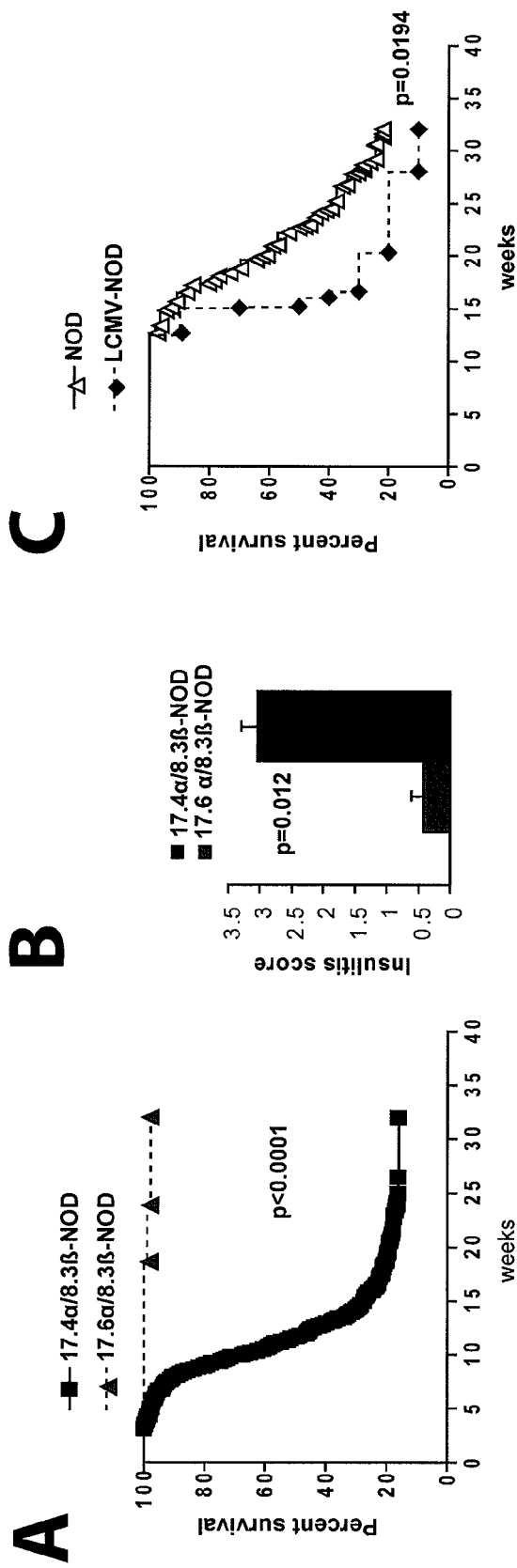
FIGS. 13A-13C. The low affinity autoreactive 17.6α/8.3β CD8+ T cells are anti-diabetogenic.

CD8$^+$ cells expressing the low-affinity Vα17.6/8.3β TCR are anti-diabetogenic. To investigate whether low-avidity autoreactive CD8+ T-cells have anti-diabetogenic properties in vivo, the low affinity IGRP$_{206-214}$-reactive Vα17.6/8.3β TCR were transgenically expressed in NOD mice (referred herein to as 'Vα17.6+'; which as a ~10-fold lower affinity than the 8.3-TCR (Vα17.4+); Teyton and Santamaria, unpublished data). It has been shown that this TCR fosters positive selection of CD8$^+$ cells, but clearly less than the 8.3-TCR (Vα17.4$^+$) (Han et al., 2005). As a result, Vα17.6$^+$ TCR-TG mice contain fewer NRP-V7 tetramer-reactive CD8$^+$ thymocytes and splenocytes than Vα17.4$^+$ TCR-TG mice. Furthermore, the tetramer+ (high and low) CD8+ cells from Vα17.6$^+$ TCR-TG mice secrete less IFN-γ (and IL-2) than those derived from Vα17.4$^+$ TCR-TG mice upon peptide stimulation in vitro, and are inefficient killers of NRP-V7-pulsed RMA-SK$^d$ targets, compatible with their low avidity for ligand (Han et al., 2005; and data not shown). Most importantly, these mice are almost completely protected from diabetes (only 2 of 70 females have developed T1D) and insulitis [scores of <0.4 vs >3 (out of a maximum of 4) in Vα17.6$^+$ vs. Vα17.4$^+$ TCR-TG mice, respectively (P<0.012)] (FIG. 13A and FIG. 13B).

This is in stark contrast to what occurs in NOD mice expressing an irrelevant non-autoreactive TCR that recognizes a LCMV epitope (LCMV TCR-TG NOD mice). As reported previously by Serreze et al. (2001), and confirmed by use herein, these mice develop T1D essentially like wild-type NOD mice and recruit endogenous IGRP$_{206-214}$-reactive CD8+ cells to islets (completely absent in the islets of Vα17.6$^+$ TCR-TG mice) (FIG. 13C). Thus, unlike the Vα17.4$^+$ and LCMV TCRs (pro-diabetogenic and neutral, respectively), the Vα17.6$^+$ TCR appears to have anti-diabetogenic properties.

Figures 14A, 14B:
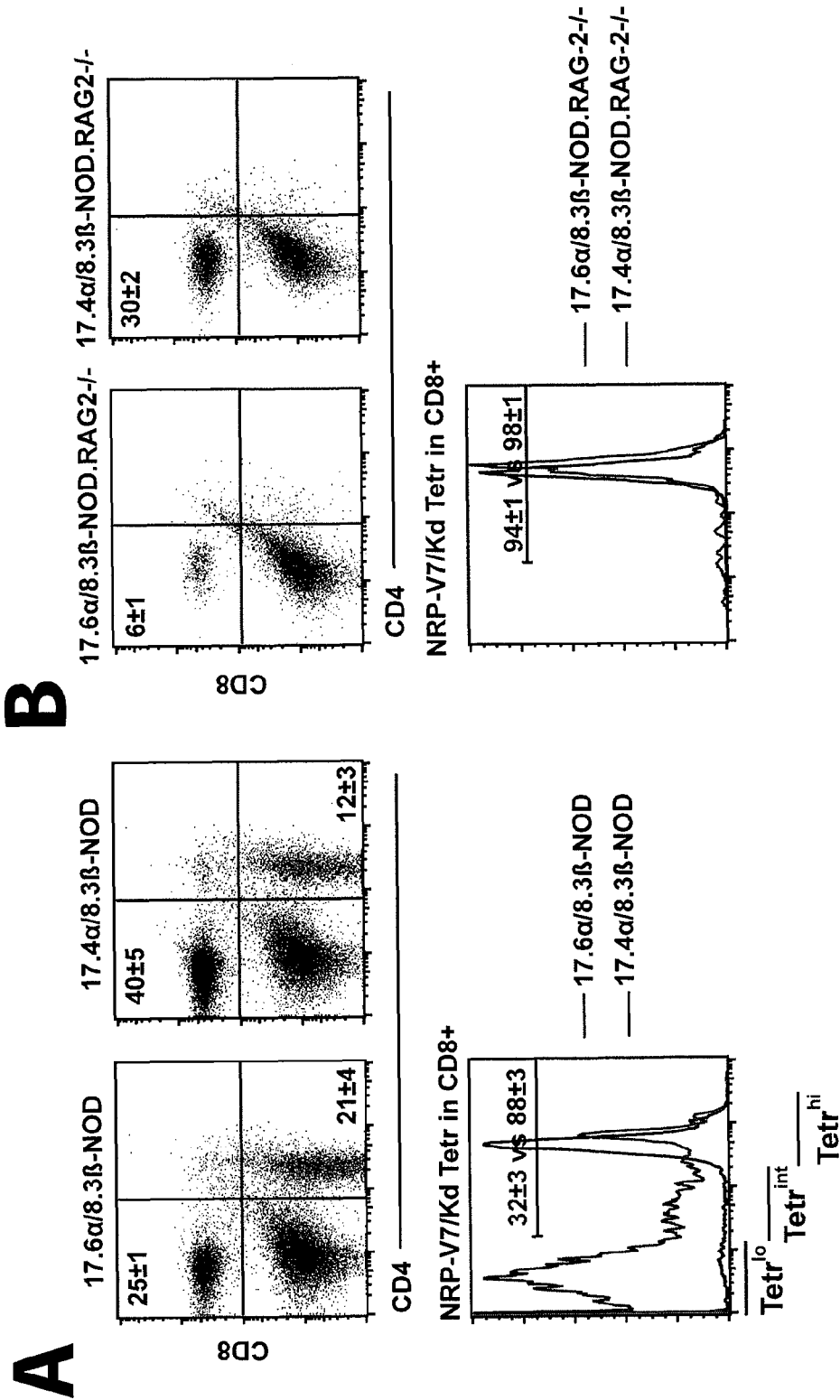
FIGS. 14A-14B. Developmental biology of the 17.6α/8.3β TCR.
Figure 15:
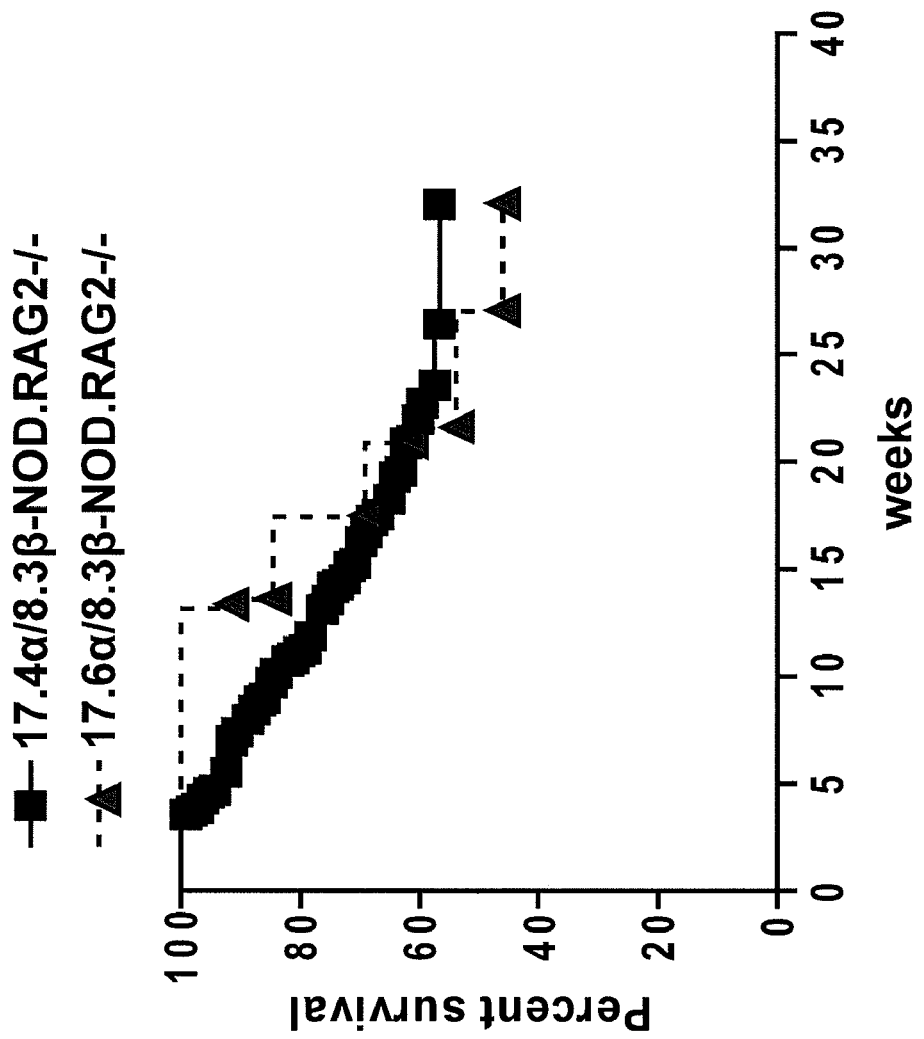
FIG. 15. Frequency of diabetes in 17.6α/8.3β-NOD.RAG-2-/- (n=13) versus 17.4α/8.3β-NOD.RAG-2-/- mice (n=106).
Figure 16A:
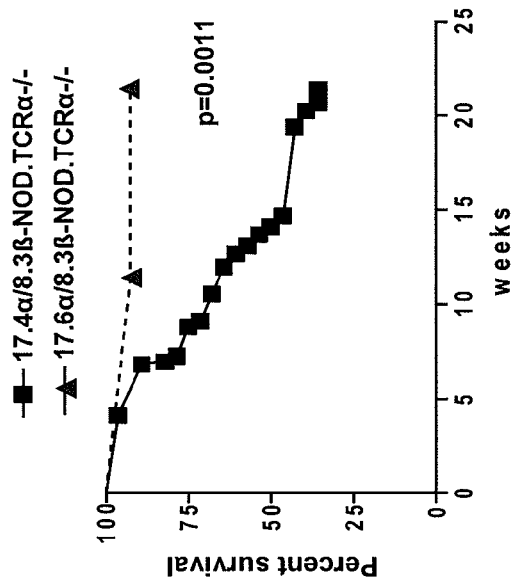
FIGS. 16A-16B. Developmental biology of 17.6α/8.3β versus 17.4α/8.3β TCR in TCRα-/- Tg mice.
Figure 16B:
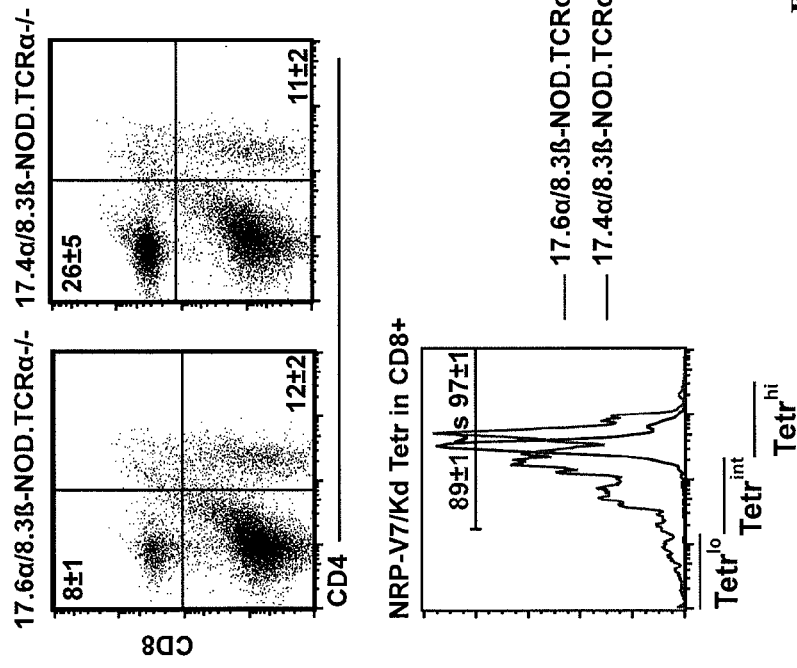

Notwithstanding the fact that most TG T cells of these Vα17.6$^+$ TCR-TG mice bind tetramers weakly or not at all, a fraction of the cells that exit the thymus binds tetramer with apparent high avidity (i.e., with high mfi) (FIG. 14A). The inventors suspected that the tetramer-low (lo) and tetramer-negative CD8$^+$ T cells of these mice originate from CD4$^+$ CD8$^+$ thymocytes that express the TG TCR but undergo positive selection on endogenous TCRs (i.e., TCRα chains). The tetramer-hi cells, on the other hand, would originate from CD4$^+$ CD8$^+$ thymocytes that only express the TG TCRαβ chains and, because of their low affinity for peptide/MHC, can only undergo positive selection if they express higher levels of the TG TCR than normal. This interpretation is supported by the observation that, in mice expressing the Vα17.6$^+$ TCR in a RAG-2$^{-/-}$ background, the only cells that mature are those binding tetramer with high avidity (FIG. 14B). Importantly, these two types of RAG-2$^{-/-}$ TCR-TG mice develop diabetes with similar incidence (FIG. 15). Thus, the inventors suspect that the tetramer-lo and tetramer-CD8$^+$ T cells that mature in RAG-2+Vα17.6 TCR-TG mice inhibit the diabetogenic potential of their tetramer-hi counterparts (which cause diabetes in RAG$^{-/-}$ TCR-TG mice). These results were reproduced in stocks of Vα17.6 TCR-TG mice carrying an endogenous TCR-Cα deficiency that recludes expression of endogenous (i.e., non-transgenic) TCRα chains (FIGS. 16A and 16B).

Figures 17A, 17B, 17C:
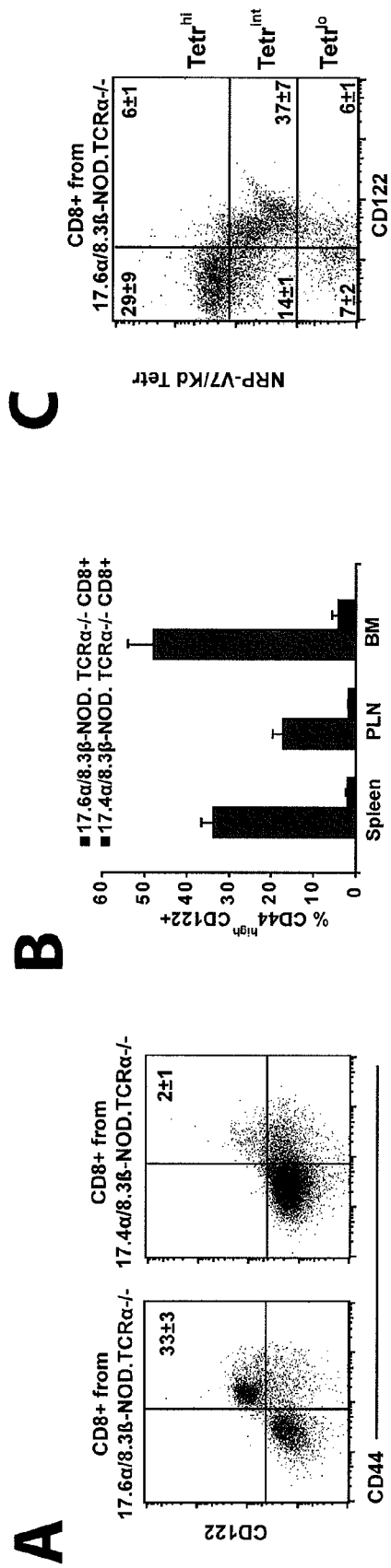
FIGS. 17A-17J. 17.6α/8.3β CD8+ T cells spontaneously differentiate into memory T cells with regulatory function.
Figures 17D, 17E, 17F:
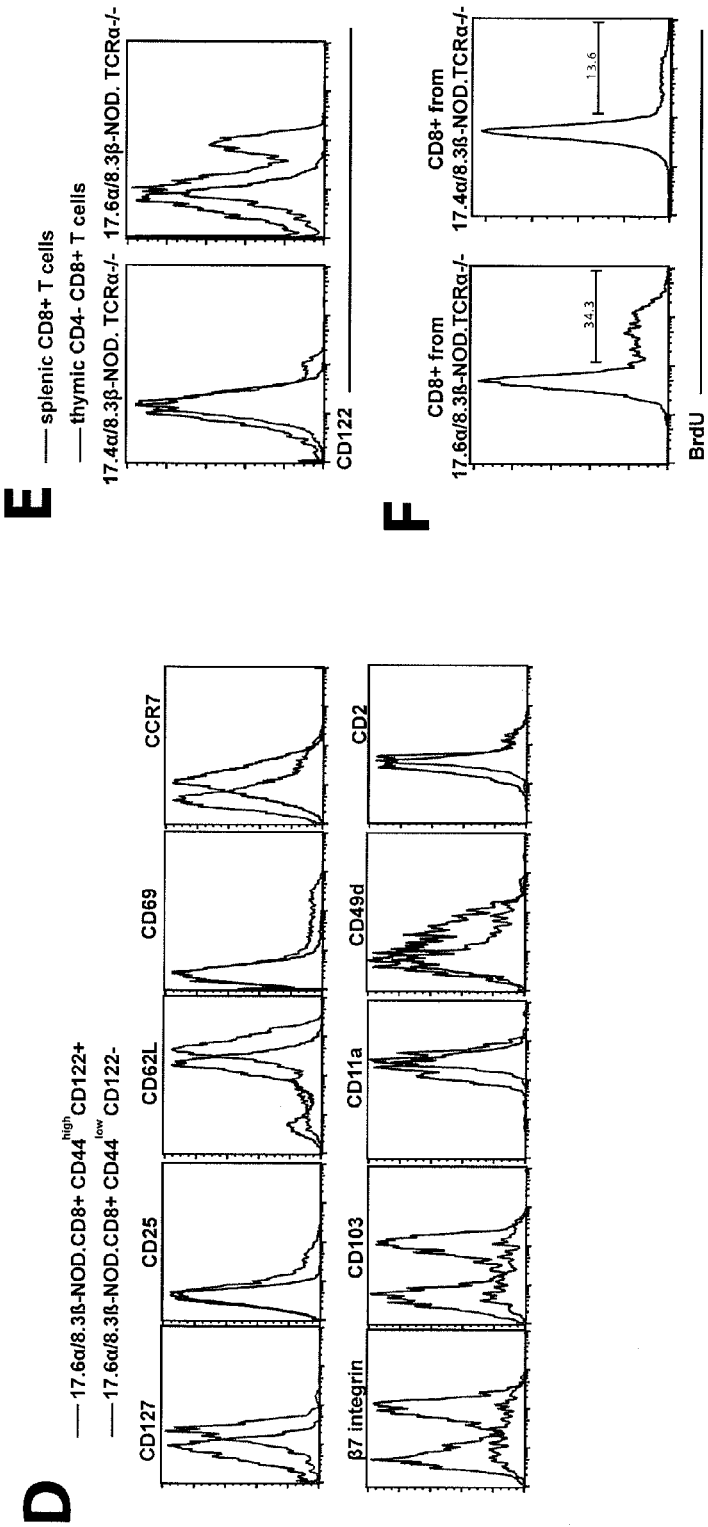
Figures 17G, 17H, 17I:
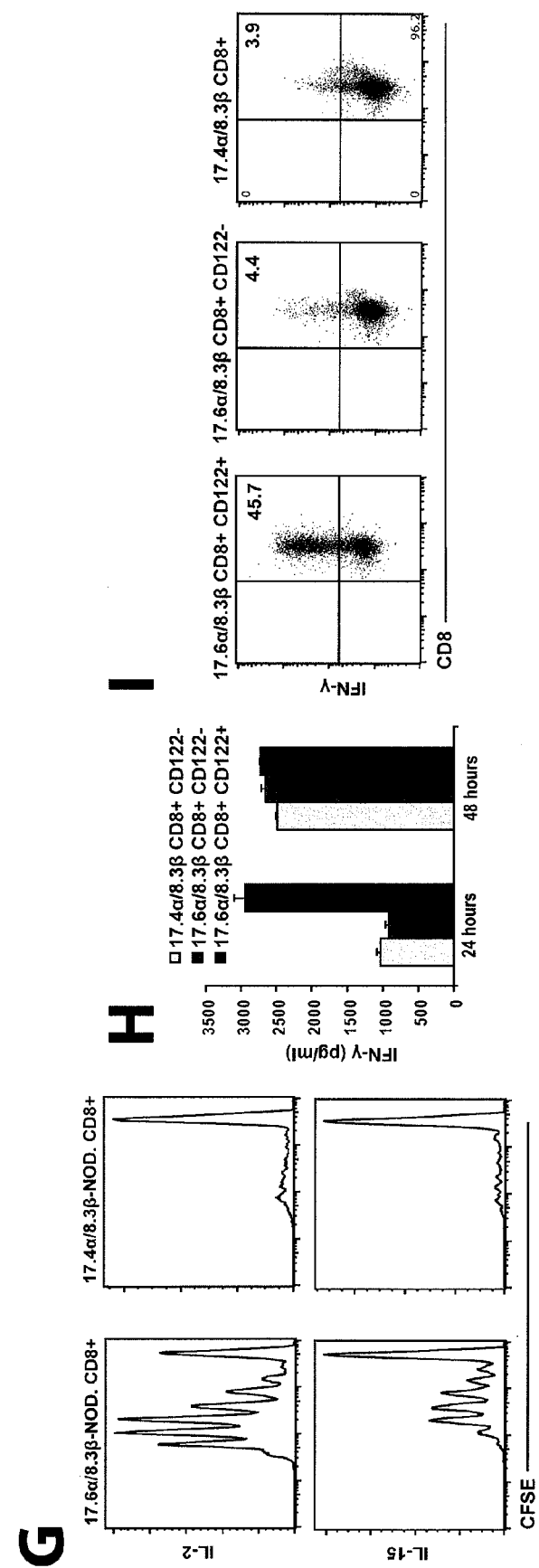
Figure 17J:
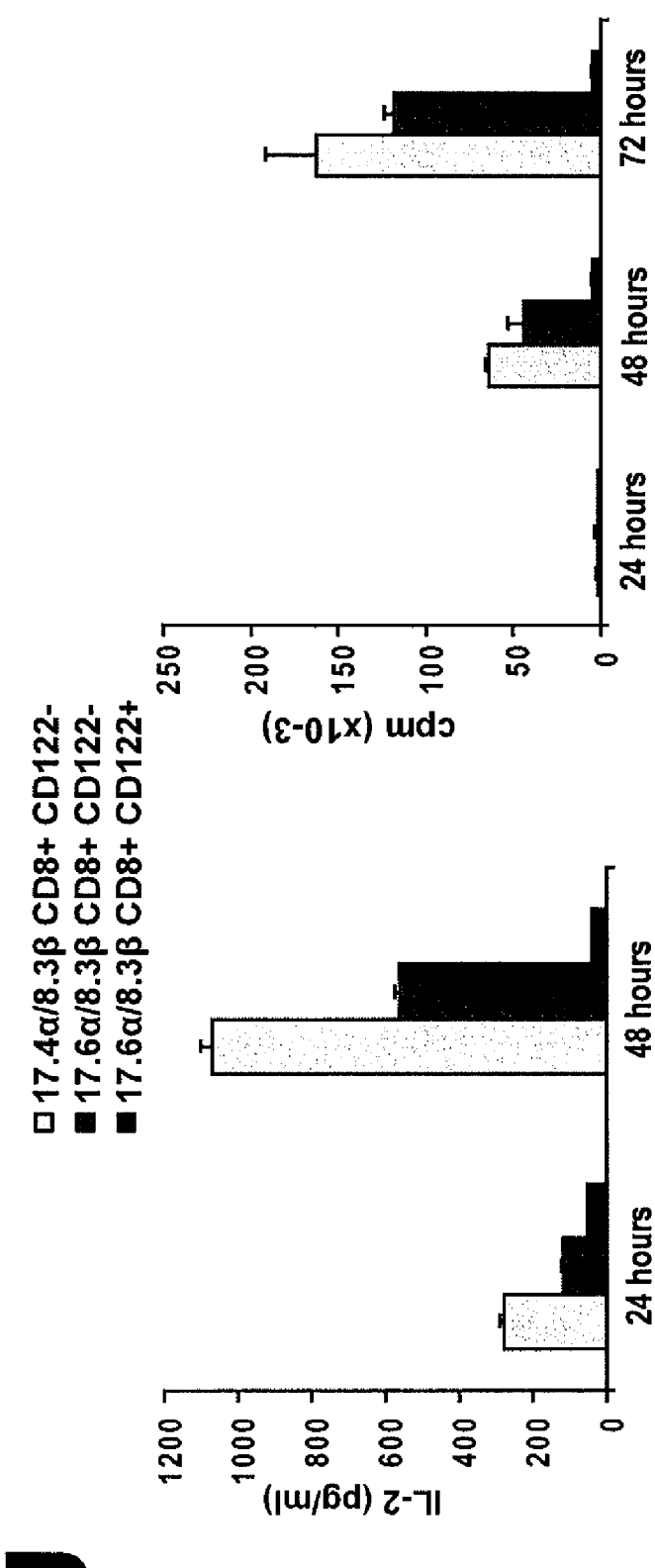

Vα17.6+ (but not Vα17.4+) TCR-TG mice spontaneously generate a pool of memory CD8+ cells with immunosuppressive activities. Cytofluorometric studies of the tetramer-positive CD8$^+$ T-cells contained in the different lymphoid organs of Vα17.6$^+$ TCR-TG mice and TCR-Cα-deficient Vα17.6 TCR-TG mice revealed the presence of enlarged pools of CD44hi and CD44hiCD122$^+$ CD8+ cells as compared to Vα17.4$^+$ TCR-TG mice in the spleen, lymph nodes and, especially, the bone marrow, a known reservoir of memory T-cells (FIGS. 17A and 17B). Importantly, this occurs primarily within the tetramer-low, but not in the tetramer-high subset, which does not contain CD122$^+$ cells (FIG. 17C). These cells express markers described on both central and effector memory lymphocytes (FIG. 17D), are and predominantly found in the peripheral lymphoid organs but not thymus, suggesting a peripheral origin (FIG. 17E). Furthermore, BrdU incorporation assays suggested that they proliferate in vivo (FIG. 17F). Functionally, these memory-like cells clearly behave as 'memory' T-cells, as purified splenic Vα17.6$^+$(but not Vα17.4$^+$) TCR-TG CD8$^+$ cells proliferate vigorously in response to IL-2 or IL-15 in the absence of APCs and antigen (FIG. 17G). Furthermore, they rapidly produce IFN-gamma upon stimulation with antigen in vitro (FIGS. 17H and 17I). However, they neither proliferate nor produce interleukin-2 upon antigenic stimulation in vitro (FIG. 17J). This functional profile is highly reminiscent of that of the regulatory (suppressive) CD4+CD25+ T cell subset. Altogether, these data suggest that Vα17.6$^+$(but not Vα17.4$^+$) TCR-TG CD8+ cells have an increased ability to become long-lived memory T cells (upon one or more antigen encounters), presumably capable of surviving indefinitely in response to homeostatic cues, even in the absence of antigen.

Figure 18:
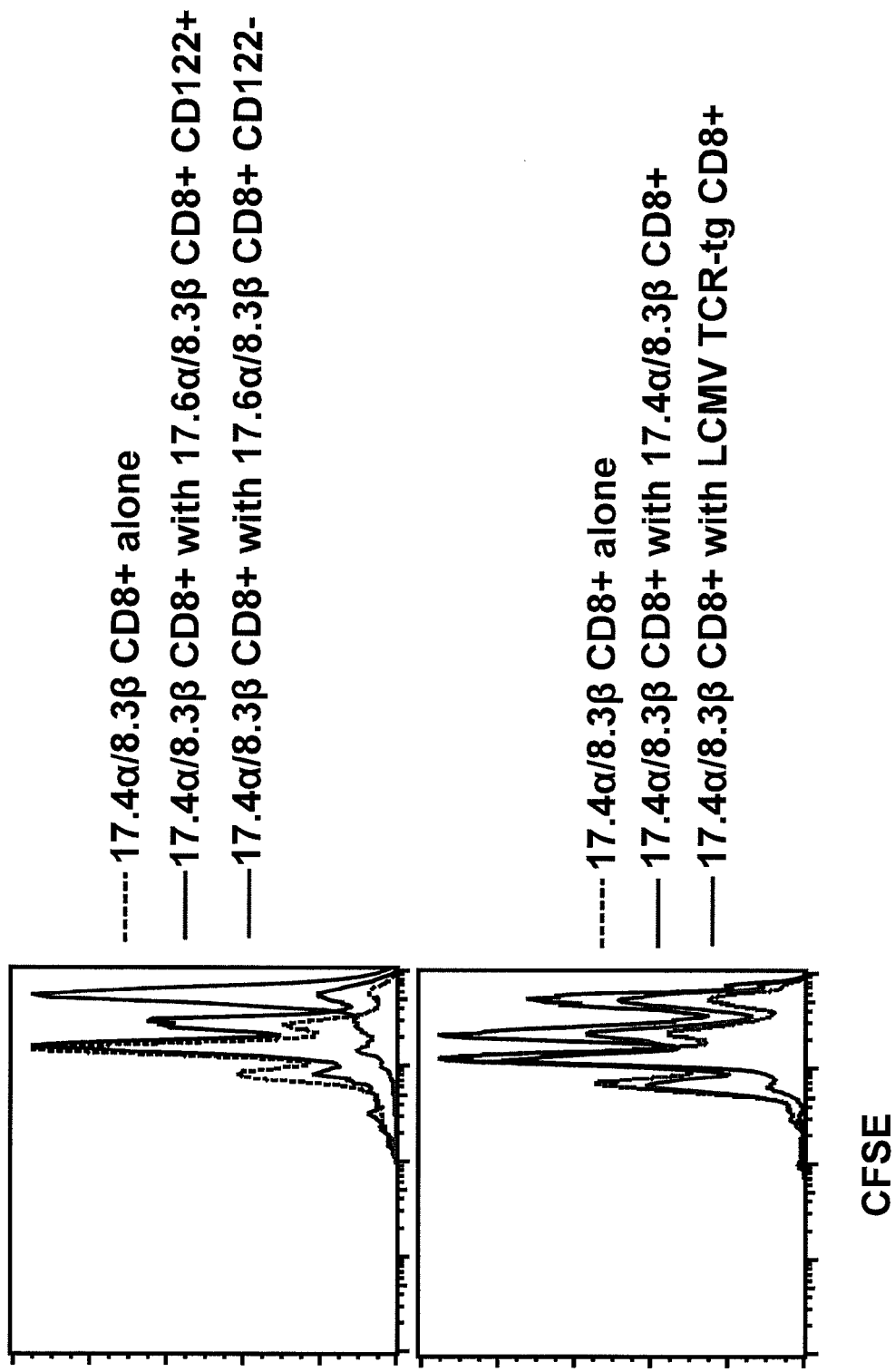
FIG. 18. Proliferation of CFSE-labeled 17.4α/8.3β CD8+ T cells. Proliferation of CFSE-labeled 17.4α/8.3β CD8+ T cells in response to NRP-A7 pulsed DCs in the presence of naïve versus memory CD8+ T cells from 17.6α/8.3β-NOD.TCRα-/- mice (upper panel) or naïve CD8+ T cells from 17.4α/8.3β-NOD versus LCMV-NOD mice (lower panel). Data are representative of at least five experiments.

These observations led the inventors to suspect that the superior homeostatic 'fitness' of these memory low-avidity T cells, otherwise unable to kill beta cells, contributes to their anti-diabetogenic activity (i.e., by affording a competitive advantage over their higher-avidity, but mostly naïve, beta cell killer clonotypes, and/or by inhibiting their activation). To assess the latter, the ability of purified CD122$^+$ and CD122-Vα17.6$^+$ TCR-TG CD8$^+$ T cells were assessed for their ability to inhibit the proliferation of CFSE-labeled splenic CD8$^+$ T cells from Vα17.4$^+$ TCR-TG NOD mice. As shown in FIG. 18, CD122$^+$ (but not CD122-) Vα17.6$^+$ TCR-TG CD8+ T cells almost completely inhibited the proliferation of their higher avidity naïve T cell counterparts.

Consistent with the idea that the spontaneously expanded pool of memory (CD122$^+$) low-avidity autoreactive CD8$^+$ T cells in Vα17.6$^+$ TCR-TG NOD mice is anti-diabetogenic, systemic (i.v.) treatment of Vα17.6$^+$ and Vα17.4$^+$ TCR-TG mice with NRP-V7-pulsed DCs, an agonistic mAb against CD40, or an agonistic mAb against 4-1BB (to enhance CD8+ T cell activation/survival), induced rapid onset of diabetes in Vα17.4+ TCR-TG NOD mice, but were unable to elicit disease in Vα17.6+ TCR-TG mice (Table 4).

TABLE 4

Treatments that promote memory T-cell development and expansion precipitate acute onset of diabetes in 17.4a/8.3b-TG NOD mice, but not in 17.6a/8.3b-TG NOD mice.

| Treatment | Host | Diabetes Incidence | Diabetes onset Day (s.e.) |
|---|---|---|---|
| Agonistic Anti-CD40 mAb | 17.4 NOD | 4/4 | 10.5 (4.6) |
|  | 17.6 NOD | 0/3 | — |
| Agonistic Anti-4-1BB mAb | 17.4 NOD | 3/3 | 2.3 (1.5) |
|  | 17.6 NOD | 0/2 | — |
| NRP-V7 pulsed Dendritic cells | 17.4 NOD | N.A. | — |
|  | 17.6 NOD | 0/3 | — |

Figure 19A:
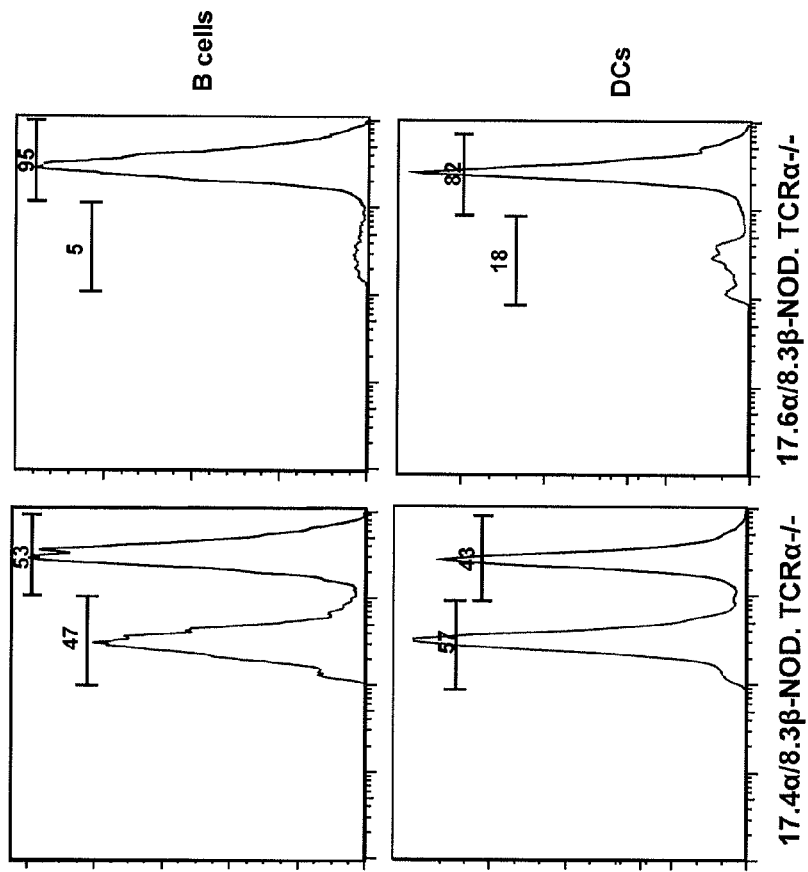
FIGS. 19A-B. Memory 17.6α/8.3β CD8+ T cells kill antigen-pulsed APCs.
Figure 19B:
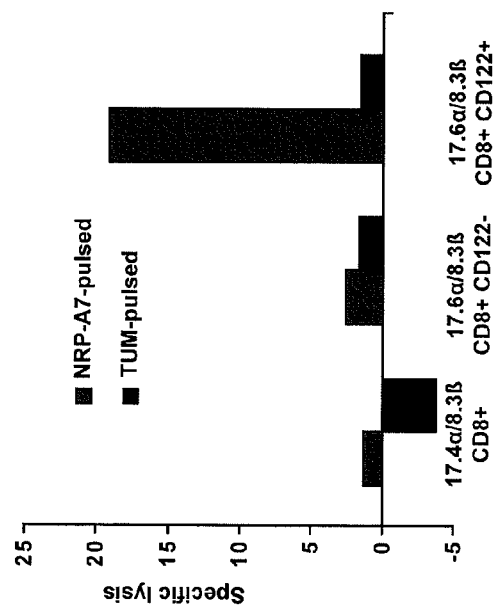

3 injections of Anti-CD40 mAb or Anti-4-1BB mAb 100 µg i.p. with 3-4 days intervals
2 injections of 10⁶ LPS-activated bone marrow-derived DCs pulsed with 100 µg/ml NRP-V7
Mice were followed for diabetes at least 8 weeks after the last injection The ability of $CD122^+$ Vα17.6+ TCR-TG CD8+ T cells to suppress cognate and non-cognate diabetogenic T cell responses (i.e., directed against autoantigenic peptides other than the target autoantigenic peptide of these suppressive T-cells-$IGRP_{206-214}$-), led the inventors to suspect that they might effect their suppressive activity by targeting antigen-presenting cells (APCs). Cytotoxicity ($^{51}$Chromium-release) assays employing peptide-pulsed DCs as target cells and $CD122^+$ or CD122-Vα17.6+ and CD122-Vα17.4+ TCR-TG CD8+ T cells as effectors indicated that the former, but not the latter were able to specifically lyse NRP-V7-pulsed DCs in vitro (FIG. 19A). The inventors confirmed that this was also true in vivo. They transfused equal numbers of NRP-V7-pulsed and TUM-pulsed B-cells (labeled with low or high concentrations of the dye CFSE, respectively) into Vα17.6+ TCR-TG and Vα17.4+ TCR-TG mice and a day later sacrificed the hosts to investigate which cells had survived the transfer. As shown in FIG. 19B, whereas NRP-V7-pulsed B-cells only survived in Vα17.4+ TCR-TG mice, B-cells pulsed with the negative control peptide TUM survived in both TCR-TG strains. Virtually identical results were obtained when DCsm rather than B-cells, were used as APCs (FIG. 19B). These data suggest that low-avidity $CD122^+$ Vα17.6+ TCR-TG CD8+ T cells suppress cognate and non-cognate diabetogenic T cell responses by killing autoantigen-loaded APCs.

NRP-V7/$K^d$-coated nanoparticles induce the expansion of low avidity (tetramer-intermediate) memory autoreactive CD8+ cells in wild-type NOD mice. The above observations in Vα17.6+ TCR-TG NOD mice were highly reminiscent of what was seen in NOD mice treated with peptide/MHC-coated nanoparticles: disappearance of high avidity clonotypes, and expansion and recruitment of low-avidity CD8+ T cells, impaired recruitment of other IGRP epitope-reactive specificities to islets, and protection from diabetes.

Figure 20A:
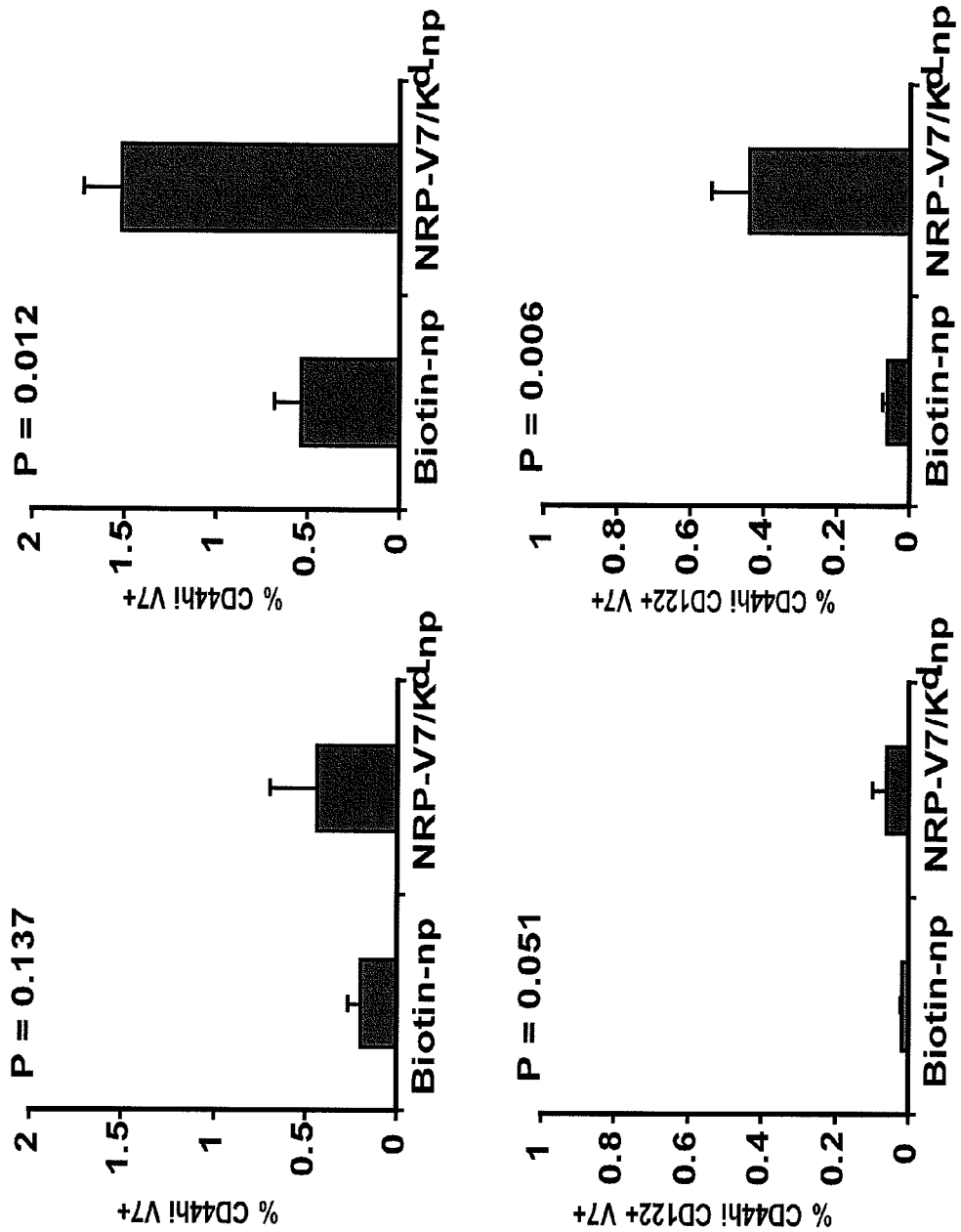
FIGS. 20A-20D. NRP-V7/K$^d$-np- or DMK$_{138-146}$/D$^b$-np-expanded tetramer+CD8+ cells have suppressive activity.

To assess whether the bead-expanded CD8+ T cells in wild-type NOD mice were long-lived low avidity memory T cells, the inventors analyzed the presence of memory markers (CD44 and CD122) in the NRP-V7/$K^d$ tetramer-positive CD8+ T-cells contained in the spleen bone marrow of mice treated with NRP-V7/$K^d$-coated nanoparticles. The expanded populations of tetramer-positive cells contained in the spleen and marrow of these mice contained increased percentages of CD44hi and CD44hiCD122+ CD8+ T-cells, particularly in the bone marrow (FIG. 20A), confirming that NRP-V7/$K^d$ nanoparticle treatment increases the size of the tetramer+ CD44hi and tetramer+ CD44hiCD 122+ T cell pools.

Figure 20B:
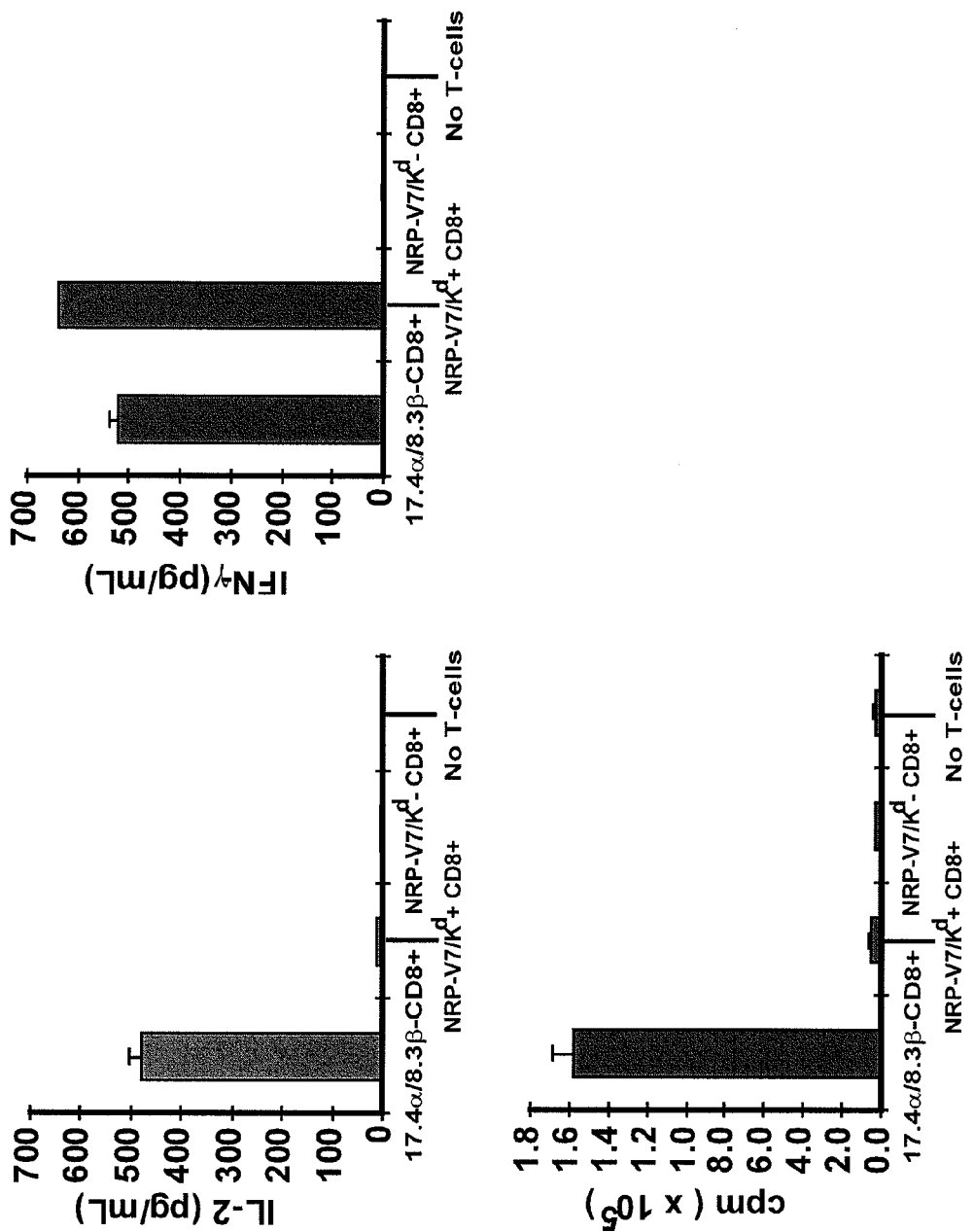
Figure 20C:
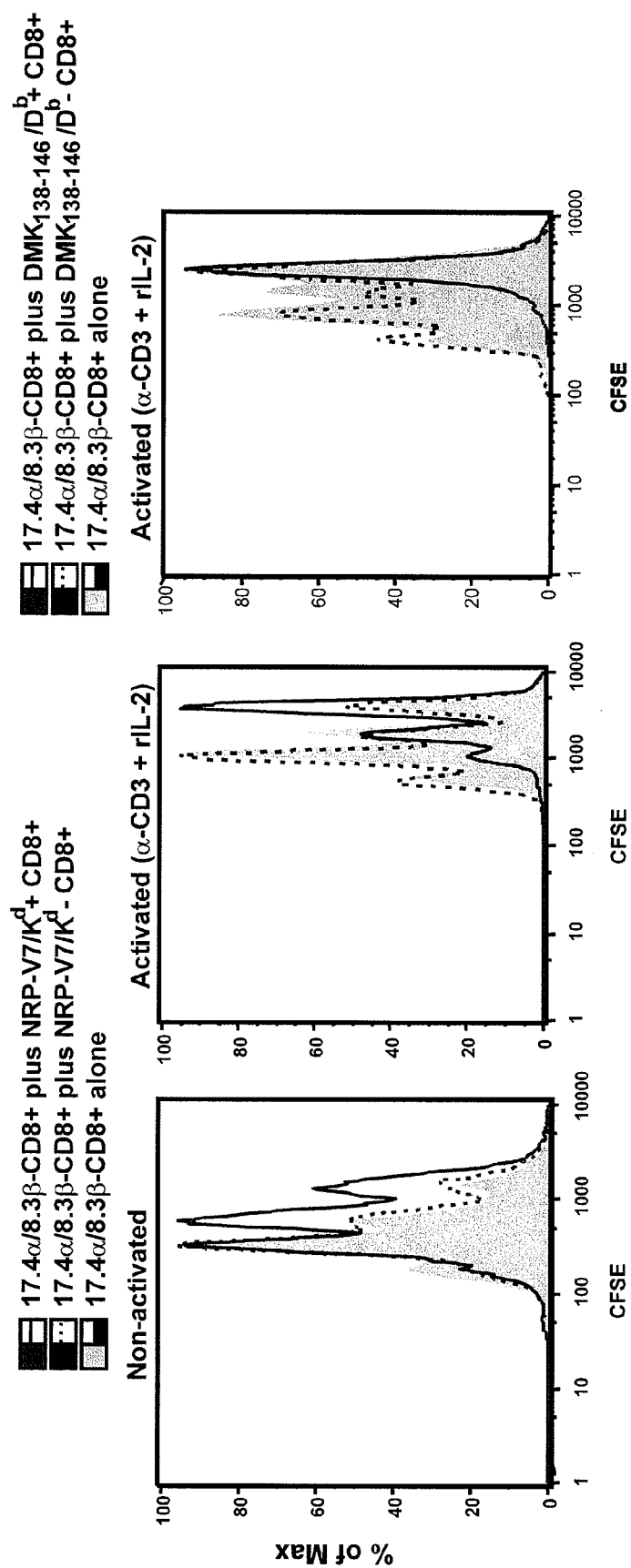
Figure 20D:
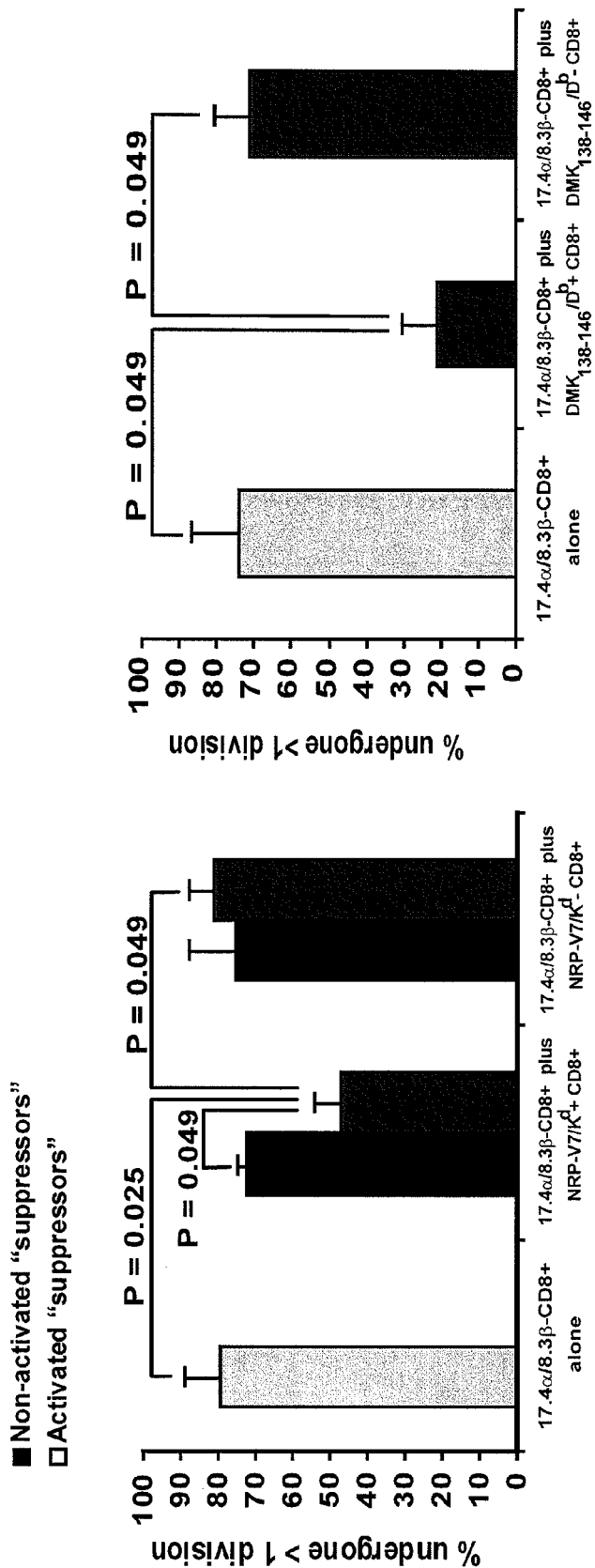

Functionally, the memory-like T-cells that are expanded by in vivo therapy with NRP-V7/$K^d$-coated nanoparticles behave like the memory $CD122^+$ Vα17.6+ TCR-TG CD8+ T cells that spontaneously accumulate in Vα17.6+ TCR-TG mice: they neither produce IL-2 nor proliferate, yet produce high levels of IFN-gamma in response to antigenic stimulation in vitro (FIG. 20B). Most importantly, upon activation with anti-CD3 mAb and IL-2, these memory-like T-cells efficiently suppressed the proliferation of CFSE-labeled responder Vα17.4+ TCR-TG CD8+ T-cells in vitro (FIG. 20C). Suppression was not simply due to competition for peptide, because CFSE-labeled responder Vα17.4+ TCR-TG CD8+ T-cells also failed to proliferate in the presence of memory-like T-cells expanded by treatment with $DMK_{138-146}$/$D^b$-coated nanoparticles (FIG. 20D).

Figures 21A, 21B:
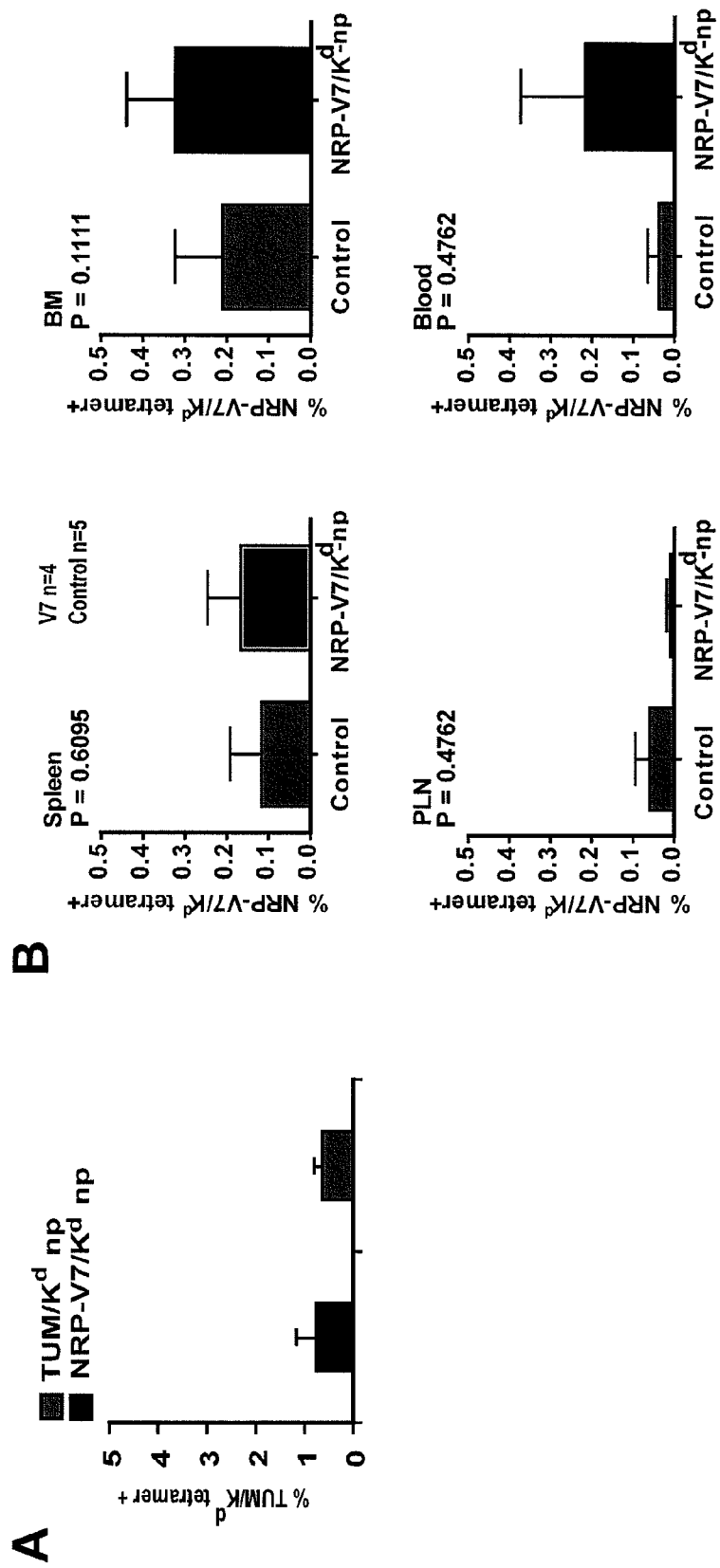
FIGS. 21A-21C. Peptide/MHC-coated nanoparticles expand pre-existing low-avidity memory T cells.
Figure 21C:
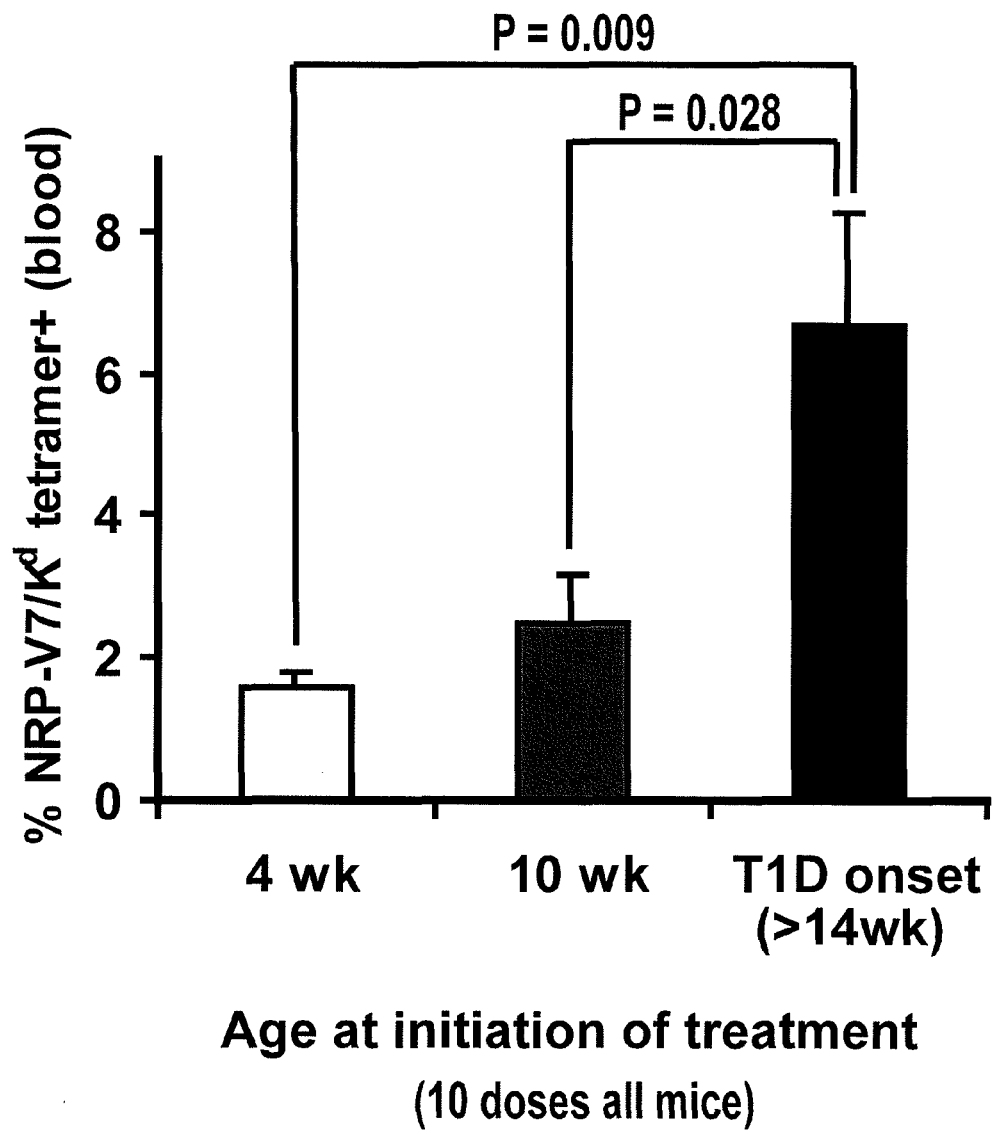

Peptide/MHC-coated nanoparticles expand pre-existing low-avidity memory T cells. Several observations suggest that peptide/MHC-coated nanoparticles do not generate memory T-cells de novo, but rather expand pre-existing pools of memory T cells: (i) treatment of NOD mice with TUM/$K^d$-coated nanoparticles did not induce systemic expansion of TUM-reactive CD8+ T cells (recognizing a tumor-specific antigen, not expressed in NOD mice; FIG. 21A); (ii) Treatment of B 10.H2g7 mice, which develop neither diabetes nor insulitis, with NRP-V7/$K^d$-coated nanoparticles failed to induce a significant expansion of the NRP-V7/$K^d$ tetramer+ CD8+ T-cell subset in all lymphoid organs examined (FIG. 21B); (iii) Systemic expansion of tetramer-reactive CD8+ T-cells in nanoparticle-treated NOD mice was significantly more effective when initiated at diabetes onset than in the pre-diabetic stage (FIG. 21C); and (iv) unlike naïve CD8+ T cells, which tend to undergo apoptosis upon TCR ligation in the absence of costimulation, memory CD8+ T cells are costimulation-independent for growth.

Figure 22A:
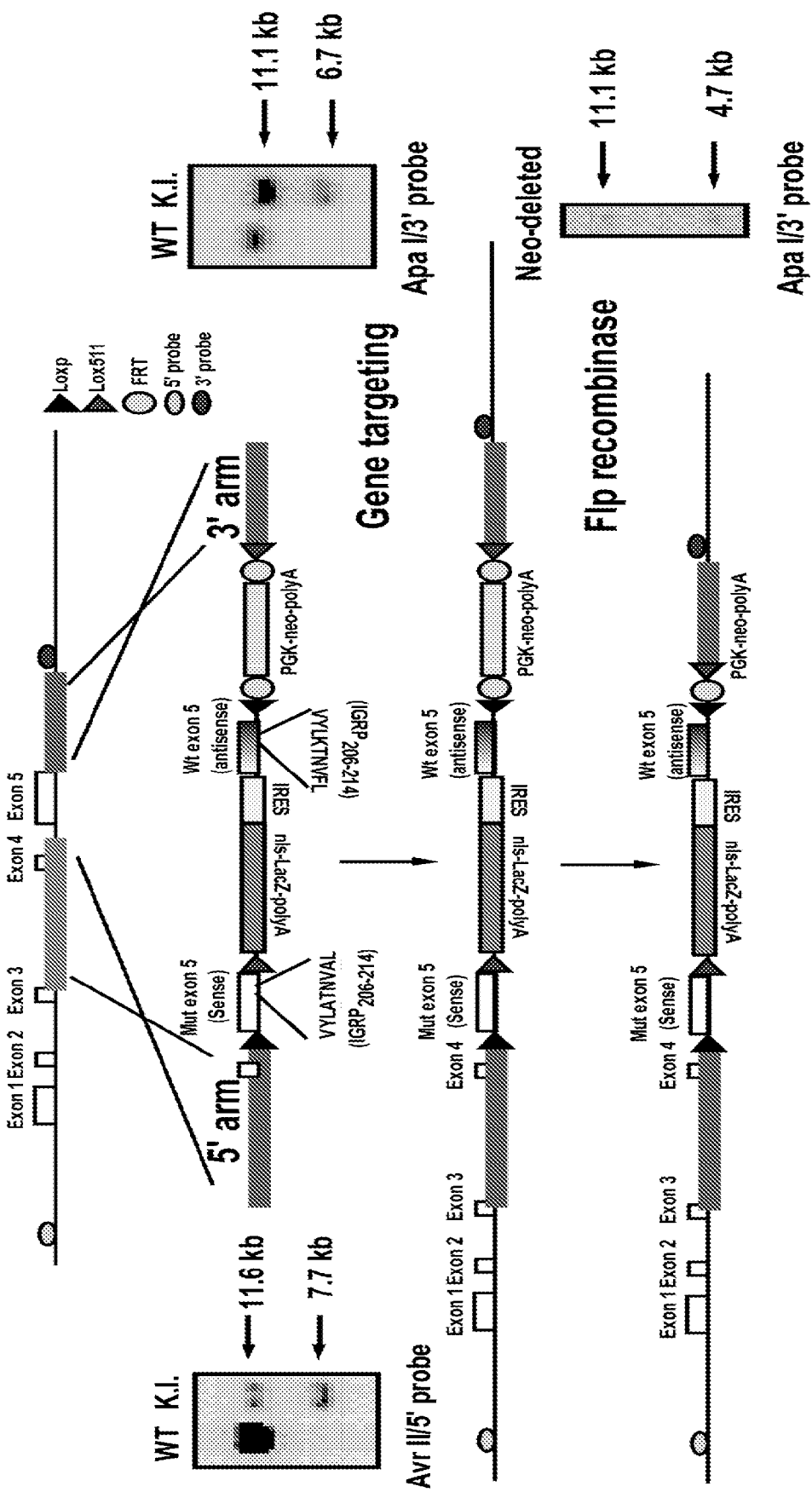
FIGS. 22A-22C. The protective effect of NRP-V7/$K^d$-np and $DMK_{138-146}/D^b$-np treatment requires the expansion of pre-existing low-avidity, tetramer+ CD8+ T cells.
Figure 22B:
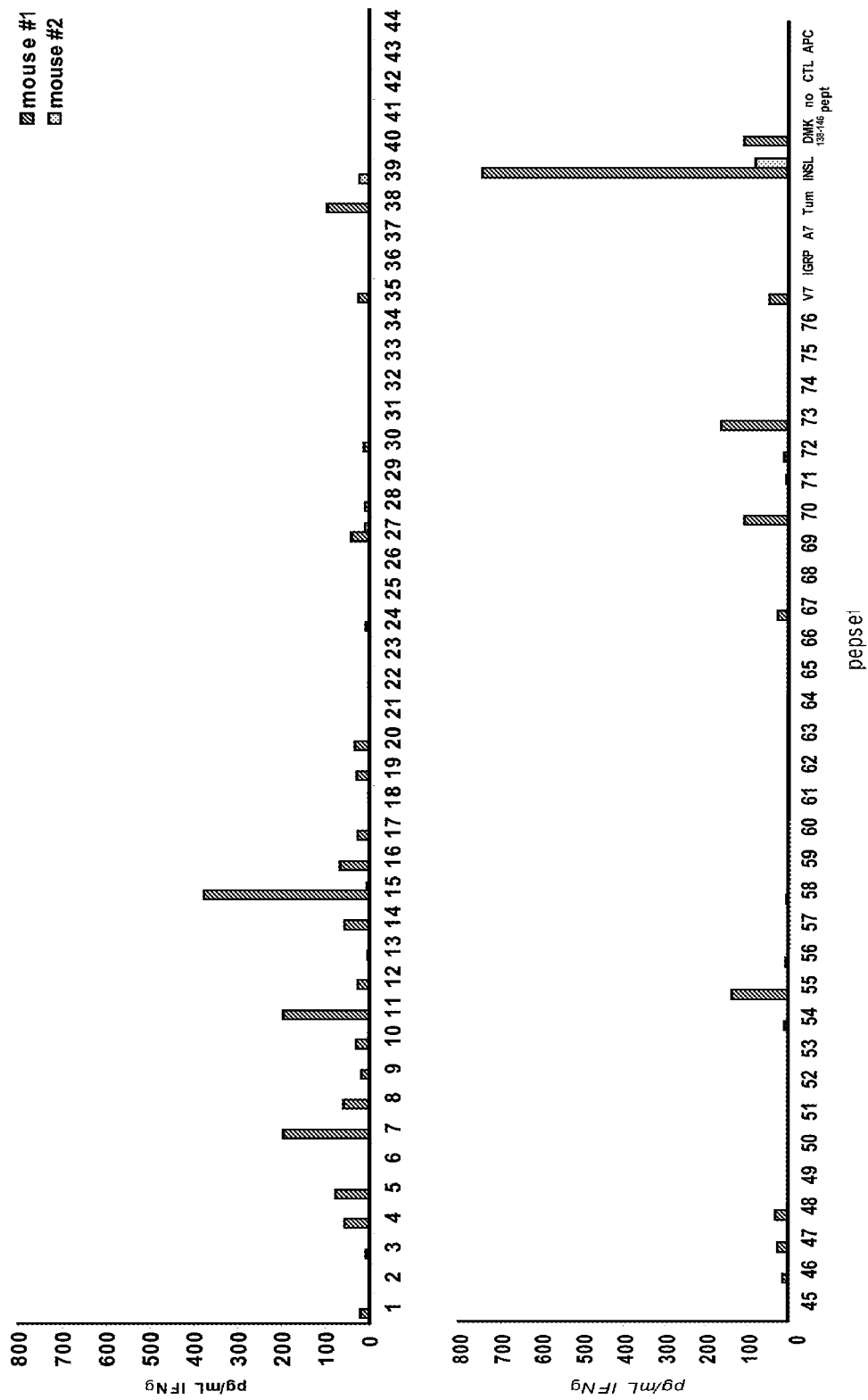
Figure 22C:
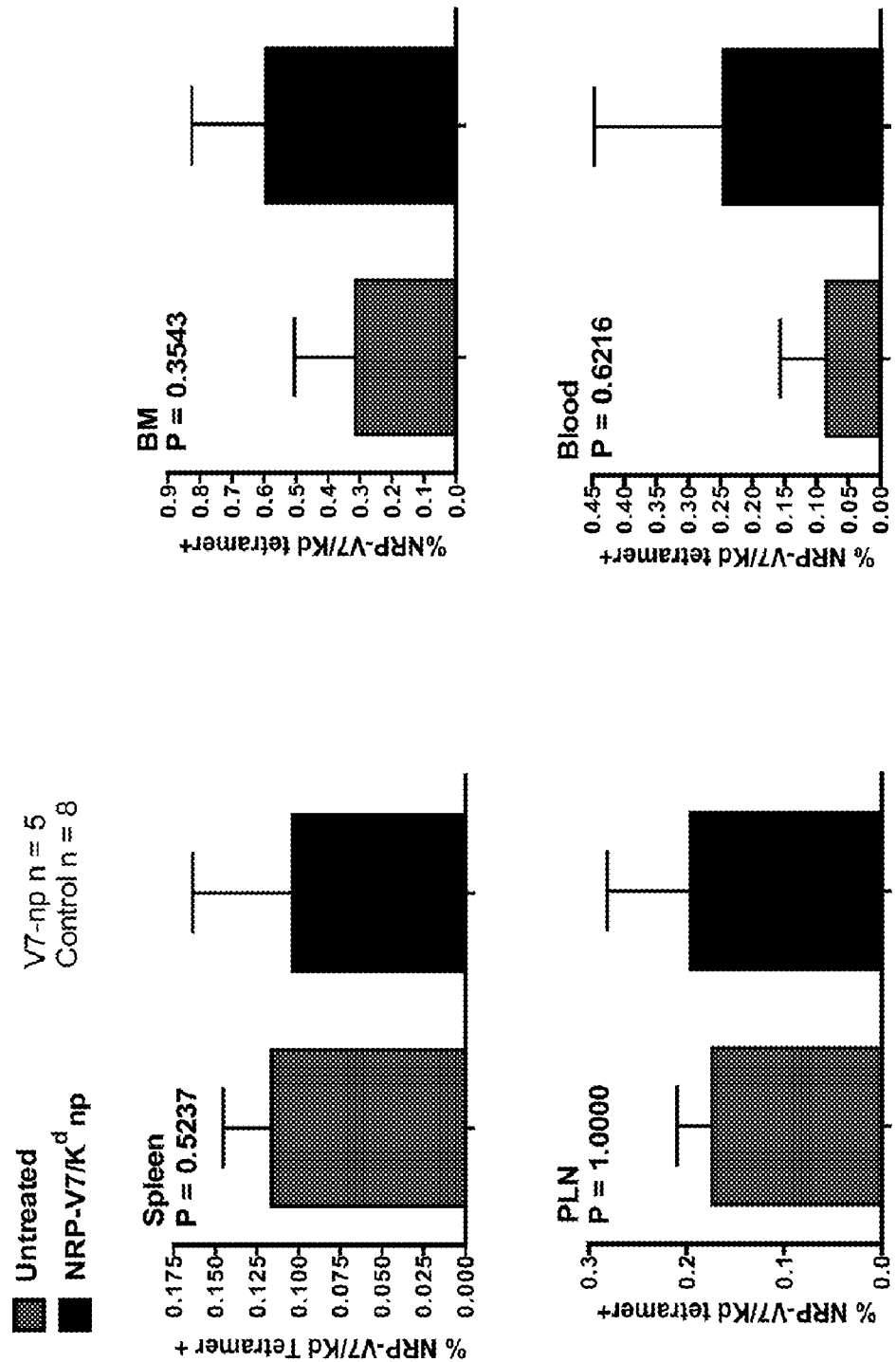

To investigate the above hypothesis formally, the inventors asked whether $IGRP_{206-214}$/$K^d$-coated nanoparticles could expand $IGRP_{206-214}$/$K^d$-reactive CD8+ T-cells in a gene-targeted NOD strain that expresses a mutant form of IGRP in which the two TCR-contact residues of $IGRP_{206-214}$ have been replaced with alanines (K209A and F213A) (FIG. 22A). The targeted alleles (herein referred to as FLEX1 or NOD.$IGRP_{K209A/F213A}^{KI/KI}$) were backcrossed onto the NOD background (from 129) using the speed-congenic approach, to ensure homozygosity for NOD alleles at all Idd loci. Because the CD8+ T-cells that mature in these gene-targeted mice are never exposed to $IGRP_{206-214}$ in vivo, these mice cannot spontaneously generate memory $IGRP_{206-214}$/$K^d$-reactive CD8+ T-cells. Despite the fact that these mice develop both diabetes and insulitis (not shown), their islet-associated CD8+ T-cells recognize epitopes in IGRP, but are completely devoid of $IGRP_{206-214}$-reactive CD8+ clonotypes. Most importantly, FLEX1-homozygous NOD mice treated with optimal doses of $IGRP_{206-214}$/$K^d$-coated particles did not contain expanded pools of $IGRP_{206-214}$/$K^d$-reactive CD8+ T-cells in their lymphoid organs (FIG. 22B). These data provide formal proof that peptide/MHC-coated nanoparticles expand pre-existing pools of memory T-cells with suppressive properties and cannot generate memory T-cells de novo.

Since low-avidity clonotypes (i.e., in Vα17.6+ TCR-TG mice) appear to be more efficient at generating memory T-cell progeny than their high-avidity counterparts (i.e., in Vα17.4+ TCR-TG mice) during diabetogenesis, it was concluded that peptide/MHC-coated particles work by inducing the deletion of naïve high-avidity clonotypes and the expansion of small pools of pre-existing memory low-avidity clonotypes.

EXAMPLE 2

Testing the Ability of Iron Oxide Nanoparticles Coated with Human Type 1 Diabetes-Relevant Peptide/HLA Complexes to Restore Normoglycemia "Humanized" mice expressing HLA transgenes and peptide/HLA complexes available for the proposed studies. As mentioned above, peptides derived from insulin and IGRP are primary targets of CD8+ T cells in wild-type NOD mice. Assessment of human MHC molecules (Human Leukocyte Antigens, HLA) presented peptides derived from these two autoantigens during diabetogenesis is being investigated in 'humanized' HLA-transgenic NOD mice. Studies focused initially on HLAA*0201, a MHC molecule that is expressed by nearly 50% of certain ethnic groups. This study employs the strain designated NOD.$\beta$2m$^{null}$.HHD, which lacks the murine $\beta$2 macroglobulin gene and expresses the chimeric monochain construct HHD (Pascolo et al., 1997). This construct encodes human $\beta$2m covalently linked to the $\alpha$1 and $\alpha$2 domains of human HLA-A*0201, and the $\alpha$3, transmembrane, and cytoplasmic domains of murine H-2D$^b$. Though the strain expresses only HLA-A*0201, and not endogenous murine class I MHC molecules, it is diabetes-susceptible, with 55% of females affected by 30 weeks of age (Takaki et al., 2006). Two epitopes of human IGRP (hIGRP$_{228-236}$ and hIGRP$_{265-273}$) that bind to HLA-A*0201 are recognized by islet-associated CD8+ T cells of these mice and CD8+ T cells isolated from the islets of NOD.$\beta$2m$^{null}$.HHD mice are cytotoxic to human HLA-A*0201-positive islets (Takaki et al., 2006). Peptide/HLA-A*0201 tetramers were made using one of these peptides. To facilitate binding of these tetramers by murine CD8 molecules, the $\alpha$3 (CD8-binding) domain of the HLA-A*0201 complex was replaced with that of the murine H-2K$^b$ molecule. Results from these studies have established the utility of these mice for the identification of HLA-A*0201-restricted T cells and beta cell autoantigens of potential relevance to human T1D (Takaki et al. 2006). Based on the current disclosure, one can identify the human peptides that are targeted by HLA-A*0201-restricted T cells from T1D patients. In addition, the inventors have generated NOD mice expressing HLA-A*1101, HLA-B*0702, or HLA-Cw*0304. These mice also have murine $\beta$2m replaced with human $\beta$2m by crossing them with the NOD.$\beta$2m$^{null}$.h$\beta$2m strain (Hamilton-Williams et al., 2001). All three HLA transgenes express well, and all three of the HLA-transgenic strains are diabetes-susceptible. Taken together HLAs from these "humanized" animals are representative of the four different HLA supertypes HLA-A2, HLA-A3, HLA-B7, and HLA-C1, respectively (Sidney et al., 1996; Doytchinova et al., 2004). The gene frequencies of HLA-A*1101, HLA-B*0702, or HLA-Cw*0304 alleles can be as high as 23%, 11%, or 10%, respectively, depending on the ethnic group examined (Cao et al., 2001). Coverage of the population can be over 90%, depending on the ethnic group considered, when all four supertypes are targeted (Sidney et al., 1996; Doytchinova et al., 2004; Cao et al., 2001). This consideration is significant in regard to translation of these studies to humans. These animals as well as the previously described NOD.$\beta$2m$^{null}$.HHD strain are available for further studies.

In this Example the inventors propose a design on how to translate these observations in wild-type NOD mice to 'humanized' HLA-transgenic NOD mice. The objective is to investigate if treatment with nanoparticles coated with several different peptide/HLA complexes targeting pools of autoreactive CD8+ T cells relevant to human T1D can protect the mice from diabetes as well as restore normoglycemia in their newly-diagnosed counterparts. The inventors have shown that repeated treatment of NOD mice with small doses of nanoparticles coated with H-2K$^d$ or H-2D$^b$ molecules presenting epitopes targeted by prevalent and non-prevalent autoreactive CD8+ T cell specificities, respectively, induced peptide-specific expansion of memory low-avidity autoreactive CD8+ T cells that were capable of preventing T1D development in wild-type NOD mice and of restoring normoglycemia in newly diagnosed diabetic NOD mice. Here the inventors present a translational approach to identify T1D-relevant peptide/HLA combinations for use in human T1D. Specifically, the inventors contemplate that nanoparticles coated with different T1D-relevant autoantigenic peptide/HLA-A*0201 complexes will afford diabetes protection and cure T1D in NOD.$\beta$2m$^{null}$.HHD mice (expressing HLA-A*0201). One of skill in the art can use this disclosure for use with other epitopes related to other autoimmune diseases, using compositions and methods similar to those used with insulin and/or IGRP epitopes presented by other HLA molecules in 'humanized' HLA-transgenic mice to islet-associated CD8+ T cells, to include other compositions and methods. One of skill will be able to identify the minimal treatment conditions and the type of peptide/HLA complexes that will afford maximum therapeutic benefits, as well as the requirement for pre-therapeutic existence of memory low-avidity CD8+ T cells for therapeutic success and identification of additional peptide/HLA combinations covering as many individuals in different ethnic groups as possible.

Nanoparticle synthesis. Nanoparticles are synthesized and characterized at the physical and chemical levels essentially as described previously (Moore et al., 2004), but using biotinylated peptide/HLA-A*0201 monomers. The MHC molecule of the complex is composed of human $\beta$2 microglobulin and a chimeric form of human HLA-A*0201 in which its $\alpha$1 and $\alpha$2 domains are fused to the $\alpha$3 domain of murine H-2K$^b$ (to facilitate recognition by the murine CD8 molecule). As autoantigenic peptides several different insulin and IGRP derivatives (such as, for example, hIns$_{B10-18}$, hIGRP$_{228-236}$ and hIGRP$_{265-273}$) are used that have been shown to be recognized by islet-associated CD8+ T cells in the context of HLA-A*0201. Biotinylated peptide/HLA-A*0201 monomers are added at a molar ratio of 4 moles of biotin per mole of avidin. Biotinylated proteins are added in multiple portions (about 0.4 moles biotin per avidin) over a period of 24 hours at 4° C. with slow stirring (10 rpm). The resultant probes are purified on a magnetic separation column (Milteny Biotec). A monomer consisted of an unrelated HLA-A*0201-binding peptide complexed with HLA-A*0201 molecules are used for the synthesis of negative control probe. Nanoparticle size, relaxivity (change in relaxation rate per mM), number of biotin binding sites, and iron and protein content are measured.

Administration of nanoparticles. Cohorts of 10-15 female NOD.$\beta$2m$^{null}$.HHD mice are treated with nanoparticles coated with each of the different peptide/HLA complexes referred to above or a negative control peptide (influenza)/HLA complex (0.01, 0.05, 0.1, 0.5 and 1 μg peptide equivalents, one dose every 3 wk from 4 to 30 wk of age, or two doses/week starting at 10 weeks of age for 5 consecutive weeks). Peripheral expansion of antigen-specific CD8+ T cells are documented by staining blood mononuclear cells with anti-CD8 mAb and peptide/MHC tetramers (before initiation of treatment and at treatment withdrawal). Mice are killed at the onset of hyperglycemia or at the end of the study.

Individual mice are studied by multicolor flow cytometry for presence of central and/or effector memory (CD69−, CD44$^{hi}$, CD62L$^{hi}$ or CD62L$^{lo}$, CD122+, Ly6C+) tetramer+ CD8+ T cells in different lymphoid organs (spleen, lymph nodes), bone marrow (a known reservoir of memory T cells), liver, lung and islets. Tetramer-binding avidity is measured as described (Han et al., 2005; Amrani et al., 2000). The inventors contemplate that treatment induces systemic expansion of low-avidity central and effector memory tetramer+ CD8+ cells and preferential (but not exclusive) accumulation of these T cells in marrow, pancreatic lymph nodes (PLNs) and islets.

Administration of multiple doses of peptide/MHC complex. In another study, cohorts of mice are treated with one, two, three or four injections of an effective dose, which the inventors contemplate to be similar for all those complexes exhibiting therapeutic efficacy in other studies (at 4, 7, 10 and 13 wk). It is expected that protection will require one or more than one dose (to expand the memory low-avidity T cell pool above the protective threshold) and that the expanded tetramer+ CD8+ memory T cell population progressively disappears from the circulation to accumulate in marrow, PLNs, and islets.

Administration of peptide/MHC complexes at the onset of hyperglycemia. Mice are treated at the onset of hyperglycemia (>10.5 mM/l) with a more aggressive nanoparticle treatment protocol (1-5 µg peptide equivalents twice a wk for 5 wk). Negative and positive controls will receive nanoparticles coated with an irrelevant peptide/HLA complex or anti-CD3 mAb (a daily i.v. injection of 20 µg for 5 days (Haller, 2005)), respectively. Mice are bled immediately before the initiation of treatment to assess baseline percentages of tetramer-positive CD8+ T cells in the circulation. Reversal of T1D will be considered when blood glucose values stabilize at <10 mM/l for at least 4 weeks at which time treatment with be withdrawn. Mice are bled again to confirm presence of significantly expanded pools of circulating tetramer-positive CD8+ T cells. The animals are followed for at least an additional 8-12 weeks to ensure stable remission. Mice are sacrificed at the end of the observation period to establish the long-term persistence of the expanded pools of memory tetramer-positive CD8+ T cells in different lymphoid and non-lymphoid organs. Pancreas tissue will also be harvested for histological analysis. It is expected that long-term remission will be associated with the presence of numerous small islets devoid of mononuclear cell infiltration. That is, unlike the situation in pre-diabetic mice where the treatment is expected to foster occupation of inflamed islets by protective memory T cells, treatments in diabetic mice is predicted to promote accumulation of the protective memory T cells in the pancreatic lymph nodes (in addition to other reservoirs of memory T cells), but not in islets (presumably newborn islets lacking inflammatory potential).

Peptide/HLA-coated particles work by inducing the deletion of naïve high-avidity clonotypes. The inventors contemplate that low avidity autoreactive CD8+ T cells tend to accumulate as memory cells during T1D progression (in small numbers) and that peptide/HLA-coated particles work by inducing the deletion of naïve high-avidity clonotypes (owing to TCR triggering without costimulation) and the expansion of small pools of pre-existing memory low-avidity clonotypes (costimulation-independent). In part, this stems from the observation that treatment of mice with an irrelevant peptide (from a tumor antigenic, (TUM/H-2 K$^d$) complex did not induce the peripheral expansion of TUM/K$^d$ tetramer-reactive CD8+ T cells above background (see above). These memory low-avidity autoreactive CD8+ cells then inhibit the activation of their naïve high-avidity (presumably less-fitter) counterparts by competing for stimulatory resources (i.e., antigen/MHC on DCs, cytokines, etc.). In fact, there is evidence in other systems that memory cells can compete effectively with naïve T cells for homeostatic cues (i.e., IL-15) (Tan et al., 2002). By making stable contacts with autoantigen-loaded DCs in the PLNs, these prevalent memory low-avidity clonotypes would also inhibit the activation of other autoreactive T cell specificities.

Manifestation of the T cell expansion (and anti-diabetogenic activity) of peptide/HLA-coated nanoparticles requires expression of the endogenous target autoantigen in beta cells. The expression of endogenous target autoantigens are believed to be the source of the stimulus that induces the formation of the memory low avidity autoreactive CD8+ T cell pools that are subsequently expanded by the nanoparticle treatment. An IGRP deficiency will be introduced into NOD.β2m$^{null}$.HHD mice. These mice are treated with hIGRP$_{228-236}$ (cross-reactive with mIGRP$_{228-236}$) and hIGRP$_{265-273}$ (identical to mIGRP$_{265-273}$)/HLA-A*0201-coated nanoparticles (Takaki et al., 2006). Two ES clones carrying a conditional IGRP allele are available to the inventors and are currently undergoing removal of a neomycin cassette by transient transfection of Cre, prior to generating germline-competent chimeras. The targeted alleles will be backcrossed to NOD.β2m$^{null}$.HHD mice (from the 129 strain) using the speed-congenic approach, to ensure homozygosity for NOD alleles at all Idd loci. The resulting NOD.β2m$^{null}$.IGRP$^{null}$.HHD mice are treated with optimal doses of nanoparticles coated with the two IGRP/HLA complexes. The inventors contemplate that the treatment will not induce the expansion/recruitment of the corresponding hIGRP peptide/HLA-reactive CD8+ cells.

If IGRP expression is dispensable for diabetes development (it is known that lack of IGRP expression is not lethal, as rats do not express it) and the mice spontaneously develop diabetes, it is also predicted that the nanoparticle treatment will not protect the mice from T1D (there will be no memory IGRP-reactive CD8+ T cells). In contrast, treatment with particles coated with complexes of HLA-A*0201 and insulin epitopes will induce expansion of the corresponding memory T cell pools and will be protective, as the mice will continue to express insulin.

It is possible that the nanoparticle types to be tested here will not induce significant T cell expansions in all the mice. This will likely depend on whether the corresponding T cell population has previously undergone priming in vivo prior to the initiation of treatment. It may be useful/necessary to study additional cohorts of mice treated with combinations of several different nanoparticle types. Obviously, it is conceivable that, contrary to our prediction, nanoparticle treatment might be able to induce the de novo formation of memory low-avidity T cell pools. In this case, however, the inventors contemplate that these cells will not be protective because they will not be able to engage endogenous IGRP/HLA-A*0201 complexes on DCs in treated NOD.β2m$^{null}$.IGRP$^{null}$.HHD mice.

hIGRP expressing mice. The inventors have generated several lines of mice expressing a rat insulin promoter-driven human IGRP transgene and have compared the levels of expression of the human transgene in each of these lines to that of the endogenous mIGRP-encoding locus by real-time RT-PCR. Although the levels of expression of the transgene were highly variable from line to line, the levels of expression were consistent among different individuals within individual lines. In one of these lines (#1114) the levels of expression of hIGRP were equivalent to those of mIGRP.

The inventors will introduce this RIP-hIGRP transgene into NOD.β2m$^{null}$.IGRP$^{null}$.HHD mice and hβ2m/HLA-A*1101, HLA-B*0702, or HLA-Cw*0304-transgenic NOD.β2m$^{null}$.IGRP$^{null}$ mice, to identify additional epitopes in hIGRP that are targets of CD8$^+$ T cell responses in the context of these four different HLA alleles. The islet-associated CD8$^+$ T cells of these mice will be screened for reactivity against libraries of HLA-A*0201, HLA-A* 1101, HLA-B*0702 and HLA-Cw*0304-binding hIGRP peptides.

The corresponding peptide/HLA complex-coated nanoparticles will then be tested for anti-diabetogenic efficacy in the corresponding hβ2 m/HLA-A*1101, HLA-B*0702, or HLA-Cw*0304-transgenic NOD.β2m$^{null}$.IGRP$^{null}$ mice. The overall objective of this exercise is to expand on the repertoire of peptide/HLA combinations that could be used to treat as many patients as possible.

REFERENCES

The following references, to the extent that they provide exemplary procedural or other details supplementary to those set forth herein, are specifically incorporated herein by reference.

U.S. Pat. No. 4,367,110
U.S. Pat. No. 4,452,901
U.S. Pat. No. 4,554,101
U.S. Pat. No. 4,589,330
U.S. Pat. No. 4,818,542
U.S. Pat. No. 6,103,379
U.S. Pat. No. 6,387,498
U.S. Pat. No. 6,651,655
U.S. Pat. No. 6,712,997
U.S. Publication 20050202032
Aichele et al., *Proc. Natl. Acad. Sci. USA*, 91:444-448, 1994.
Amrani et al., *J. Immunology*, 167:655-666, 2001.
Amrani et al., *Nature*, 406:739-742, 2000.
Anderson et al., *Proc. Natl. Acad. Sci. USA*, 96:9311-9316, 1999.
Anderton and Wraith, *Eur. J. Immunol.*, 28:1251-1261, 1998.
Arden et al., *Diabetes*, 48:531-539, 1999.
Atkinson and Maclaren, *N. Engl. J. Med.*, 331:1428-1436, 1994.
Atkinson and Maclaren, *Sci. Am.*, 7:62-67, 1990.
Banga, In: *Therapeutic Peptides and Proteins. Formulation, Processing, and Delivery Systems*, Technomic Pub. Co., Inc., Lancaster, Pa., 1995.
Barany and Merrifield, In: *The Peptides*, Gross and Meienhofer (Eds.), Academic Press, NY, 1-284, 1979.
Bielekova et al., *Nat. Med.*, 6:1167-1175, 2000.
Bottazzo et al., *N. Engl. J. Med.*, 313:353-360, 1985.
Brinker and Scherer, In: *Sol-gel Science*, Academic Press, 1990.
Burke et al., *J. Inf. Dis.*, 170:1110-1119, 1994.
Cao et al., *Hum. Immunol.*, 62:1009, 2001.
Caruso et al., *Macromolecules*, 32(7):2317-2328, 1999.
Caruso, *J. Amer. Chem. Soc.*, 121(25):6039-6046, 1999.
Castano and Eisenbarth, Annu. Rev. Immunol., 8:647-679, 1990.
Chentoufi and Polychronakos, *Diabetes*, 51:1383, 2002.
Chou and Fasman, *Adv. Enzymol.*, 47:45-148, 1978a.
Chou and Fasman, *Annu. Rev. Biochem.*, 47:251-276, 1978b.
Chou and Fasman, *Biochemistry*, 13(2):211-222, 1974a.
Chou and Fasman, *Biochemistry*, 13(2):222-245, 1974b.
Chou and Fasman, *Biophys. J*, 26(3):385-399, 1979.
Davies, *Advanced Materials*, 10:1264-1270, 1998.
DiLorenzo, et al., *Proc. Natl. Acad. Sci. USA*, 95:12538-12543, 1998.
Doytchinova et al., *J. Immunol.*, 172:4314, 2004.
Epitope Mapping Protocols (1996
Fennessy et al., *Diabetologia*, 37:937-945, 1994.
Golman and Shinohara, *Trends Chem. Engin.*, 6:1-6, 2000.
Goulder et al. *J. Exp. Med.*, 192:1819-1832, 2000.
Group, D.P.T.-T.D.S, *N. Engl. J. Med.*, 346:1685-1691, 2002.
Haller et al., *N. Engl. J. Med.*, 353:2086-2087, 2005.
Hamilton-Williams et al., *Proc. Natl. Acad. Sci. USA*, 98:11533, 2001.
Han et al., *J. Clin. Invest.*, 115:1879 2005.
Han et al., *Nat. Med.*, 11:645-652, 2005.
Hanninen et al., *J. Clin. Invest.*, 90:1901-1910, 1992.
Hanprasopwattana, *Langmuir*, 12:3173-3179, 1996
Honeyman et al., *Mol. Med.*, 1(5):576-582, 1995.
Iler In: *Chemistry of Silica*, John Wiley & Sons, 1979.
Imagawa et al., *Diabetes*, 50:1269-1273, 2001.
Itoh et al., *J. Clin. Invest.*, 92:2313-2322, 1993.
Kappos et al., *Nat. Med.*, 6:1176-1182, 2000.
Karin et al., *J. Exp. Med.*, 180:2227-2237, 1994.
Kent et al., *Nature*, 435:224-228, 2005.
Keymeulen et al. *N. Engl. J. Med.*, 352(25):2598-608, 2005.
Kreuter, In: *Colloidal Drug Delivery Systems*, Marcel Dekker, Inc., NY., 219-342, 1994.
Liblau et al., *Immunity*, 17:1-6, 2002.
Lieberman and DiLorenzo, *Tissue Antigens*, 62:359-377, 2003.
Lieberman et al., *J. Immunol.*, 173:6727, 2004.
Lieberman et al., *Proc. Natl. Acad. Sci. USA*, 100:8384-8388, 2003.
Liu and Wraith, *Int. Immunol.*, 7:1255-1263, 1995.
Maree et al., *Int. Immunol.*, 18:1067-1077, 2006.
Martin et al., *J. Biol. Chem.*, 276:25197-25207, 2001.
McKown, et al., *Arthritis Rheum.*, 42:1204-1208, 1999.
Merrifield, *Science*, 232(4748):341-347, 1986.
Metzler and Wraith, *Int. Immunol.*, 5:1159-1165, 1993.
Miller et al., *J. Exp. Med.*, 149:758-766, 1979.
Moore et al., *Diabetes*, 53:1459-1466, 2004.
Moriwaki et al., *Diabetologia*, 42:1332-1340, 1999.
Nakanishi et al., *J. Clin. Endocrinol. Metab.* 84:3721-3725, 1999.
Nakayama et al., *Nature*, 435:220-224, 2005.
Nejentsev et al., *Diabetes*, 46:1888-1895, 1997.
Owerbach, *Diabetes*, 49:508-512, 2000.
Palmer et al., *Science*, 222:1337-1339, 1983.
Partch and Brown., *J. Adhesion*, 67:259-276, 1998.
Pascolo et al., *J. Exp. Med.*, 185:2043, 1997.
Pekarek et al., *Nature*, 367:258, 1994.
Pinkse et al., *Proc. Natl. Acad. Sci. USA*, 102:18425-18430, 2005.
Pociot and McDermott, *Genes Immun.*, 3:235-249, 2002.
Pozzilli, et al., *Diabetologia*, 43:1000-1004, 2000.
Robles et al., *Clin. Immunol.*, 102:117-224, 2002.
Santamaria et al., *Diabetes*, 41:53-61, 1992.
Santamaria et al., *J. Immunol.*, 154:2494, 1995.
Santamaria, *Curr. Opin Immunol.*, 13:663-669, 2001.
Serreze et al., *Diabetes*, 43:505, 1994.
Serreze et al., *Diabetes*, 50:1992-2000, 2001.
Sibley et al., *Lab. Invest.*, 53:132-144, 1985.
Sidney et al., *Hum. Immunol.*, 45:79, 1996.
Somoza et al., *J. Immunol.*, 153:1360-1377, 1994.
Stewart and Young, In: *Solid Phase Peptide Synthesis*, 2d. ed., Pierce Chemical Co., 1984.
Sukhorukov et al., *Polymers Adv. Tech.*, 9(10-11):759-767, 1998.
Tait et al., *Hum. Immunol.*, 42:116-124, 1995.
Takaki et al., *J. Immunol.*, 176:3257-3265, 2006.
Tam et al., *J. Am. Chem. Soc.*, 105:6442, 1983.

Tan et al., *J. Exp. Med.*, 12:1523-1532, 2002.
Tice & Tabibi, In: *Treatise on Controlled Drug Delivery*, Kydonieus (Ed.), Marcel Dekker, Inc. NY, 315-339, 1992.
Tigges et al., *J. Immunol.*, 156(10):3901-3910, 1996.
Toes et al., *Proc. Natl. Acad. Sci. USA*, 93:7855-7860, 1996.
Toma et al., *Proc. Natl. Acad. Sci. USA*, 102:10581-10585, 2005.
Trentham, et al., *Science*, 261:1727-1730, 1993.
Trudeau et al., *J. Clin. Invest.*, 111:217-223, 2003.
Verdaguer et al., *J Immunology*, 157:4726-4735, 1996.
Verdaguer et al., *J. Exp. Med.*, 186:1663-1676, 1997.
Weiner, *Science*, 259:1321-1324, 1993.
Wong et al., *Nat. Med.*, 5:1026-1031, 1999.
Wraith et al., *Cell*, 59:247-255, 1989.
Yeaman et al., *Ann. NY Acad. Sci.*, 955:174-182, 2002.

What is claimed is:

1. A method of treating type I diabetes or prediabetes, in a patient which method comprises:
   identifying a patient having type I diabetes or prediabetes; and
   administering to said patient an antigen-MHC complex operatively coupled to a non-liposomal nanoparticle in an amount sufficient to expand low avidity anti-pathogenic autoreactive T cells;
   wherein the antigen is a type I diabetes relevant; and
   further wherein said nanoparticle has a diameter of less than 1 µm.

2. The method of claim 1, wherein the MHC component is a MHC class I component.

3. The method of claim 2, wherein the MHC class I component comprises all or part of a HLA-A, HLA-B, HLA-C, HLA-E, HLA-F, HLA-G or CD-1 molecule.

4. The method of claim 2, wherein, the MHC class I component comprises all or part of a HLA-A molecule.

5. The method of claim 2, wherein the MHC class I component comprises all or part of a HLA-A*0201 MHC class I molecule.

6. The method of claim 1, wherein the nanoparticle comprises a metal ion.

7. The method of claim 6, wherein the metal ion is iron (III).

8. The method of claim 1, wherein the antigen-MHC complex is covalently bound to the nanoparticle.

9. The method of claim 8, wherein the complex is bound to the nanoparticle via a linker.

10. The method of claim 9, wherein the linker is one or more of the group a peptide linker, ethylene glycol, biotin, and strepdavidin.

11. The method of claim 1, wherein the T cells expanded by the treatment have been preactivated by type I diabetes and have a memory phenotype.

12. The method of claim 1, wherein the T cell is a CD4$^+$ or CD8$^+$ T cell.

13. A method of treating type I diabetes or prediabetes in a patient in need thereof which method comprises:
   identifying a patient having type I diabetes or prediabetes; and
   administering to said patient a peptide-MHC complex operatively coupled to a non-liposomal nanoparticle in an amount sufficient to expand low avidity anti-pathogenic autoreactive T cells;
   wherein the peptide is a type I diabetes relevant and the MHC is a classical MHC molecule;
   wherein said nanoparticle has a diameter of less than 1 µm; and
   further wherein the peptide is an epitope from an autoantigen expressed by pancreatic beta cells.

14. The method of claim 13, wherein the autoantigen is islet-specific glucose-6-phosphatase catalytic subunit-related protein, insulin, glutamic acid decarboxylase or IA-2 protein.

15. The method of claim 13, wherein the autoantigen is an epitope derived from an endocrine or neurocrine component.

16. The method of claim 15 wherein the endocrine or neuroendocrine component is peri-islet Schwann cells.

17. The method of claim 1 or 13, wherein the method treats type I diabetes.

18. The method of claim 1 or 13, wherein the method treats prediabetes.

19. A method of treating type I diabetes or prediabetes in a patient which method comprises:
   identifying a patient having type I diabetes or prediabetes; and
   administering to said patient an antigen-MHC class II complex operatively coupled to a non-liposomal nanoparticle in an amount sufficient to expand low avidity anti-pathogenic autoreactive T cells;
   wherein the antigen is a type I diabetes relevant antigen; and
   wherein said nanoparticle has a diameter of less than 1 µm.

20. The method of claim 19, wherein the MHC class II component comprises all or part of a HLA-DR, HLA-DQ, or HLA-DP.

21. The method of any one of claims 1, 13 and 19, wherein the non-liposomal nanoparticle comprises a solid core.

* * * * *

UNITED STATES PATENT AND TRADEMARK OFFICE
CERTIFICATE OF CORRECTION

PATENT NO. : 8,354,110 B2
APPLICATION NO. : 12/044435
DATED : January 15, 2013
INVENTOR(S) : Pedro Santamaria et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 559 days.

Signed and Sealed this
Eleventh Day of November, 2014

Michelle K. Lee
*Deputy Director of the United States Patent and Trademark Office*

UNITED STATES PATENT AND TRADEMARK OFFICE
CERTIFICATE OF CORRECTION

Page 1 of 2

PATENT NO. : 8,354,110 B2
APPLICATION NO. : 12/044435
DATED : January 15, 2013
INVENTOR(S) : Pedro Santamaria et al.

It is certified that error appears in the above-identified patent and that said Letters Patent is hereby corrected as shown below:

IN THE CLAIMS

Column 75, line 31, in claim 1, please replace "an antigen-MHC" with --a peptide-MHC--.

Column 75, line 35, in claim 1, please replace "the antigen is a type I diabetes relevant" with --the peptide is a type I diabetes relevant and the MHC is a classical MHC molecule--.

Column 75, lines 38-39, in claim 2, please replace "the MHC component is a MHC class I component" with --the MHC molecule is an MHC class I molecule--.

Column 75, lines 40-41, in claim 3, please replace "the MHC class I component comprises all or part of a HLA-A, HLA-B, HLA-C, HLA-E, HLA-F, HLA-G, or CD-1 molecule" with --the MHC class I molecule comprises all or part of an HLA-A, HLA-B, or HLA-C molecule--.

Column 75, line 43, in claim 4, please replace "the MHC class I component" with --the MHC molecule--.

Column 75, line 45, in claim 5, please replace "the MHC class I component" with --the MHC molecule--.

Column 75, line 52, in claim 8, please replace "the antigen-MHC" with --the peptide-MHC--.

Column 76, line 53, in claim 19, please replace "an antigen-MHC" with --a peptide-MHC--.

Column 76, line 57, in claim 19, please replace "the antigen is a type I diabetes relevant antigen" with --the peptide is a type I diabetes relevant and the MHC class II is a classical MHC class II molecule--.

Signed and Sealed this
Twenty-sixth Day of April, 2016

Michelle K. Lee
*Director of the United States Patent and Trademark Office*

Column 76, lines 60-61, in claim 20, please replace "the MHC class II component" with --the MHC class II molecule--.

Column 76, line 64, in claim 21, please replace "solid core" with --core--.